(12) United States Patent
Desnoyers et al.

(10) Patent No.: US 7,732,567 B2
(45) Date of Patent: Jun. 8, 2010

(54) METHODS AND COMPOSITIONS FOR MODULATING AND DETECTING WISP ACTIVITY

(75) Inventors: Luc Desnoyers, San Francisco, CA (US); Ellen Filvaroff, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/254,649

(22) Filed: Oct. 20, 2008

(65) Prior Publication Data

US 2009/0148448 A1 Jun. 11, 2009

Related U.S. Application Data

(63) Continuation of application No. 11/105,876, filed on Apr. 14, 2005, now Pat. No. 7,455,834, which is a continuation-in-part of application No. 10/519,621, filed as application No. PCT/US03/20407 on Jun. 28, 2003, now Pat. No. 7,456,262.

(60) Provisional application No. 60/392,652, filed on Jun. 29, 2002, provisional application No. 60/408,739, filed on Sep. 6, 2002.

(51) Int. Cl.
 *C07K 4/12* (2006.01)
 *A61K 38/00* (2006.01)
 *A61K 39/00* (2006.01)

(52) U.S. Cl. .................. 530/300; 530/350; 514/12; 424/198.1

(58) Field of Classification Search .......... None
See application file for complete search history.

(56) References Cited

U.S. PATENT DOCUMENTS 7,455,834 B2   6/2006   Desnoyers et al.
7,456,262 B2   6/2006   Desnoyers et al.

FOREIGN PATENT DOCUMENTS

WO   WO 99/21998   5/1999
WO   WO 01/53486   7/2001
WO   WO 2004/003158   1/2004
WO   WO 2005/025603   3/2005

OTHER PUBLICATIONS

Hashimoto et al., (J Exp Med. Feb. 2, 1998;187(3):289-296).*
Xu et al., Genes Dev. Mar. 1, 2000;14(5):585-595.*
Soon et al., (J. Biol. Chem., vol. 278, Issue 13, 11465-11470, Mar. 28, 2003).*
Desnoyers et al., "WISP-1 Binds (2001) to Decorin and Biglycan" *Journal of Biological Chemistry* 276:47599-47607.
International Search Report for PCT/US2006/014008 (Aug 24, 2006).
Pennica et al., "WISP genes are members of the connective tissue growth factor family that are up-regulated in wnt-1-transformed cells and aberrantly expressed in human colon tumors" *Proc. Natl. Acad. Sci.* 95:14717-14722 (Dec. 1998).
Saxena, N. et al., "Differential expression of WSIP-1 and WISP-2 genes in normal and transformed human breast cell lines" *Mol. Cell. Biochem.* 228:99-104 (2001).
Soon et al., "Overexpression inhibition of WISP-1 down-regulated motility and invasion of lung cancer cells through inhibition of Rac activation" *J. Biol. Chemistry* 278(13):11465-11470 (2003).
Xie, D. et al., "Elevated levels of connective tissue growth factor, WISP-1, and CYR61 in primary breast cancers associated with more advanced features" *Cancer Research* 61:8917-8923 (2001).
Xu et al., "WISP-1 is a Wnt-1- and β-catenin-responsive oncogene" *Gene & Develop.* 14:585-595 (2000).
Desnoyers et al., "WISP-1 Binds to Decorin and Biglycan" *Journal of Biological Chemistry* 276:47599-47607 (2001).
Soon et al., "Overexpression of WISP-1 down-regulated motility and invasion of lung cancer cells through inhibition of Rac activation" *J. Biol. Chemistry* 278 (13):11465-11470 (2003).

* cited by examiner

*Primary Examiner*—David S Romeo
*Assistant Examiner*—Daniel C Gamett

(57) ABSTRACT

Methods and compositions for use in modulating the activity(s) of WISP-1 polypeptide are provided. WISP-1 antagonists include anti-WISP-1 antibodies, WISP-1 immunoadhesins and WISP-1 variants (and fusion proteins thereof) which inhibit or neutralize induction or secretion of HAS2, HA, CD44 or RHAMM by native human WISP-1 polypeptide in at least one type of mammalian cell. The invention also provides methods for in vitro, in situ, and/or in vivo diagnosis and/or treatment of mammalian cells or pathological conditions associated with native WISP-1 polypeptides.

28 Claims, 36 Drawing Sheets

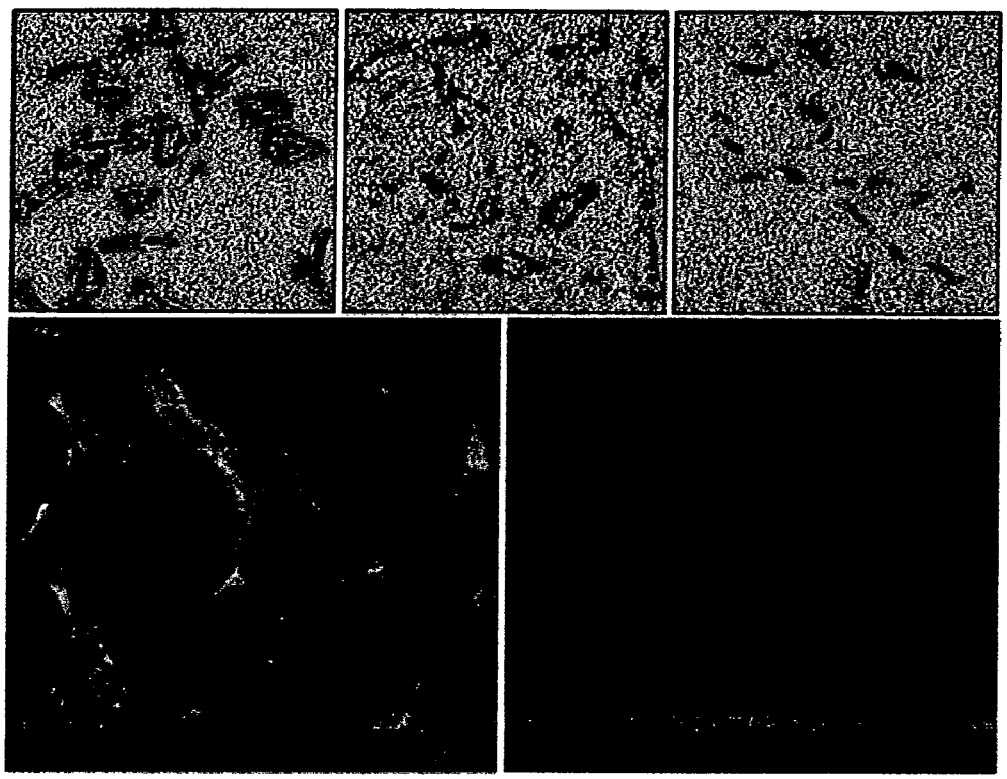
FIG._1A  FIG._1B  FIG._1C
FIG._1D  FIG._1E
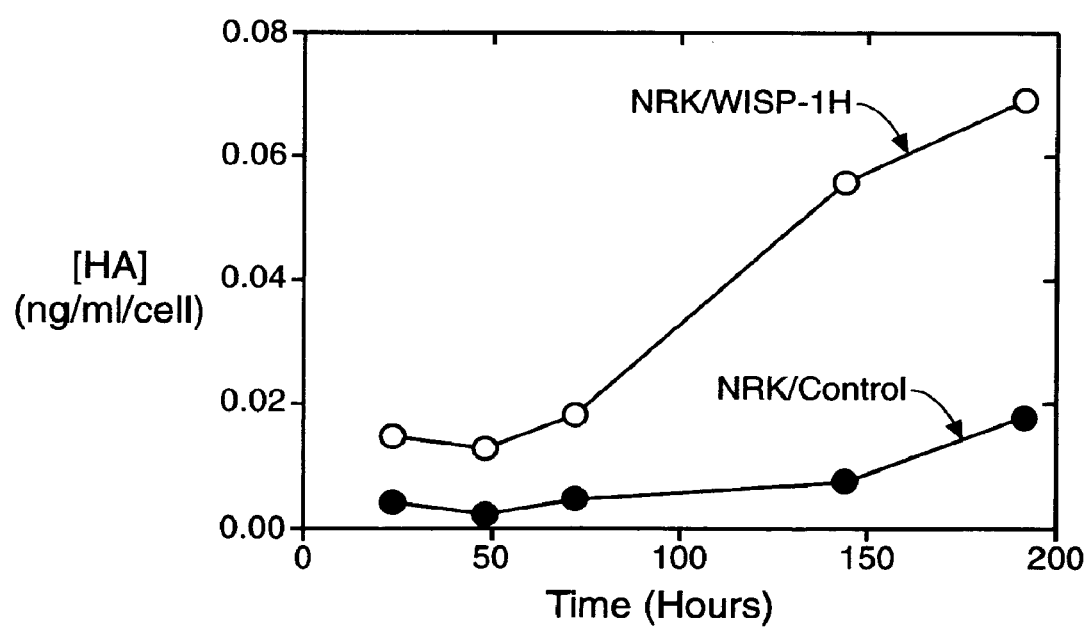
FIG._1F

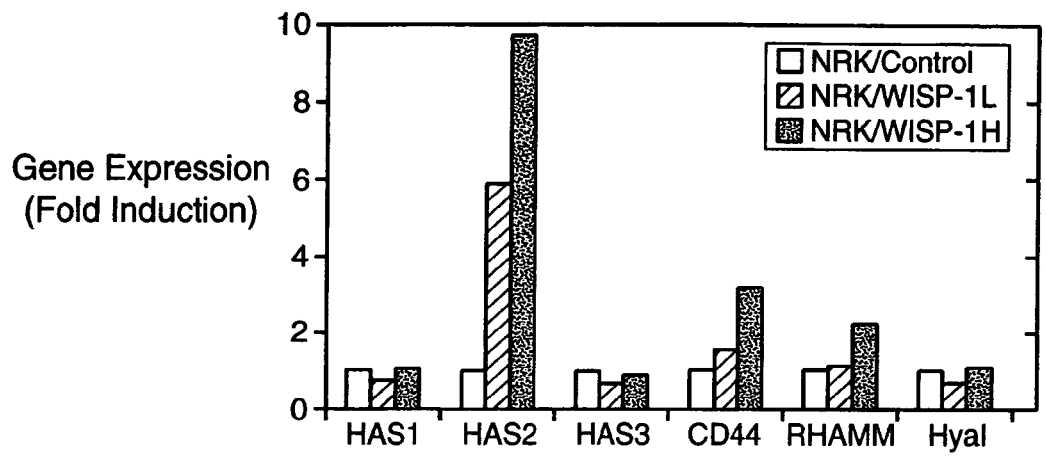
FIG._2A
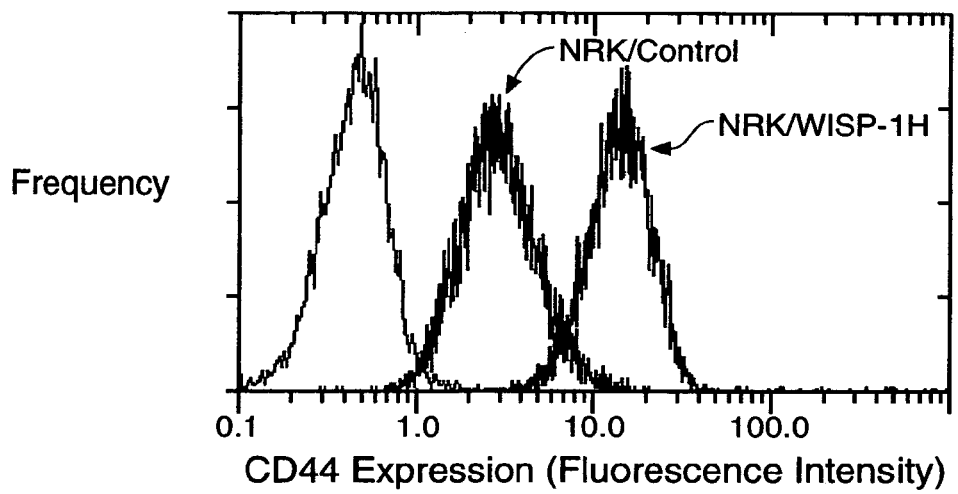
FIG._2B
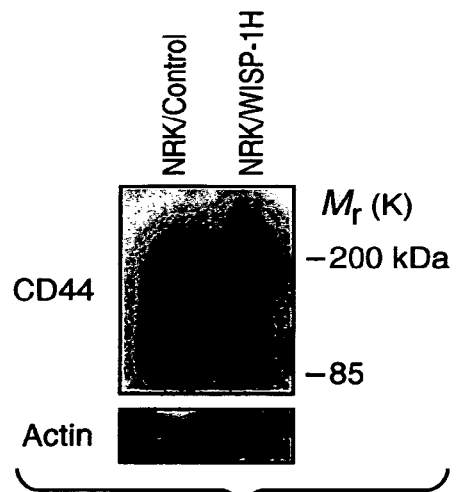
FIG._2C

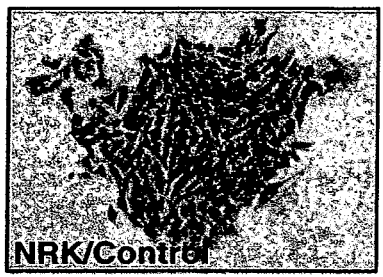
FIG._3A
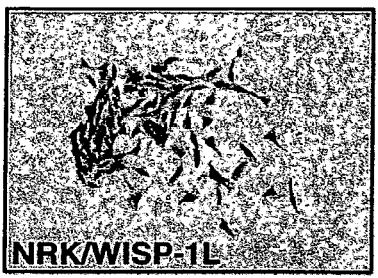
FIG._3B
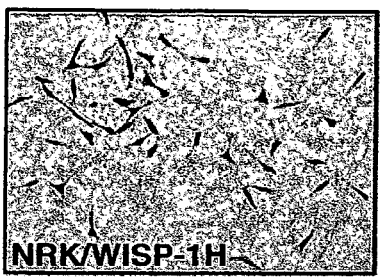
FIG._3C
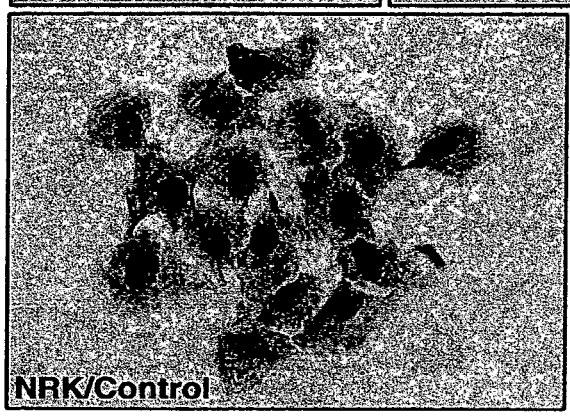
FIG._3D
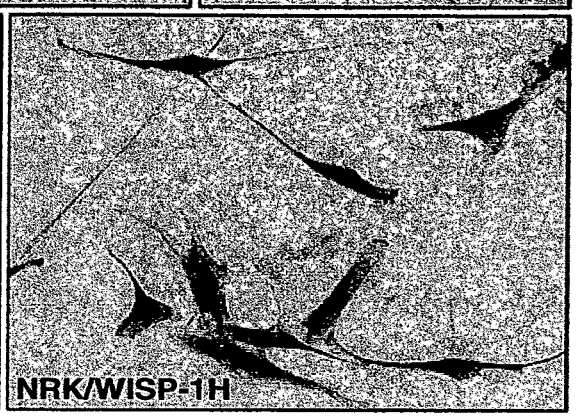
FIG._3E
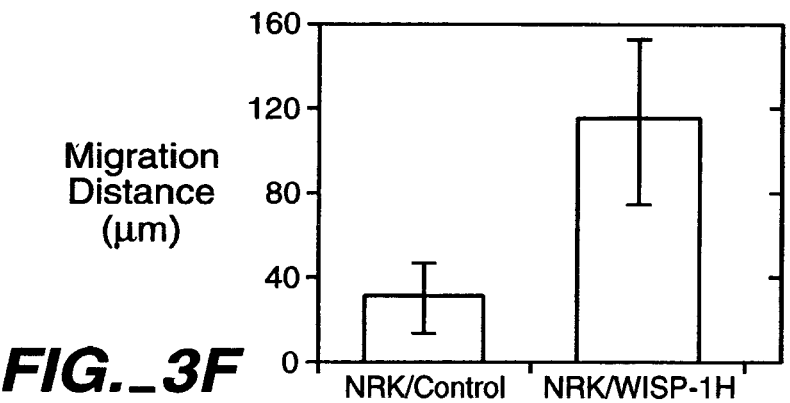
FIG._3F
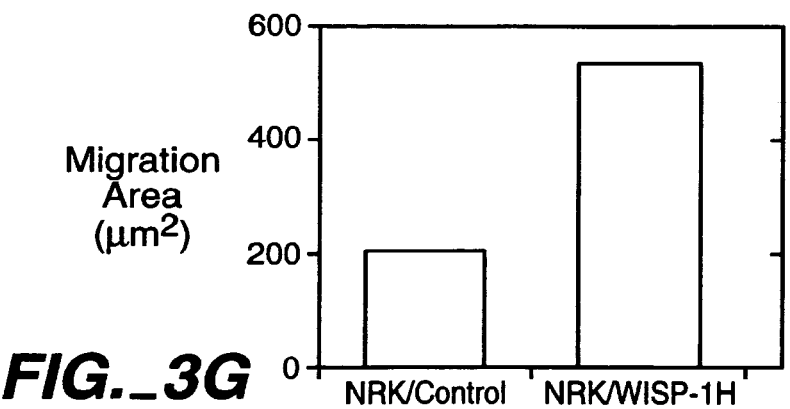
FIG._3G

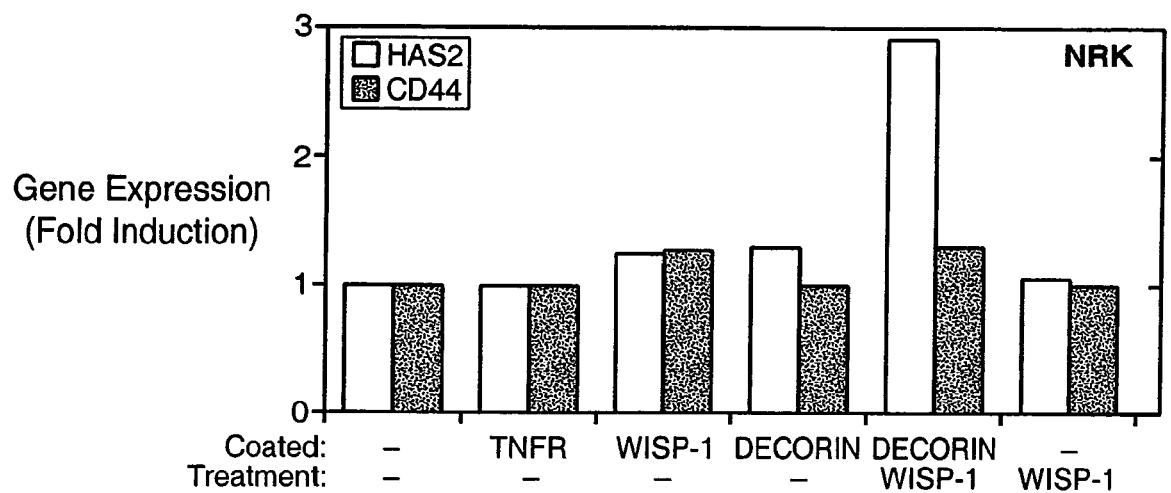
FIG._4A
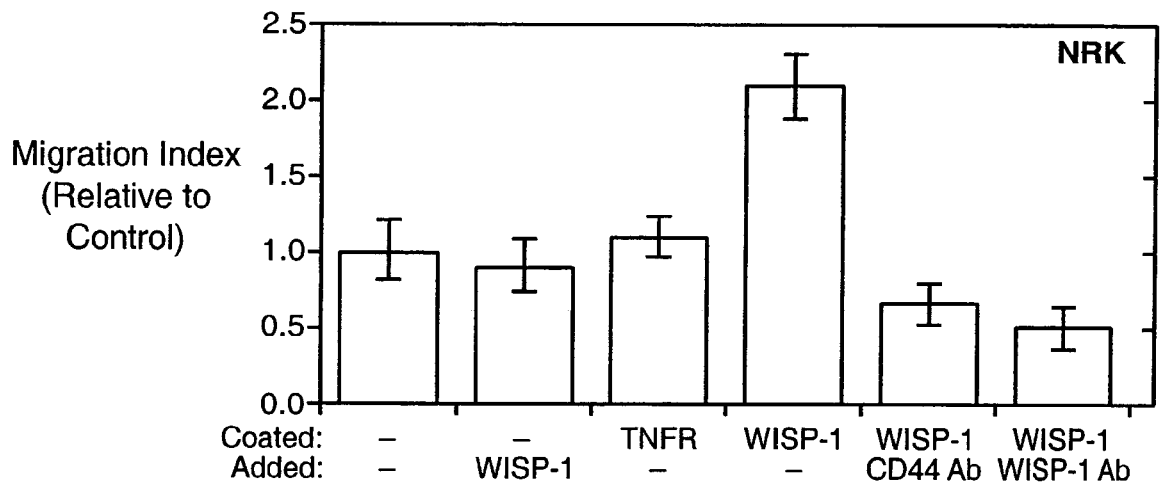
FIG._4B
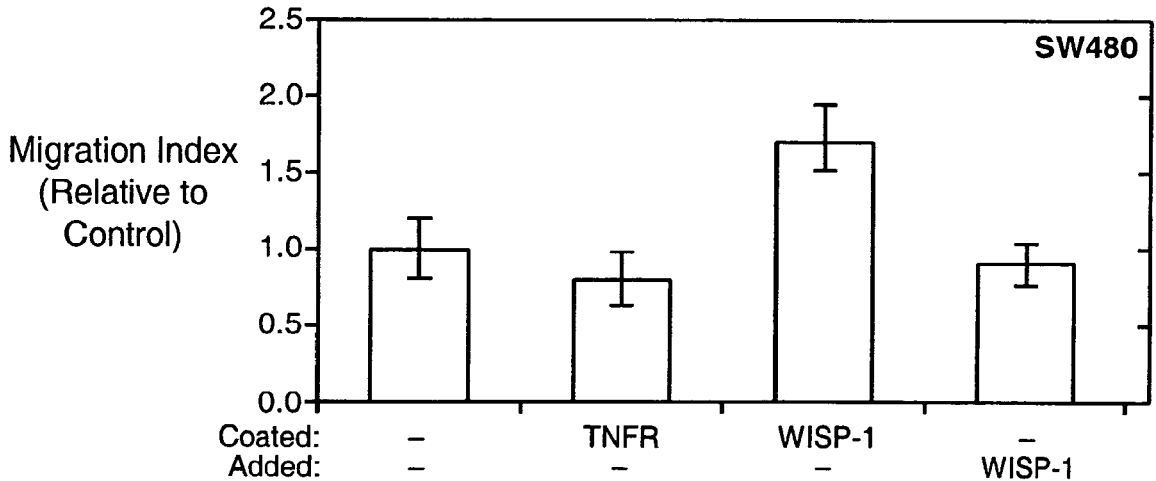
FIG._4C

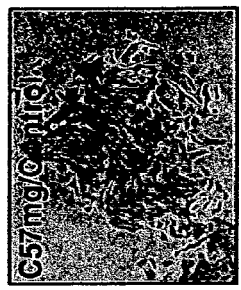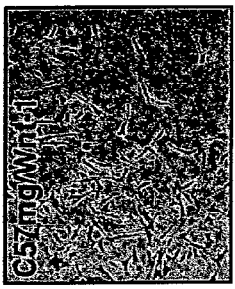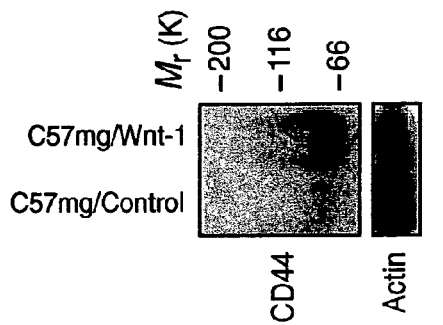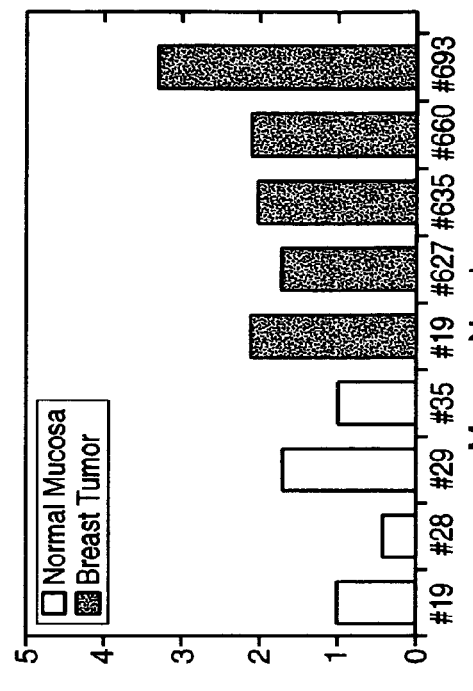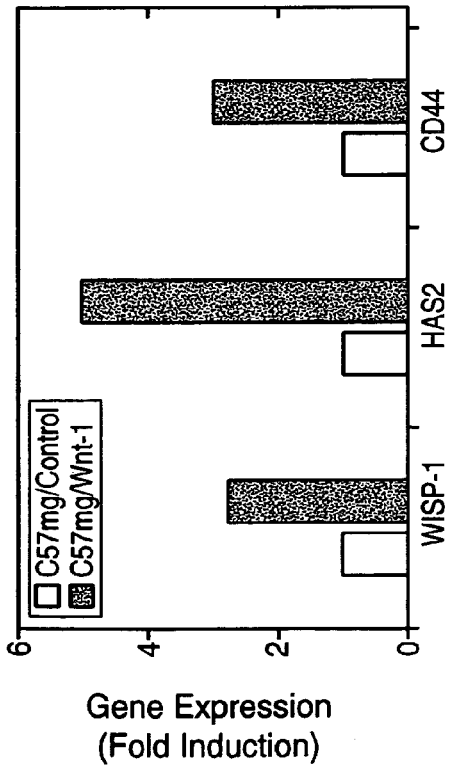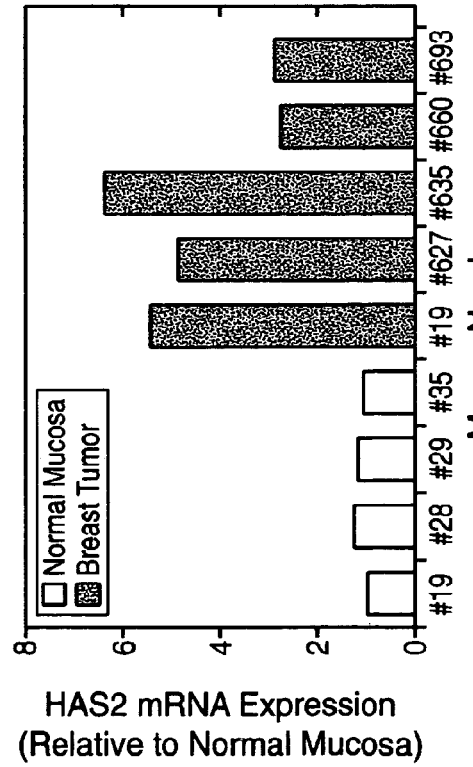

FIG._6A
FIG._6B
FIG._6C
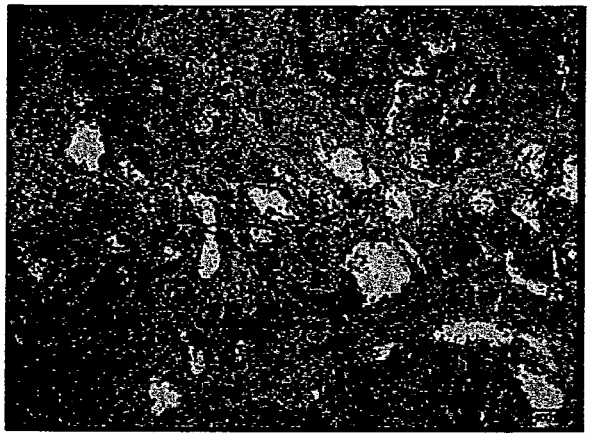
FIG._6D
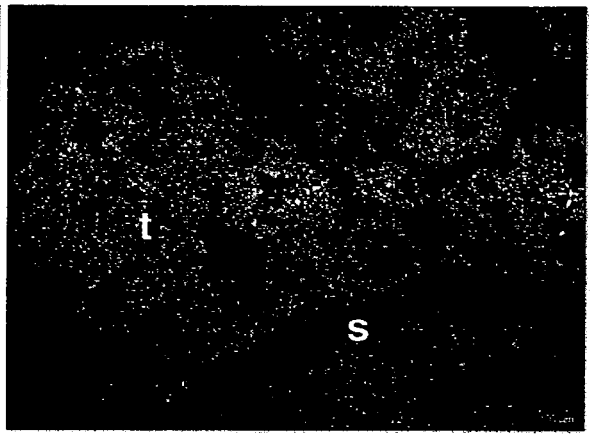

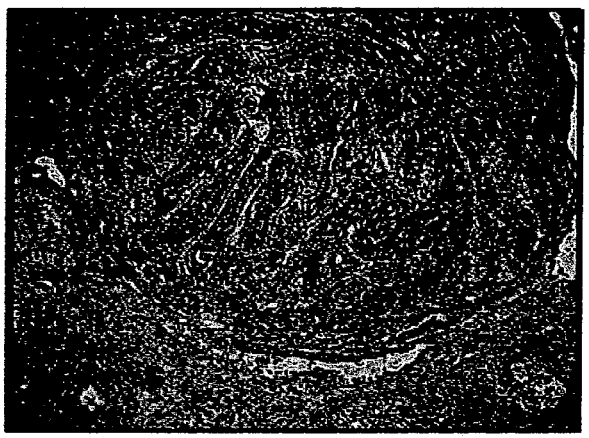
FIG._6E
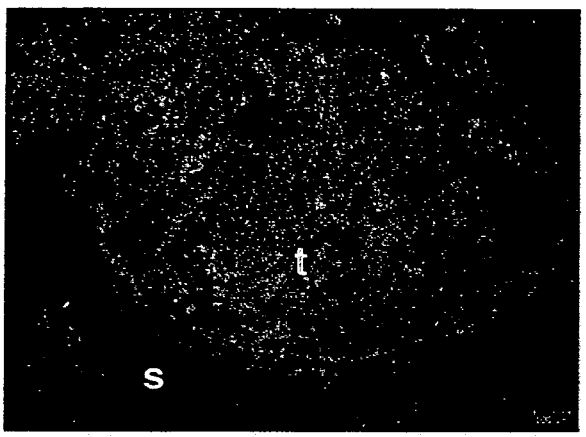
FIG._6F
FIG._6G
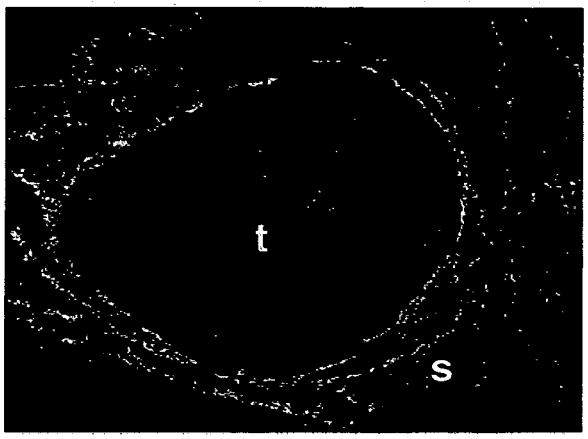
FIG._6H

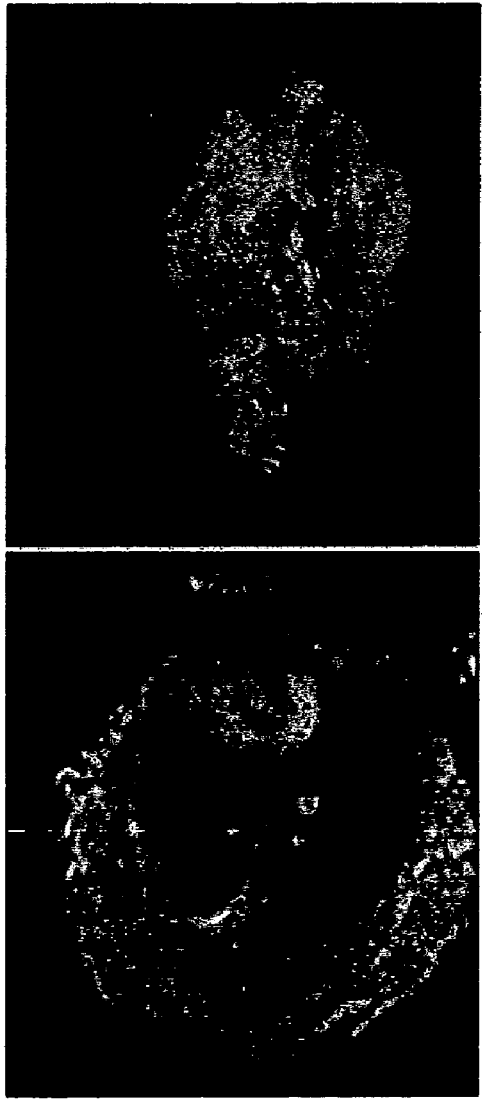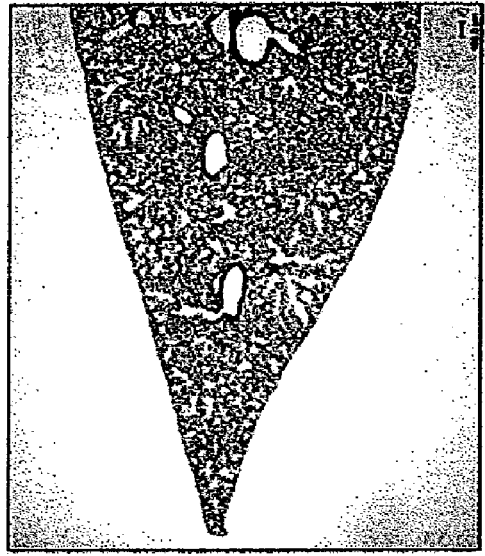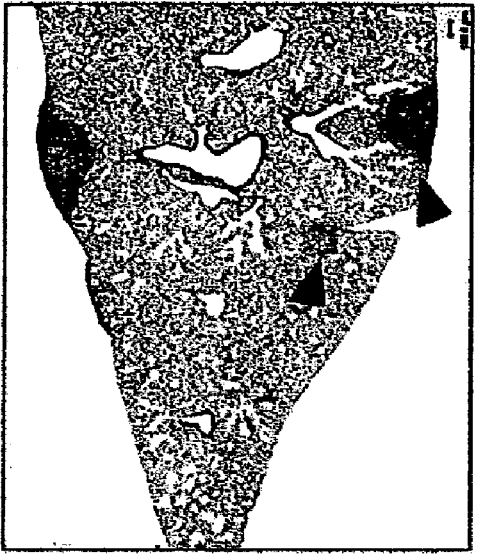

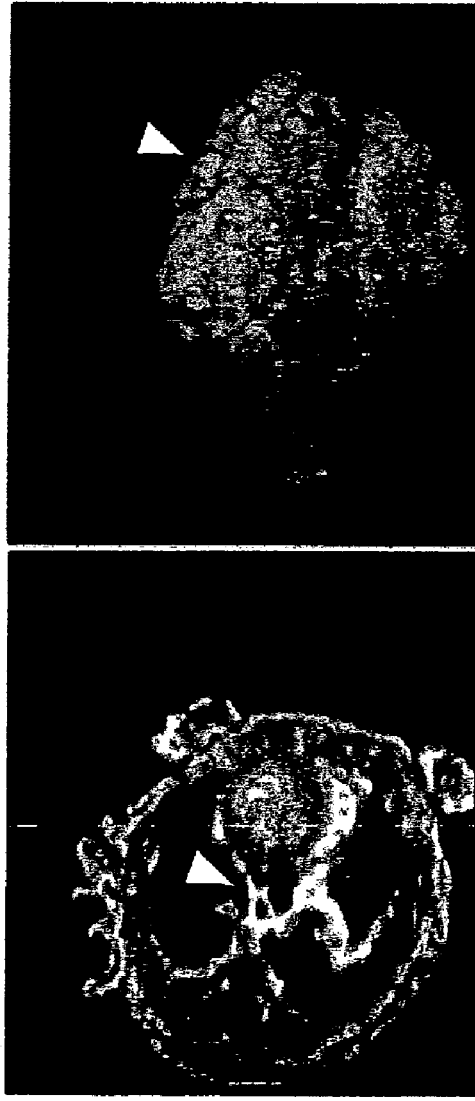
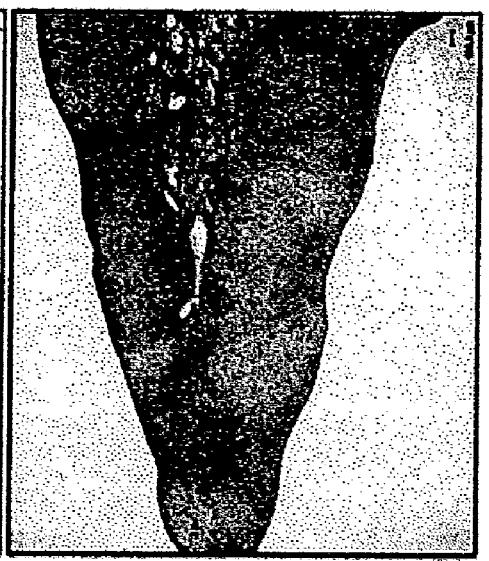
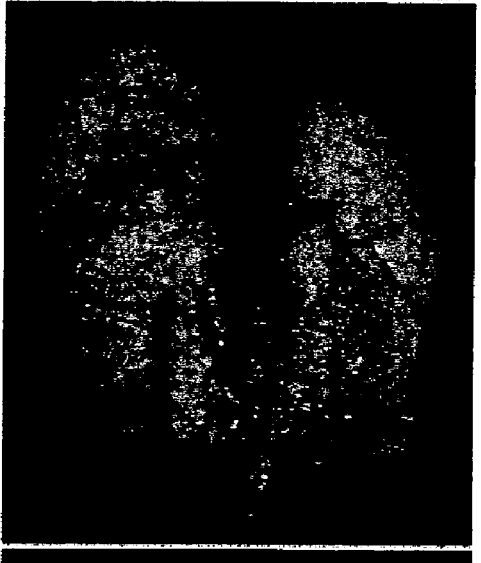
FIG._7G  FIG._7H  FIG._7I
FIG._7J  FIG._7K  FIG._7L

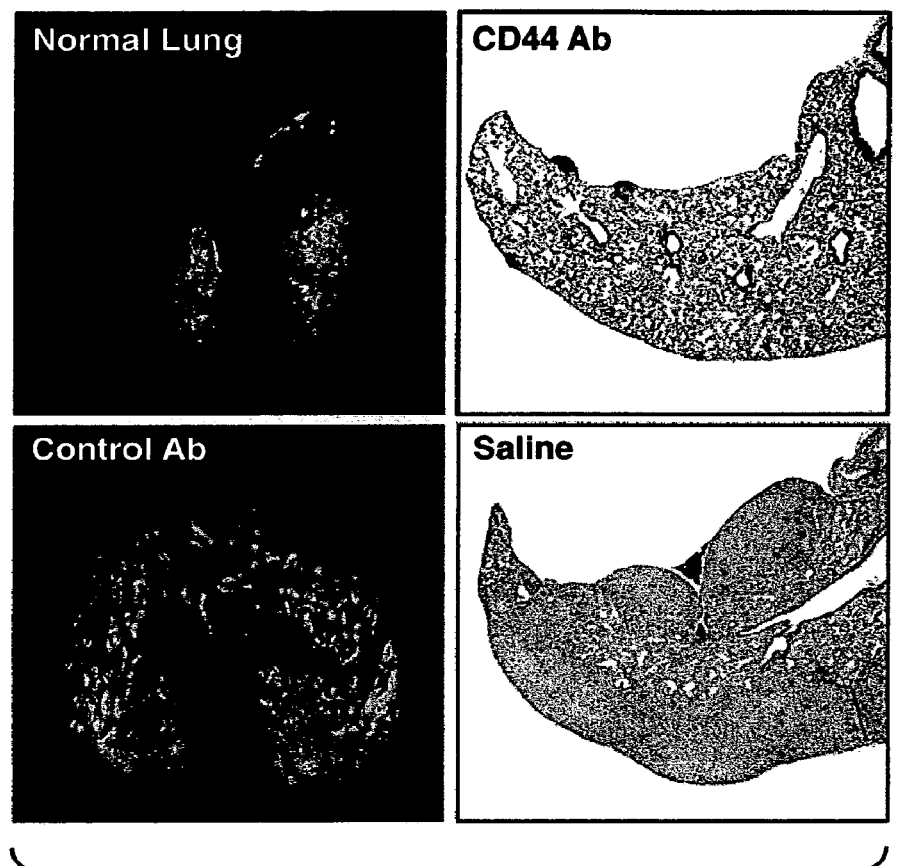
*FIG._8A*
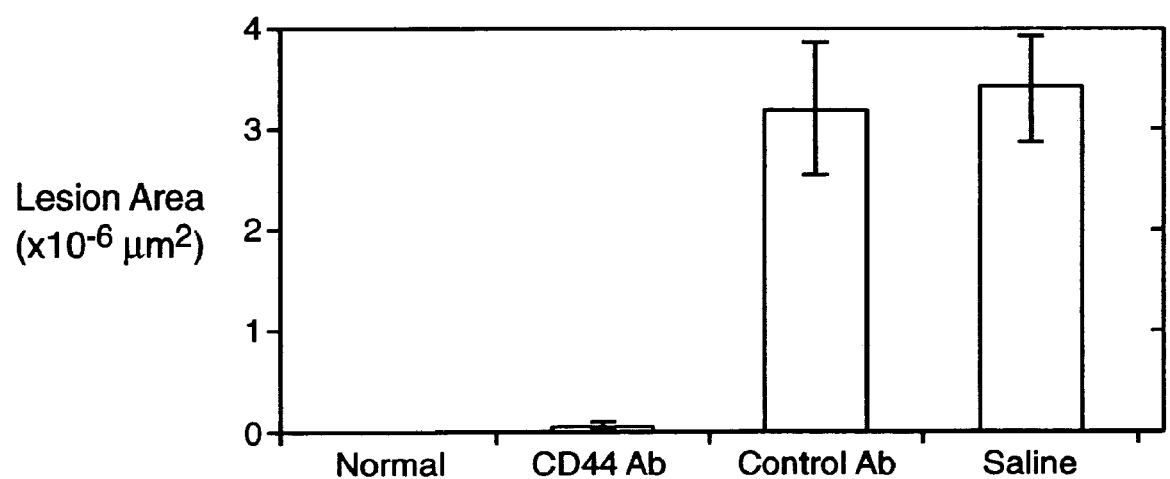
*FIG._8B*

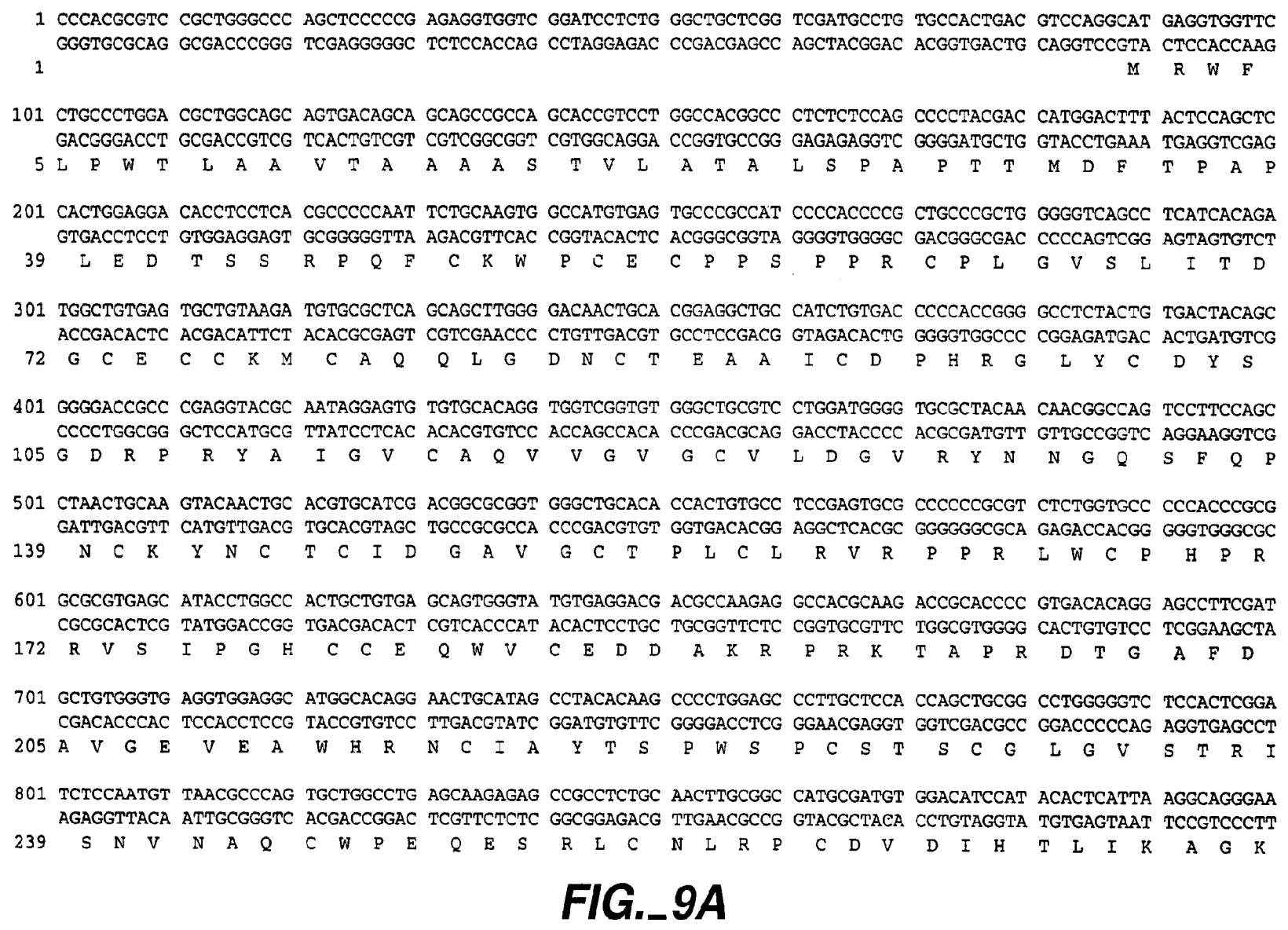

FIG._9A

```
 901 GAAGTGTCTG GCTGTGTACC AGCCAGAGGC ATCCATGAAC TTCACACTTG CGGGCTGCAT CAGCACACGC TCCTATCAAC CCAAGTACTG TGGAGTTTGC
     CTTCACAGAC CGACACATGG TCGGTCTCCG TAGGTACTTG AAGTGTGAAC GCCCGACGTA GTCGTGTGCG AGGATAGTTG GGTTCATGAC ACCTCAAACG
 272  K  C  L   A  V  Y  Q   P  E  A   S  M  N   F  T  L   A  G  C  I   S  T  R   S  Y  Q  P   K  Y  C   G  V  C

1001 ATGGACAATA GGTGCTGCAT CCCCTACAAG TCTAAGACTA TCGACGTGTC CTTCCAGTGT CCTGATGGGC TTGGCTTCTC CCGCCAGGTC CTATGGATTA
     TACCTGTTAT CCACGACGTA GGGGATGTTC AGATTCTGAT AGCTGCACAG GAAGGTCACA GGACTACCCG AACCGAAGAG GGCGGTCCAG GATACCTAAT
 305  M  D  N   R  C  C  I   P  Y  K   S  K  T  I   D  V  S   F  Q  C   P  D  G  L   G  F  S   R  Q  V   L  W  I  N

1101 ATGCCTGCTT CTGTAACCTG AGCTGTAGGA ATCCCAATGA CATCTTTGCT GACTTGGAAT CCTACCCTGA CTTCTCAGAA ATTGCCAACT AGGCAGGCAC
     TACGGACGAA GACATTGGAC TCGACATCCT TAGGGTTACT GTAGAAACGA CTGAACCTTA GGATGGGACT GAAGAGTCTT TAACGGTTGA TCCGTCCGTG
 339  A  C  F   C  N  L   S  C  R  N   P  N  D   I  F  A   D  L  E  S   Y  P  D   F  S  E   I  A  N  O

1201 AAATCTTGGG TCTTGGGGAC CCTGTGAAGC AGTCAGCCCT TATGGCCAAT AACTTTTCAC CAATGAGCCT TAGTTACCCT GATCTGGACC
     TTTAGAACCC AGAACCCCTG GGACACTTCG TCAGTCGGGA ATACCGGTTA TTGAAAAGTG GTTACTCGGA ATCAATGGGA CTAGACCTGG

1301 CTTGGCCTCC ATTTCTGTCT CTAACCATTC AAATGACGCC TGATGGTGCT GCTCAGGCCC ATGCTATGAG TTTTCTCCTT GATATCATTC AGCATCTACT
     GAACCGGAGG TAAAGACAGA GATTGGTAAG TTTACTGCGG ACTACCACGA CGAGTCCGGG TACGATACTC AAAAGAGGAA CTATAGTAAG TCGTAGATGA

1401 CTAGCTGTTC ATGCCTGTCT TGGACTACAC CCAAGCCTGA TTCCTTTAGAT AGAAGTCCTG AGAAGTCTTT GGGTCCATTC AGATGAATAG CCTAAATCCC
     GATTCGACAA TACGGACAGA ACCTGATGTG GGTTCGGACT AAGAAATCTA TCTTCAGGAC AAGACTCTT CCCAGGTAAG TCTACTTATC GGATTTAGGG

1501 AAGAAATGGA ATCAGGTAGA CTTTTAATAT CACTAATTTC GGTAATTCTG GGTTAATTCTG GGTCCATTG AGATGAATAG ATGGAATTTG
     TTCTTTACCT TAGTCCATCT GAAAATTATA GTGATTAAAG AAGAAATCTA CGGTTAAGAC CCAATTAAGAC CCCAGGTAAG TCTACTTATC TACCTTAAAC

1601 GAACAATAGA ATAATCTATT ATTTGGAGCC TGCCAAGAGG TACTGTAATG CCATTAAGAC CCATTAAGAC CCCAGGTAAG TCCTGATTCC AAATATGTAT
     CTTGTTATCT TATTAGATAA TAAACCTCGG ACGGTTCTCC ATGACATTAC CCATTAAGAC CCATTAAGAC CCCAGGTAAG TCTACTTATC AGGACTAAGG TTTATACATA

1701 GCACCTCAAG GTCATCAAAC ATTTGCCAAG TGAGTTGAAT AGTTGCTTAA TCAACGAATT CCAGTCAGAA ATAAAATTTG CCATTAAGAC ATTGTTGAGG
     CGTGGAGTTC CAGTAGTTG TAAACGGTTC ACTCAACGTT TCAACGAATT AGTTGCTTAA CCAGTCAGAA ATAAAATTTG CCATTAAGAC TAACAACTCC

1801 TTAAGTTTCT CTTCACCCCT ACACTGTGAA GGGTACAGAT TAGGTTGTAA CCAGTCAGAA ATAAACATTC ATAAAATTTG CTGTTGATGG GAAAAGCCCC
     AATTCAAGA GAAGTGGGGA TGTGACACTT CCCATGTCTA ATCCAACAG GGTCAGTCTT TATTTGTAAG GACAACTACC CTTTTCGGGG

1901 CAGTAATATAC TCCAGAGACA GGGAAAGGTC AGCCCATTTC AGAAGGACCA ATTGACTCTC ACACTGAATC AGCTGCTGAC TGGCAGGGCT TTGGGCAGTT
     GTCAATTATG AGTCTCTGT CCCTTTCCAG TCGGGTAAAG TCTTCCTGGT TAACTGAGAG TGTGACTTAG TCGACGACTG ACCGTCCCGA AACCGTCAA
```

*FIG._9B*

```
2001  GGCCAGGCTC TTCCTTGAAT CTTCTCCCTT GTCCTGCTTG GGTTCATAGG AATTGGTAAG GCCTCTGGAC TGGCCTGTCT GGCCCCTGAG AGTGGTGCCC
      CCGGTCCGAG AAGGAACTTA GAAGAGGGAA CAGGACGAAC CCAAGTATCC TTAACCATTC CGGAGACCTG ACCGGACAGA CCGGGGACTC TCACCACGGG

2101  TGGAACACTC CTCTACTCTT ACAGAGCCTT GAGAGACCCA GCTGCAGACC ATGCCAGACC CACTGAAATG ACCAAGACAG GTTCAGGTAG GGGTGTGGGT
      ACCTTGTGAG GAGATGAGAA TGTCTCGGAA CTCTCGGGT CGACGTCTGG TACGGTCTGG GTGACTTTAC TGGTTCTGTC CAAGTCCATC CCCACACCCA

2201  CAAACCAAGA AGTGGGTGCC CTTGGTAGCA GCCTGGGGTG ACCTCTAGAG CTGGAGGCTG TGGGACTCCA GGGGCCCCCG TGTTCAGGAC ACATCTATTG
      GTTTGGTTCT TCACCCACGG GAACCATCGT CGGACCCCAC TGGAGATCTC GACCTCCGAC ACCCTGAGGT CCCCGGGGGC ACAAGTCCTG TGTAGATAAC

2301  CAGAGACTCA TTTCACAGCC CTGACCAAAT GGCCAGTTTT CTGGTAGGAA GATGGAGGTT TACCAGTTGT TTAGAAACAG AAATAGACTT
      GTCTCTGAGT AAAGTGTCGG GACTGGTTTA CCGGTCAAAA GACCATCCTT CTACCTCCAA ATGGTCAACA AATCTTTGTC TTTATCTGAA

2401  AATAAAGGTT TAAAGCTGAA GAGGTTGTTG CTAAAAGGAA AAGGTTGTTG TTAATGAATA TCAGGCTATT ATTTATTGTA TTAGGAAAAT ATAATATTTA
      TTATTCCAA ATTTCGACTT CTCCAACTTC GATTTTCCTT TTCCAACAAC AATTACTTAT AGTCCGATAA TAAATAACAT AATCCTTTTA TATTATAAAT

2501  CTGTTAGAAT TCTTTTATTT AGGGCCTTTT CTGTGCCAGA CATTGCTCTC AGTGCTTTGC ATGTATTAGC TCACTGAATC TTCACGACAA TGTTGAGAAG
      GACAATCTTA AGAAATAAA TCCCGGAAAA GACACGGTCT GTAACGAGAG TCACGAAACG TACATAATCG AGTGACTTAG AAGTGCTGTT ACAACTCTTC

2601  TTCCATTAT TATTTCTGTT CTTACAAATG TGAAACGGAA GCTCATAGAG GTGAGAAAAC TCAACCAGAG TCACCCAGTT GGTGACTGGG AAAGTTAGGA
      AAGGTAATA ATAAAGACAA GAATGTTAC ACTTTGCCTT CGAGTATCTC CACTCTTTTG AGTTGGTCTC AGTGGGTCAA CCACTGACCC TTTCAATCCT

2701  TTTCAGATCGA AATTGGACTG TCTTTATAAC CCATATTTC TAGAGCTTCC AAATGTGTCA GAATAGGAAA ACATTGCAAT AAATGGCTTG
      AAGTCTAGCT TTAACCTGAC AGAAATATTG GGTATAAAAG GGGGACAAAA ATCTCGAAGG TTTACACAGT CTTATCCTTT TGTAACGTTA TTTACCGAAC

2801  ATTTTTTAAA AAAAAAAAAA AAAAAAAAAA
      TAAAAAATTT TTTTTTTTTT TTTTTTTTTT
```

FIG._9C

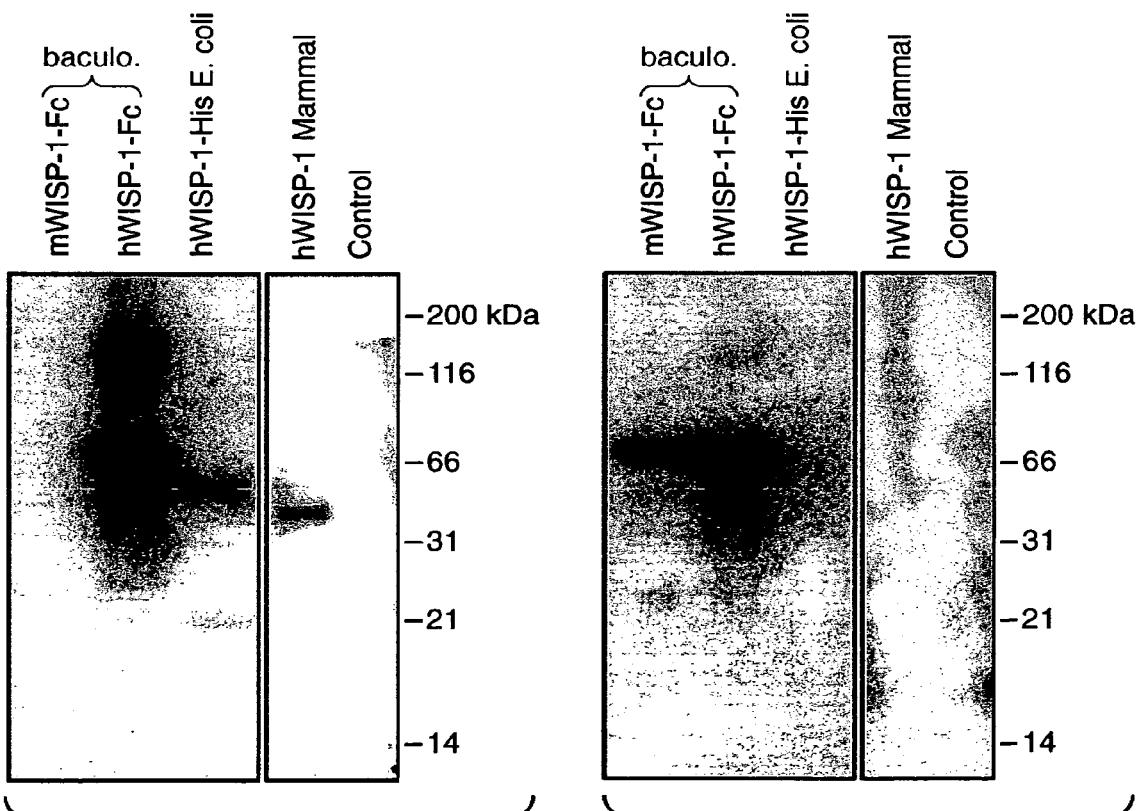
FIG._10
FIG._11A    FIG._11B

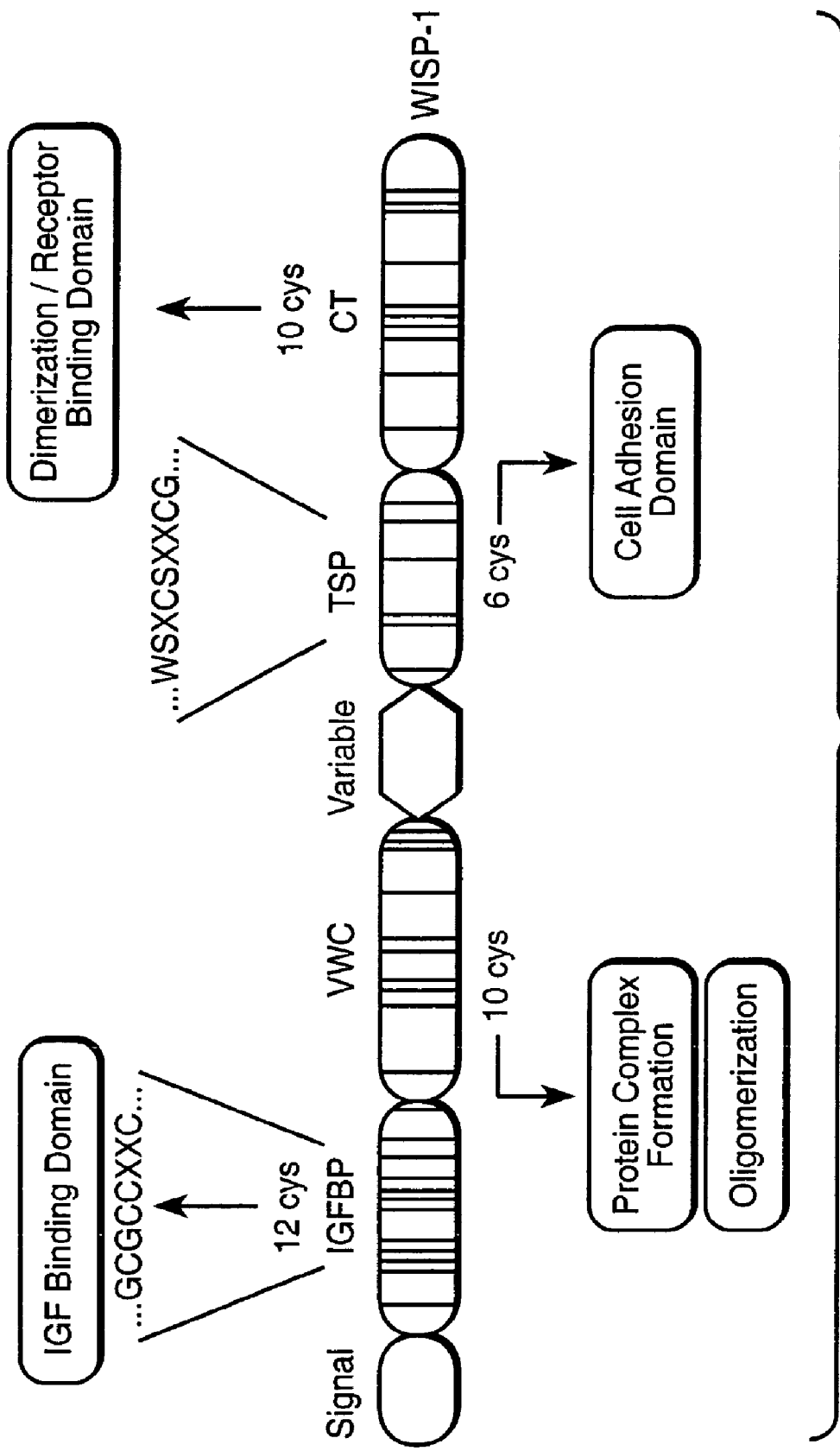
FIG. _12A

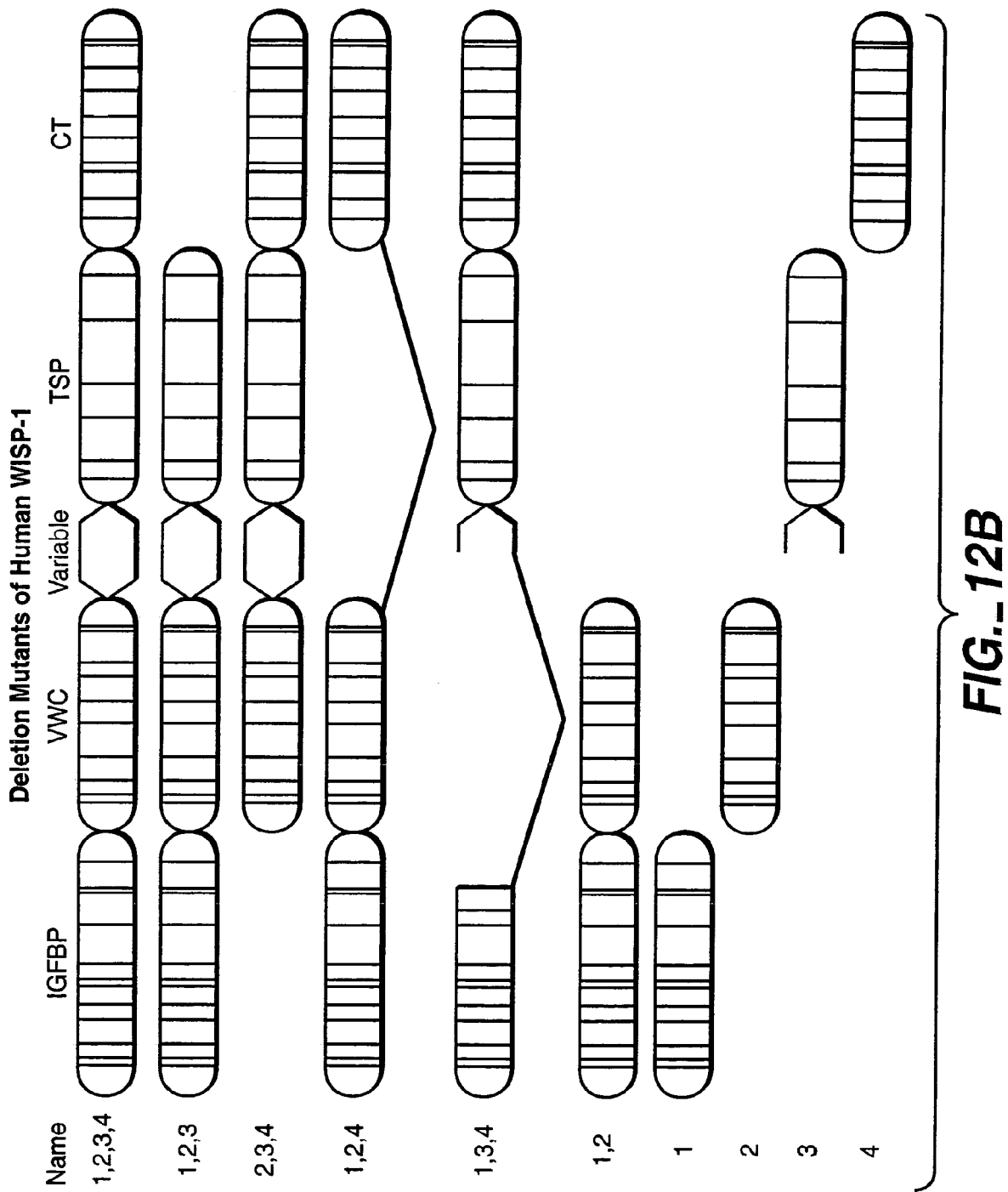
FIG._12B

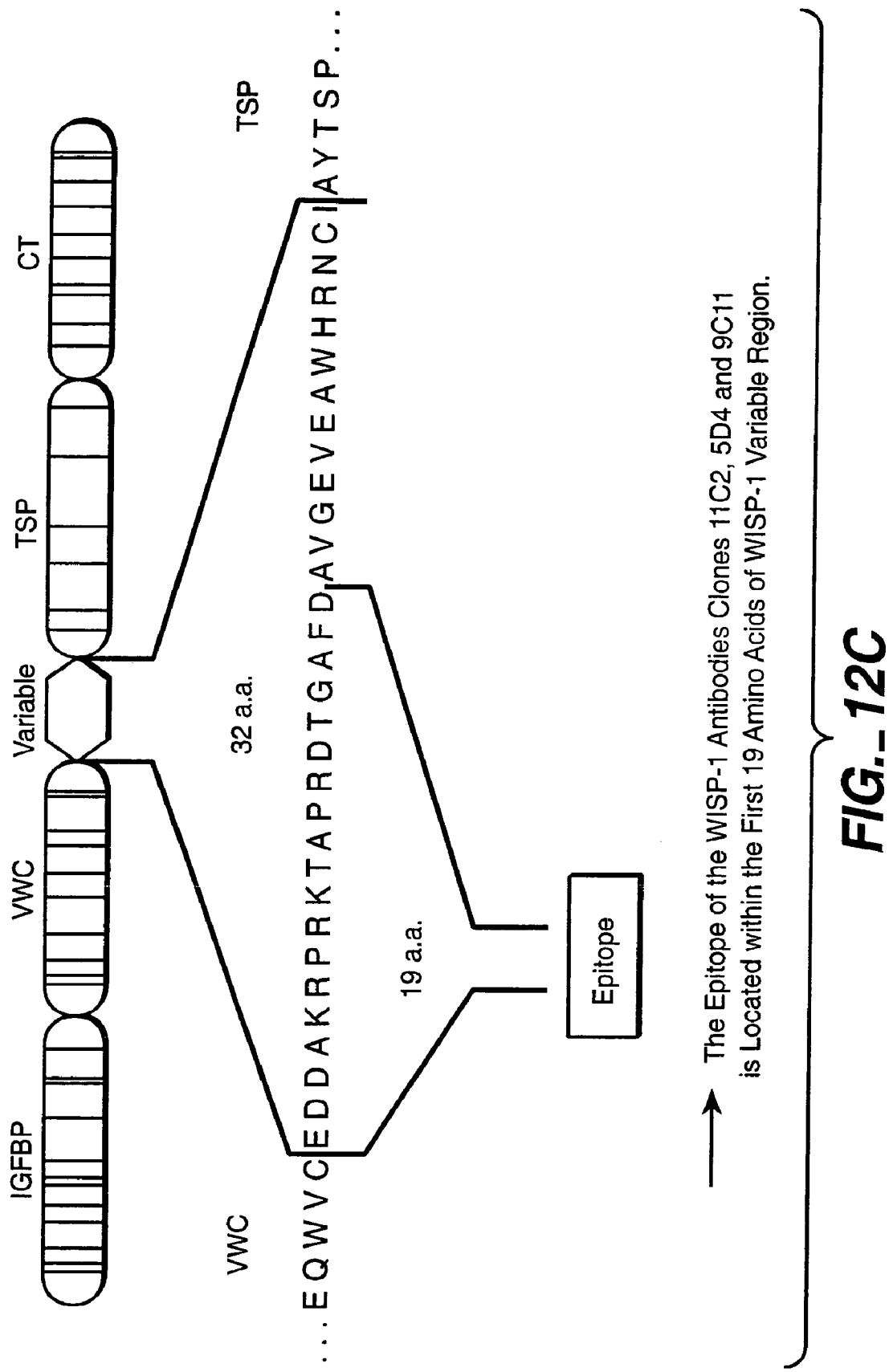
FIG._12C

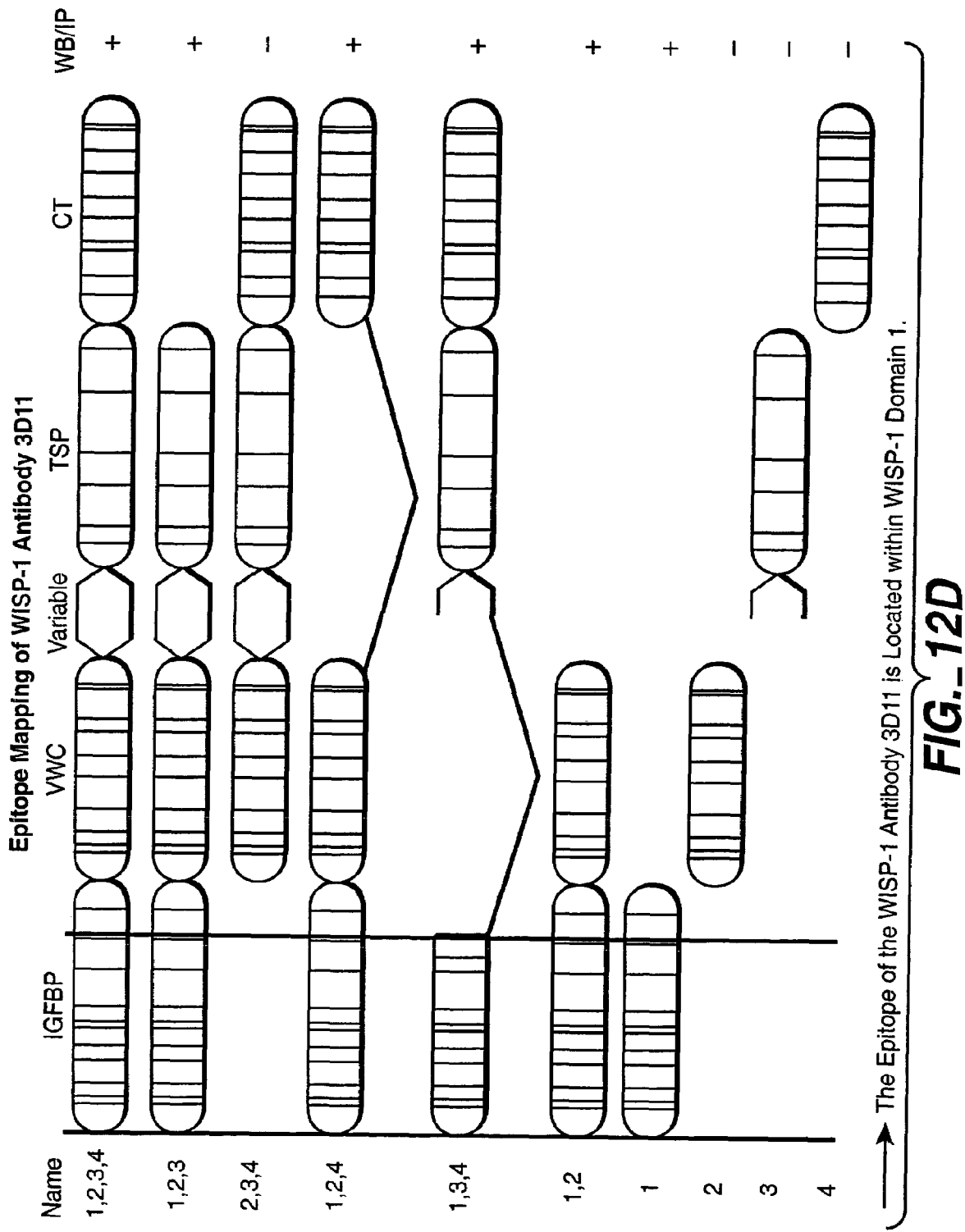

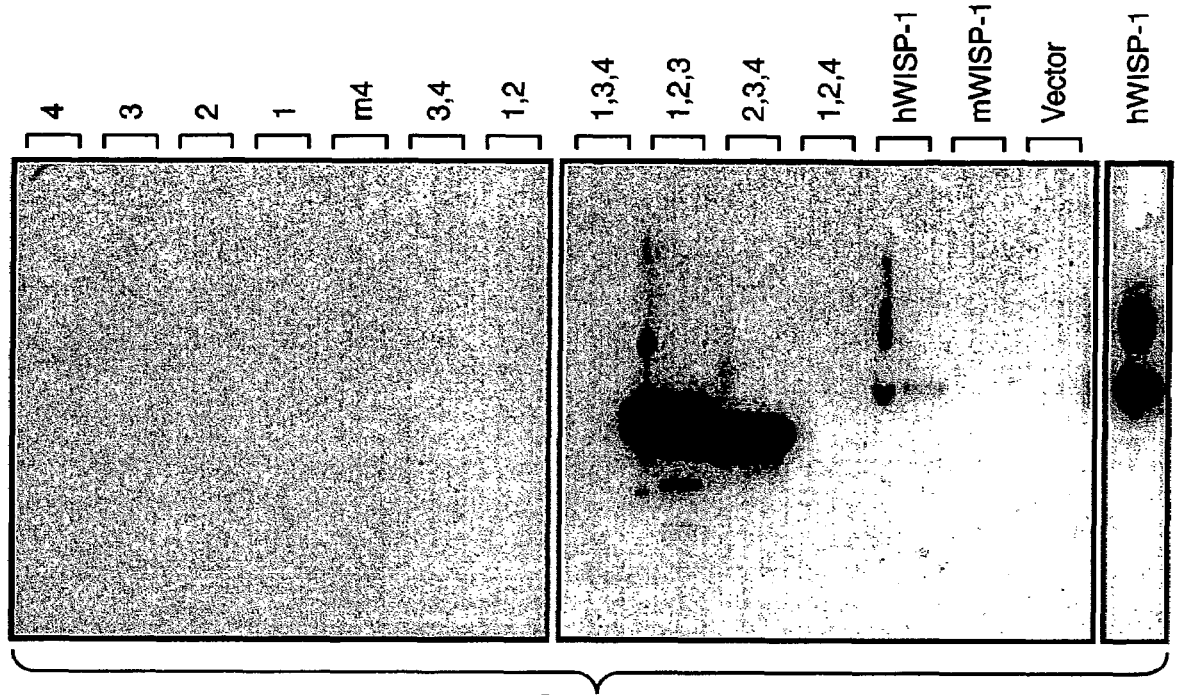
FIG. _12E
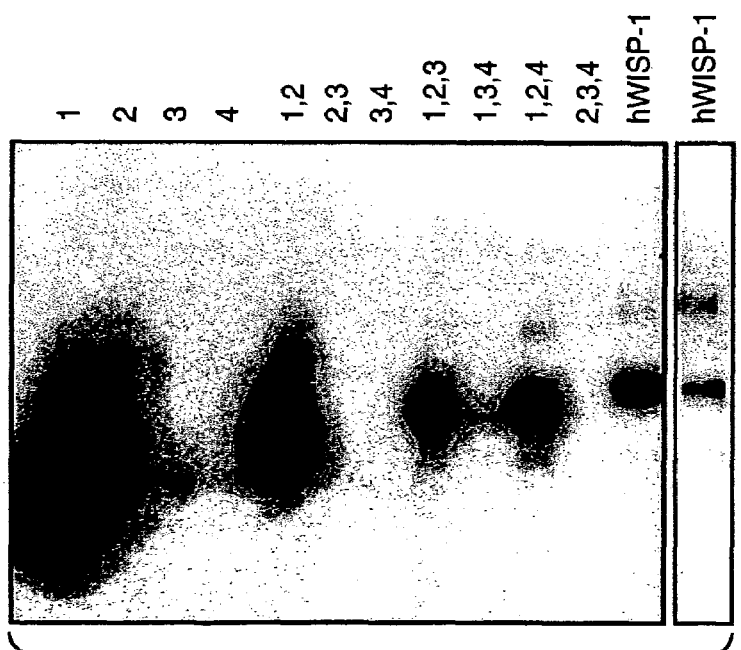
FIG. _12F

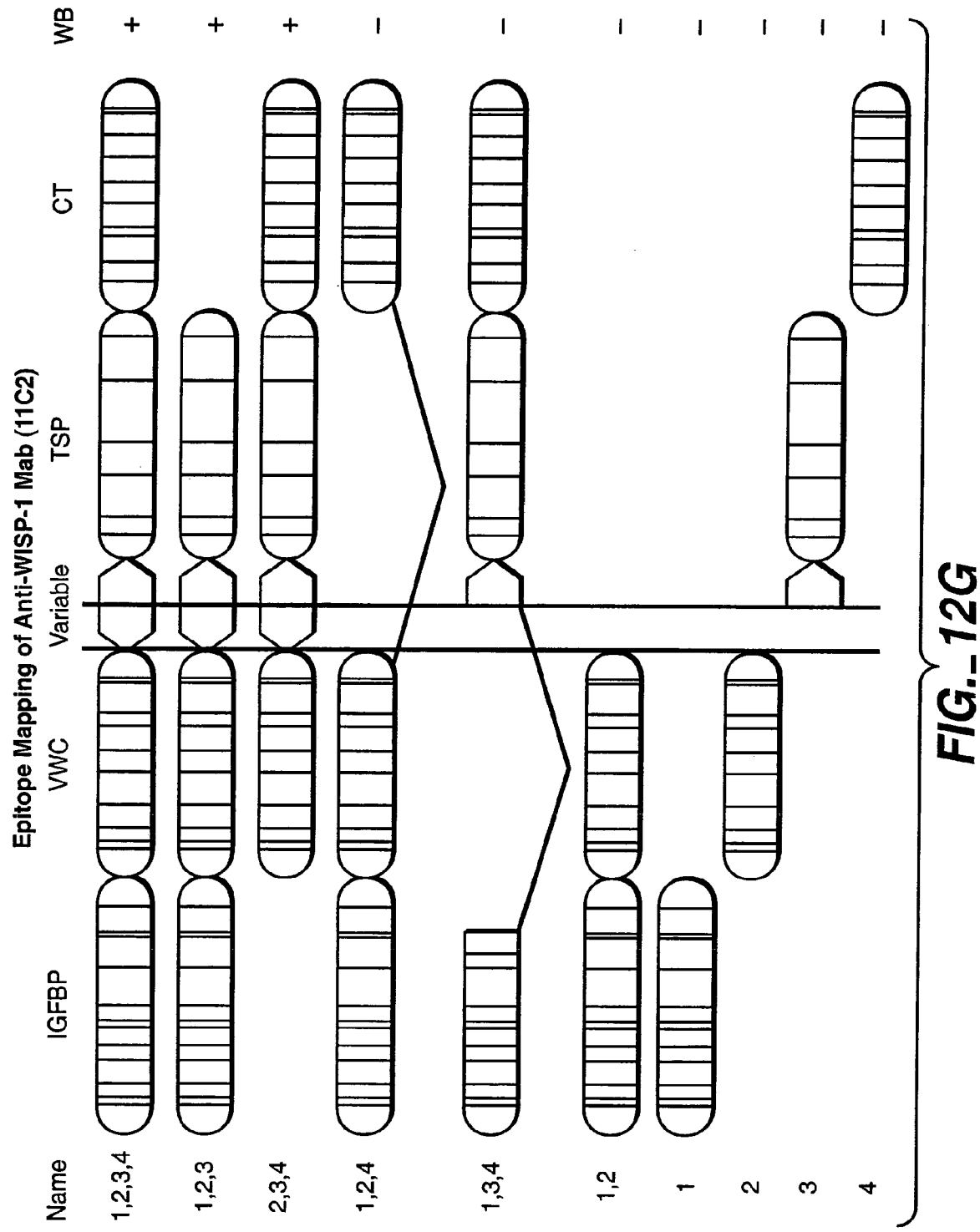
FIG._12G

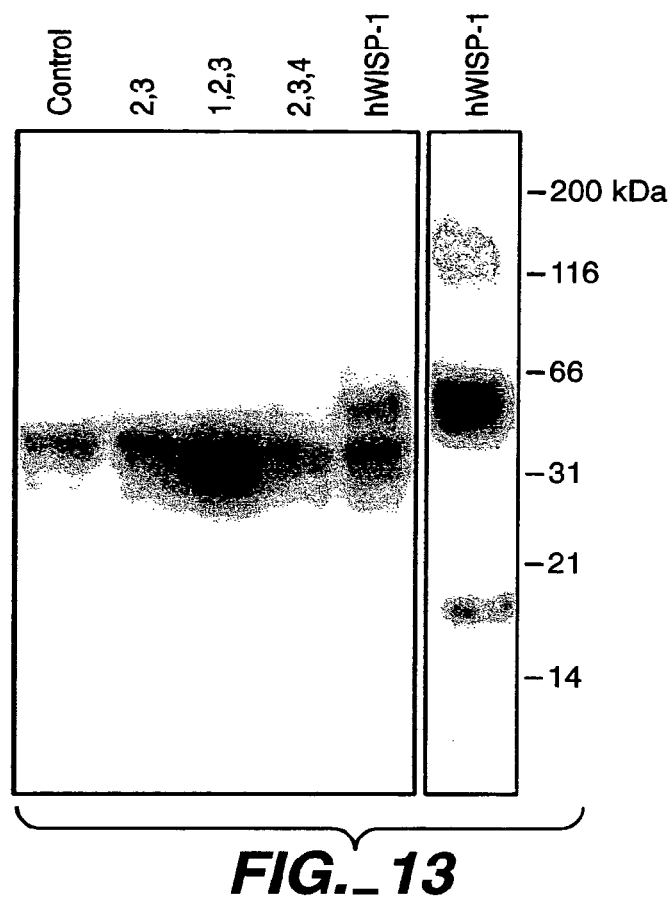
FIG._13
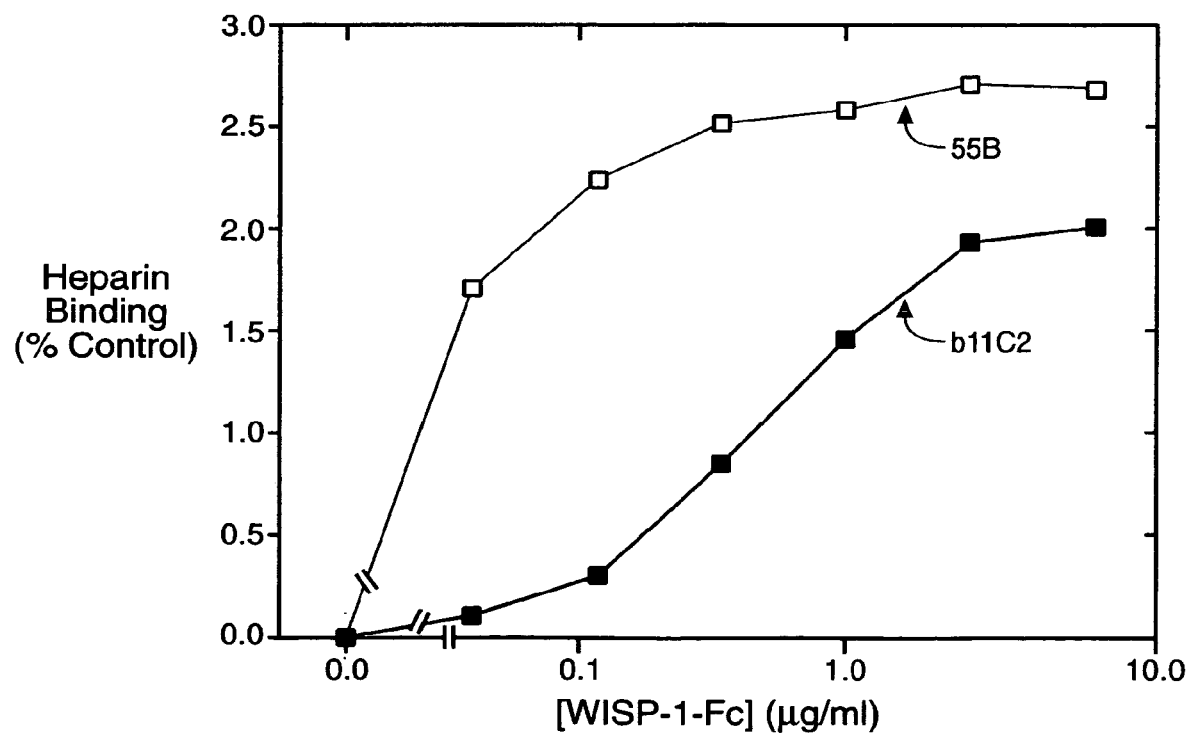
FIG._14

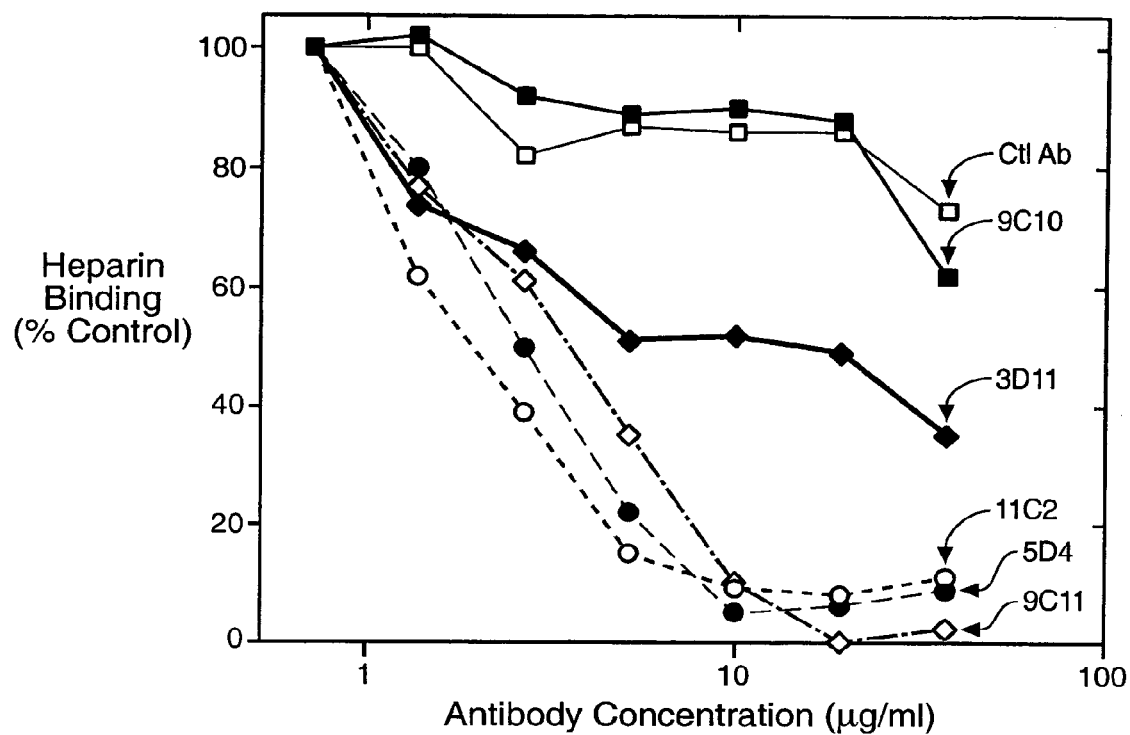
FIG._15
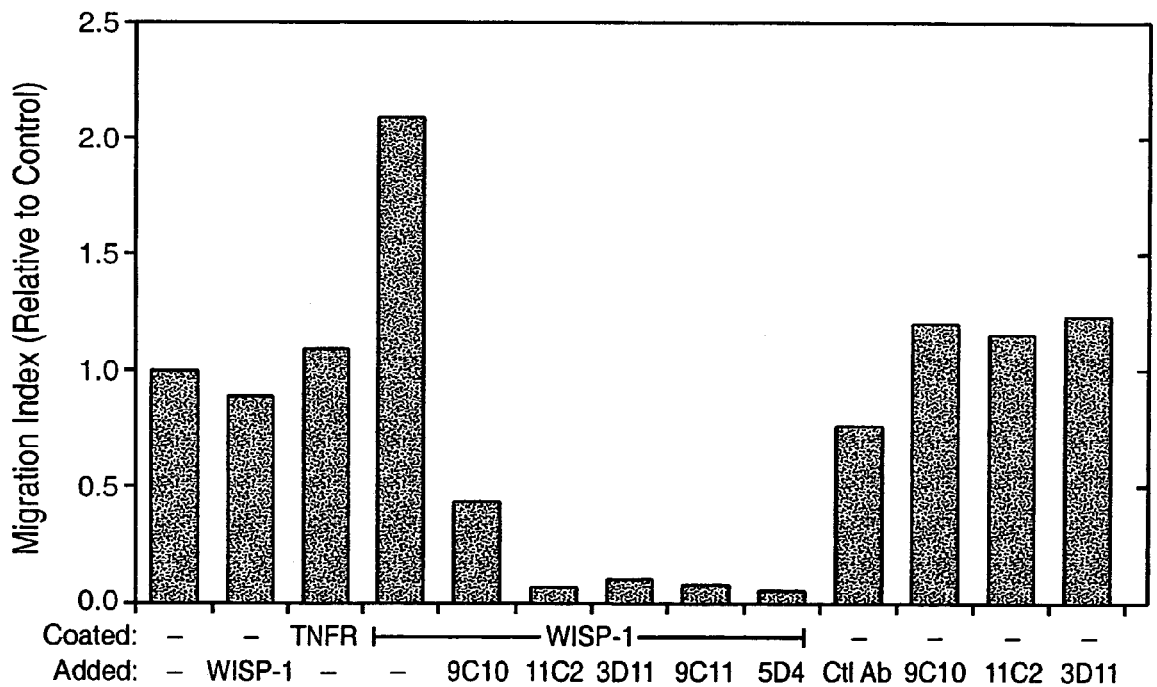
FIG._16A

| WISP-1 Antibodies Characterization | | | | | | | | |
|---|---|---|---|---|---|---|---|---|
| Clones | Isotype | Epitope | | IP | WB | Blocking Activity | | |
| | | Struct. | Cross Compet. | | | Heparin Binding | Cell Migrat. | Lung Met. |
| 3D11 | 2b | Domain 1 | A | − | + | +/− | + | + |
| 9C10 | 2b | Domain 1 | B | + | − | − | + | + |
| 11C2 | 2b | Variable Region | C | + | + | + | + | + |
| 5D4 | 2a | Variable Region | C | + | + | + | + | + |
| 9C11 | 2a | Variable Region | C | + | + | + | + | + |
*FIG. 16B*
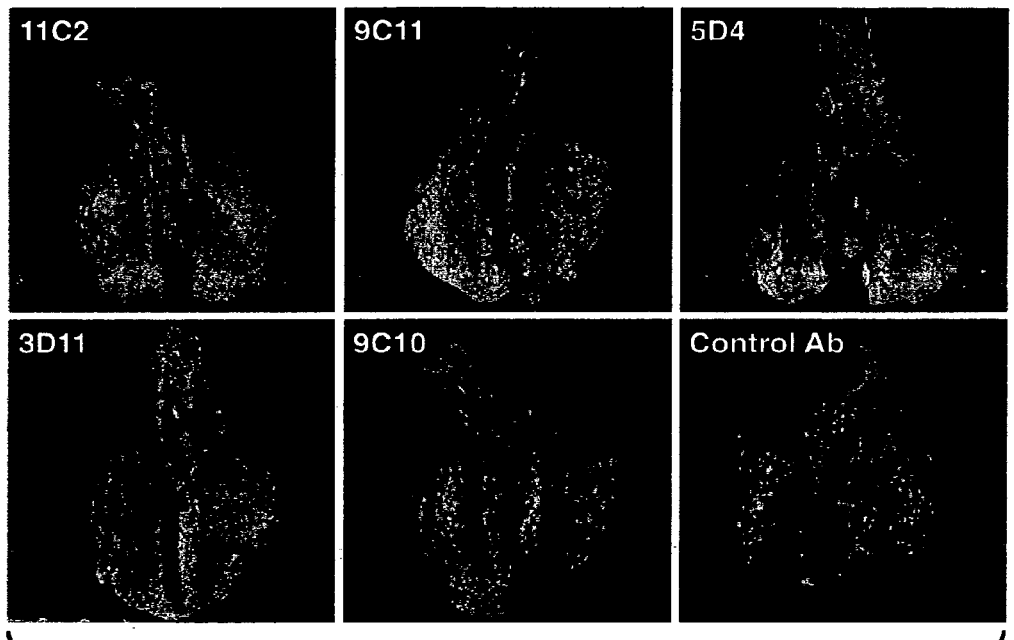
*FIG. 17A*
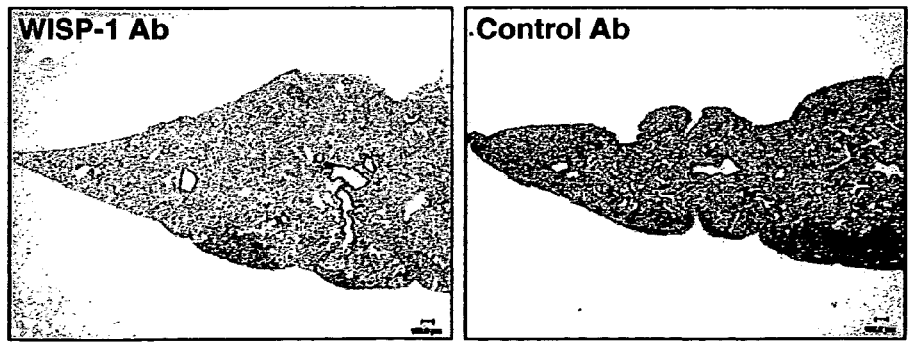
*FIG. 17B*

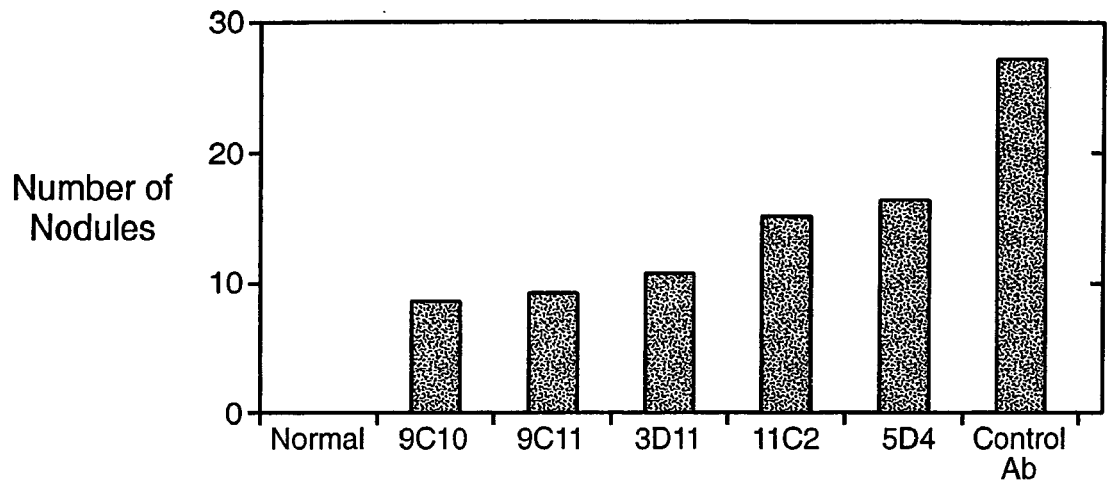
FIG._17C
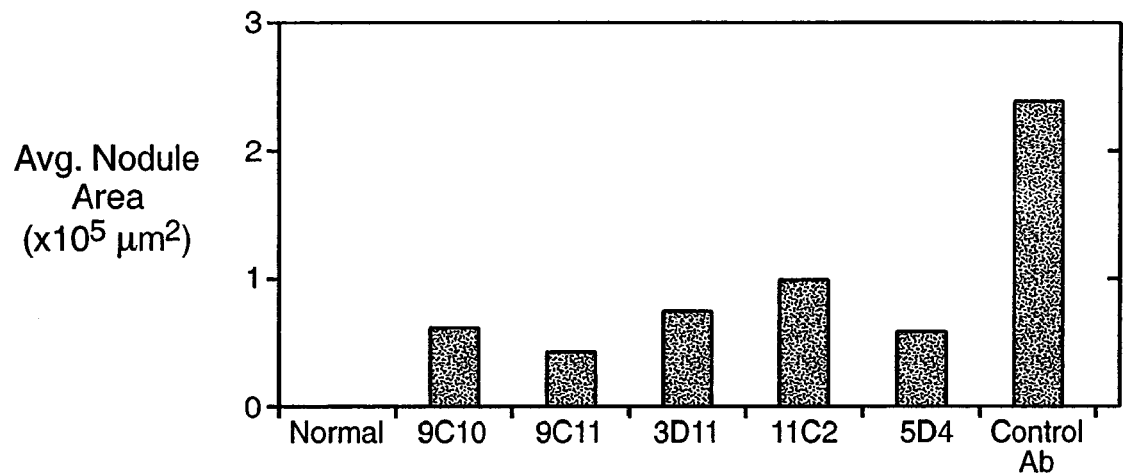
FIG._17D
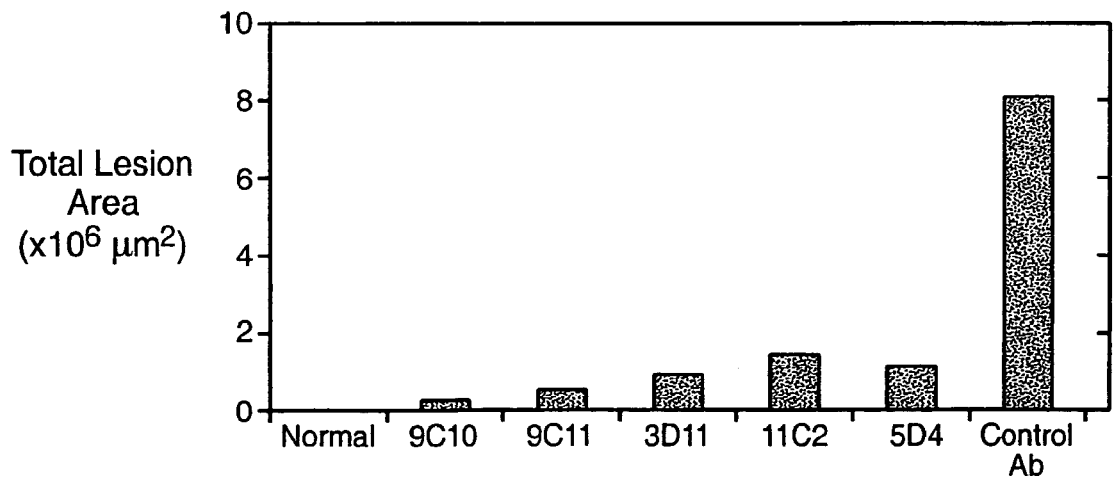
FIG._17E

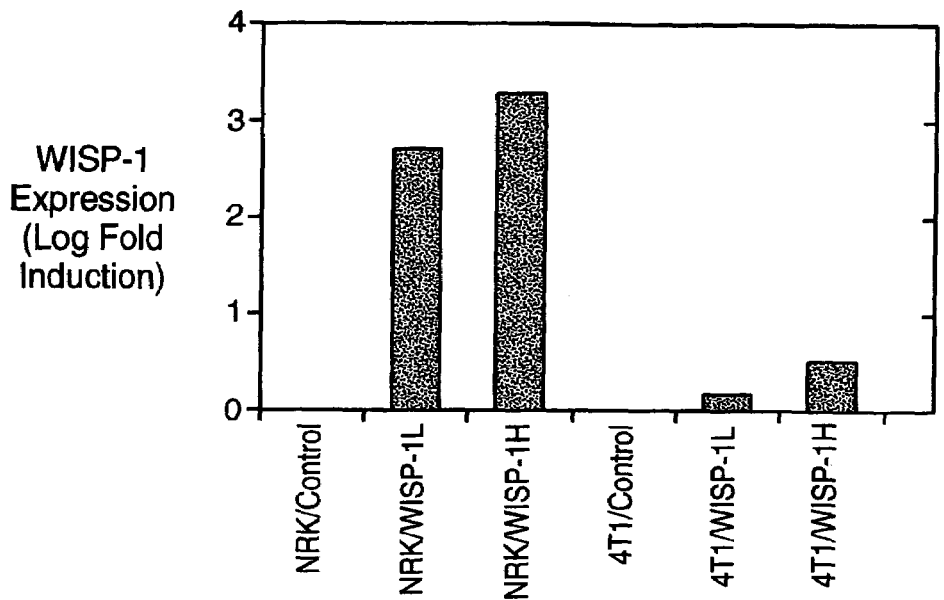
FIG._18
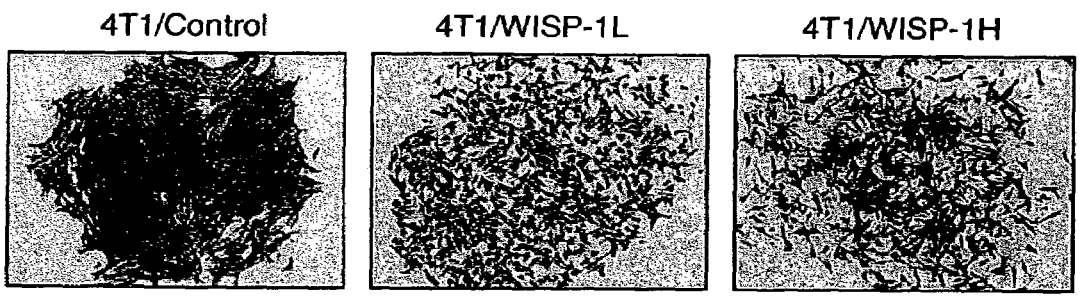
FIG._19
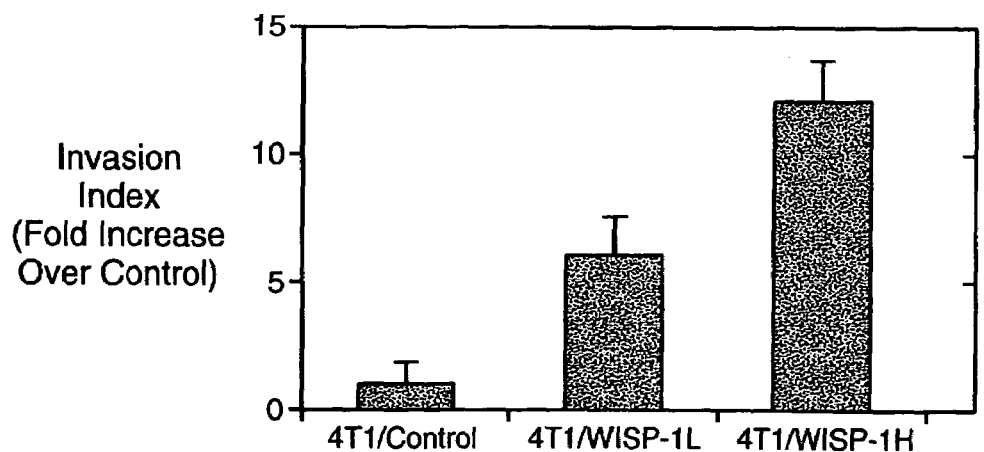
FIG._20

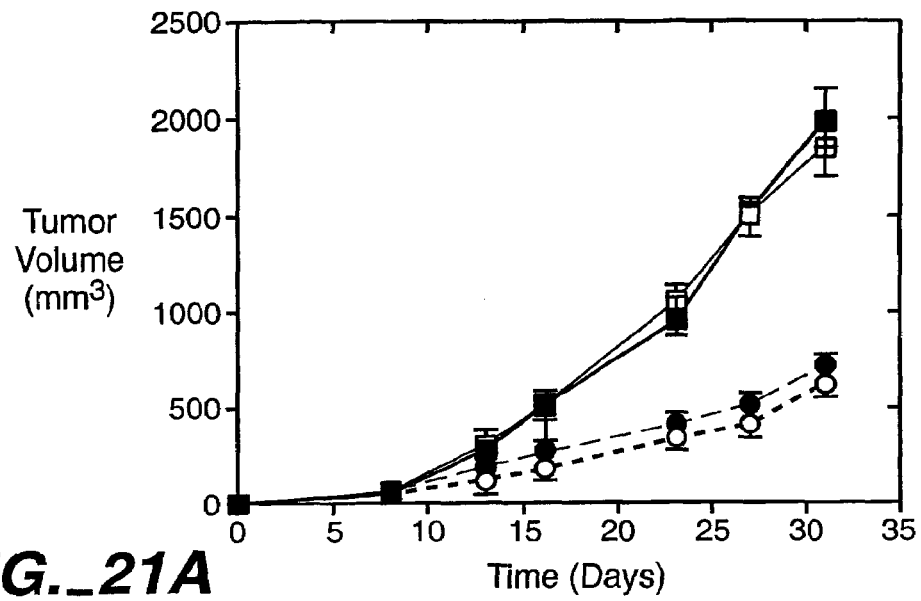
FIG._21A
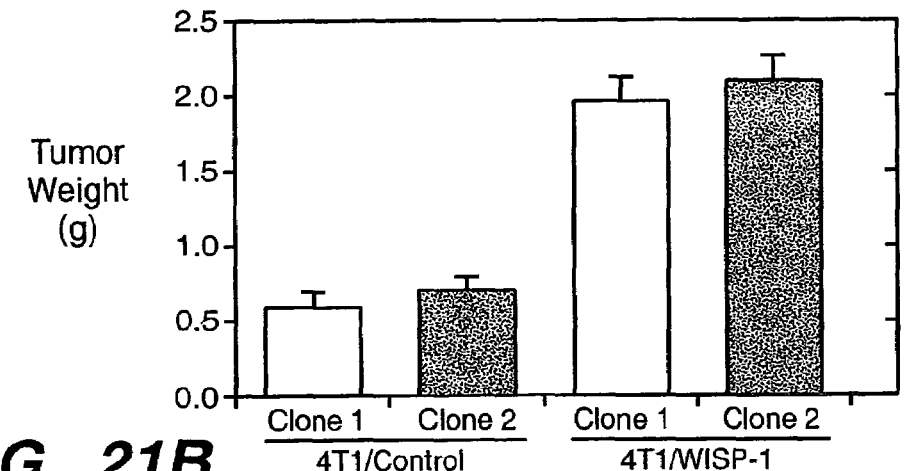
FIG._21B
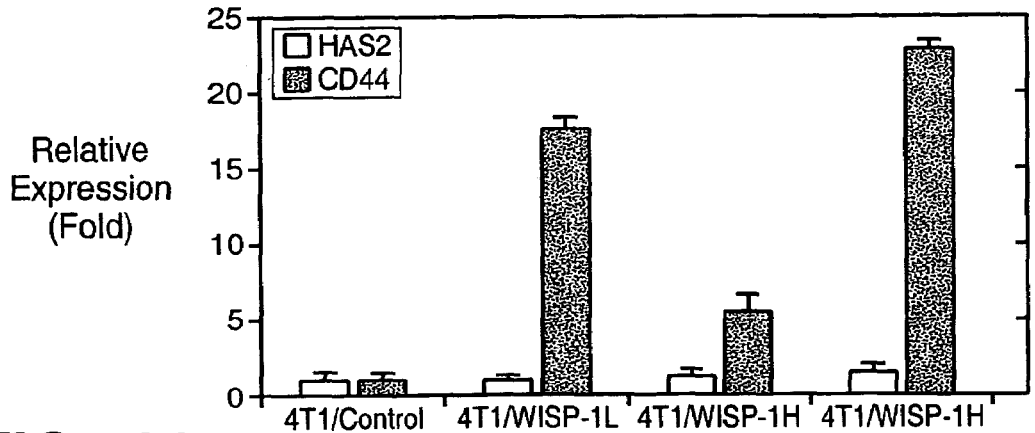
FIG._22

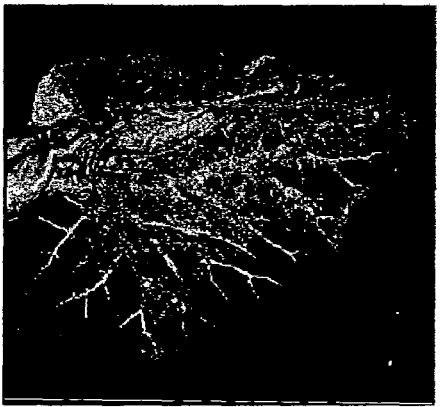
FIG._23A  FIG._23B  FIG._23C  FIG._23D  FIG._23E  FIG._23F

METHODS AND COMPOSITIONS FOR MODULATING AND DETECTING WISP ACTIVITY

RELATED APPLICATIONS

This application is a continuation application of U.S. application Ser. No. 11/105,876, filed Apr. 14, 2005 now U.S. Pat. No. 7,455,834, which is a continuation-in-part of U.S. application Ser. No. 10/519,621, filed Dec. 28, 2004 now U.S. Pat. No. 7,456,262, which is a 371 of International Application No. PCT/US03/020407, filed Jun. 28, 2003, which in turn claims priority under 35 U.S.C. 119(e) to U.S. Provisional Application No. 60/408,739, filed Sep. 6, 2002, and U.S. Provisional Application No. 60/392,652, filed Jun. 29, 2002, which applications are hereby incorporated by reference in their entirety.

FIELD OF THE INVENTION

The present invention relates generally to methods and compositions for use in modulating the activity(s) of WISP polypeptides, particularly, WISP-1 polypeptides. The invention also relates to methods and compositions for in vitro, in situ, and/or in vivo diagnosis and/or treatment of mammalian cells or pathological conditions associated with WISP polypeptides.

BACKGROUND OF THE INVENTION

Connective tissue growth factor (CTGF) is a growth factor induced in fibroblasts by many factors, including TGF-β, and is essential for the ability of TGF-β to induce anchorage-independent growth (AIG), a property of transformed cells. CTGF also is mitogenic and chemotactic for cells, and hence growth factors in this family are believed to play a role in the normal development, growth, and repair of human tissue. Five proteins related to CTGF, including Cyr61, Nov, WISP-1, WISP2, and WISP-3 have been isolated, cloned, sequenced, and characterized as belonging to the CCN gene family. Oemar and Luescher, *Arterioscler. Thromb. Vasc. Biol.*, 17: 1483-1489 (1997); Brigstock, *Endocrine Rev.*, 20:189-206 (1999). The gene encoding Cyr61 has been found to promote angiogenesis, tumor growth, and vascularization. Babic et al., *Proc. Natl. Acad. Sci. USA*, 95: 6355-6360 (1998). The nov gene is expressed in the kidney essentially at the embryonic stage, and alterations of nov expression, relative to the normal kidney, have been detected in both avian nephroblastomas and human Wilms' tumors. Martinerie et al., *Oncogene*, 9: 2729-2732 (1994). Wt1 downregulates human nov expression, which downregulation might represent a key element in normal and tumoral nephrogenesis. Martinerie et al., *Oncogene*, 12: 1479-1492 (1996).

The different members of the CCN family interact with various soluble or matrix associated macromolecules in particular sulfated glycoconjugates (Bork, *FEBS Letters*, 327: 125-130). This interaction was used to purify Cyr61 and CTGF by affinity chromatography on heparin-agarose (Frazier et al., *J. Invest. Dermatol.*, 107:404-411 (1996); Kireeva et al., *Mol. Cell. Biol.*, 16:1326-1334 (1996)). Cyr61 is secreted and associated with both the extracellular matrix and the cell surface due to its affinity for heparan sulfate (Yang et al., *Cell. Growth Diff.*, 2:351-357 (1991)). Recently, WISP-1 was shown to interact with decorin and biglycan, two secreted dermatan sulfate proteoglycans. (Desnoyers, et al., *J. Biol. Chem.*, 276:47599-47607 (2001)).

The murine protein ELM1 was recently identified in low metastatic cells. Hashimoto et al., *J. Exp. Med.*, 187:289-296 (1998). The elm1 gene, a mouse orthologue of WISP-1 disclosed below, is another member of the CNN gene family. It suppresses in vivo tumor growth and metastasis of K-1735 murine melanoma cells. Another recent article on rCop-1, the rat orthologue of WISP-2 described below, describes the loss of expression of this gene after cell transformation. Zhang et al., *Mol. Cell. Biol.*, 18:6131-6141 (1998).

Wnts are encoded by a large gene family whose members have been found in round worms, insects, cartilaginous fish, and vertebrates. Holland et al., *Dev. Suppl.*, 125-133 (1994). Wnts are thought to function in a variety of developmental and physiological processes since many diverse species have multiple conserved Wnt genes. McMahon, *Trends Genet.*, 8: 236-242 (1992); Nusse and Varmus, *Cell*, 69: 1073-1087 (1992). Wnt genes encode secreted glycoproteins that are thought to function as paracrine or autocrine signals active in several primitive cell types. McMahon, supra (1992); Nusse and Varmus, supra (1992). The Wnt growth factor family includes more than ten genes identified in the mouse (Wnt-1, -2, -3A, -3B, -4, -5A, -5B, -6, -7A, -7B, -8A, -8B, -10B, -11, -12, and -13) (see, e.g., Gavin et al., *Genes Dev.*, 4: 2319-2332 (1990); Lee et al., *Proc. Natl. Acad. Sci. USA*, 92: 2268-2272 (1995); Christiansen et al., *Mech. Dev.*, 51: 341-350 (1995)) and at least nine genes identified in the human (Wnt-1, -2, -3, -5A, -7A, -7B, -8B, -10B, and -11) by cDNA cloning. See, e.g., Vant Veer et al., *Mol. Cell. Biol.*, 4: 2532-2534 (1984).

The Wnt-1 proto-oncogene (int-1) was originally identified from mammary tumors induced by mouse mammary tumor virus (MMTV) due to an insertion of viral DNA sequence. Nusse and Varmus, *Cell*, 31: 99-109 (1982). In adult mice, the expression level of Wnt-1 mRNA is detected only in the testis during later stages of sperm development. Wnt-1 protein is about 42 KDa and contains an amino-terminal hydrophobic region, which may function as a signal sequence for secretion (Nusse and Varmus, supra, 1992). The expression of Wnt-2 is detected in mouse fetal and adult tissues and its distribution does not overlap with the expression pattern for Wnt-1. Wnt-3 is associated with mouse mammary tumorigenesis. The expression of Wnt-3 in mouse embryos is detected in the neural tubes and in the limb buds. Wnt-5a transcripts are detected in the developing fore- and hind limbs at 9.5 through 14.5 days and highest levels are concentrated in apical ectoderm at the distal tip of limbs. Nusse and Varmus, supra (1992). Recently, a Wnt growth factor, termed Wnt-x, was described (WO95/17416) along with the detection of Wnt-x expression in bone tissues and in bone-derived cells. Also described was the role of Wnt-x in the maintenance of mature osteoblasts and the use of the Wnt-x growth factor as a therapeutic agent or in the development of other therapeutic agents to treat bone-related diseases.

Wnts may play a role in local cell signaling. Peifer and Polakis, *Science*, 287:1606-1609 (2000). Biochemical studies have shown that much of the secreted Wnt protein can be found associated with the cell surface or extracellular matrix rather than freely diffusible in the medium. Papkoff and Schryver, *Mol. Cell. Biol.*, 10: 2723-2730 (1990); Bradley and Brown, *EMBO J.*, 9: 1569-1575 (1990).

Studies of mutations in Wnt genes have indicated a role for Wnts in growth control and tissue patterning. In *Drosophila*, wingless (wg) encodes a Wnt-related gene (Rijsewik et al., *Cell*, 50: 649-657 (1987)) and wg mutations alter the pattern of embryonic ectoderm, neurogenesis, and imaginal disc outgrowth. Morata and Lawerence, *Dev. Biol.*, 56: 227-240 (1977); Baker, *Dev. Biol.*, 125: 96-108 (1988); Klingensmith and Nusse, *Dev. Biol.*, 166: 396-414 (1994). In *Caenorhabditis elegans*, lin-44 encodes a Wnt homolog which is required for asymmetric cell divisions. Herman and Horvitz, *Development*, 120: 1035-1047 (1994). Knock-out mutations in mice have shown Wnts to be essential for brain development (McMahon and Bradley, *Cell*, 62: 1073-1085 (1990); Thomas and Cappechi, *Nature*, 346: 847-850 (1990)), and the outgrowth of embryonic primordia for kidney (Stark et al., *Nature*, 372: 679-683 (1994)), tail bud (Takada et al., *Genes Dev.*, 8: 174-189 (1994)), and limb bud. Parr and McMahon, *Nature*, 374: 350-353 (1995). Overexpression of Wnt-1 in the mammary gland can result in mammary hyperplasia (McMahon, supra (1992); Nusse and Varmus, supra (1992)), precocious alveolar development (Bradbury et al., *Dev. Biol.*, 170: 553-563 (1995)), and mammary adenocarcinomas (Li et al., *Oncogene*, 19:1002-1009 (2000)).

Wnt-5a and Wnt-5b are expressed in the posterior and lateral mesoderm and the extraembryonic mesoderm of the day 7-8 murine embryo. Gavin et al., supra (1990). These embryonic domains contribute to the AGM region and yolk sac tissues from which multipotent hematopoietic precursors and HSCs are derived. Dzierzak and Medvinsky, *Trends Genet.*, 11: 359-366 (1995); Zon et al., in Gluckman and Coulombel, ed., Colloque, *INSERM*, 235: 17-22 (1995), presented at the Joint International Workshop on Foetal and Neonatal Hematopoiesis and Mechanism of Bone Marrow Failure, Paris France, Apr. 3-6, 1995; Kanatsu and Nishikawa, *Development*, 122: 823-830 (1996). Wnt-5a, Wnt-10b, and other Wnts have been detected in limb buds, indicating possible roles in the development and patterning of the early bone microenvironment as shown for Wnt-7b. Gavin et al., supra (1990); Christiansen et al., *Mech. Devel.*, 51: 341-350 (1995); Parr and McMahon, supra (1995).

For a review on Wnt, see Cadigan and Nusse, *Genes & Dev.*, 11: 3286-3305 (1997).

Pennica et al., *Proc. Natl. Acad. Sci.*, 95:14717-14722 (1998) describe the cloning and characterization of two genes, WISP-1 and WISP-2, that are up-regulated in the mouse mammary epithelial cell line C57MG transformed by Wnt-1, and a third related gene, WISP-3. (See also, WO 99/21998 published May 6, 1999; WO 99/21999 published May 6, 1999). Pennica et al. report that these WISP genes may be downstream of Wnt-1 signaling and that aberrant levels of WISP expression in colon cancer may play a role in colon tumorigenesis. WISP-1 has recently been identified as a β-catenin-regulated gene and the characterization of its oncogenic activity demonstrated that WISP-1 might contribute to β-catenin-mediated tumorigenesis (Xu et al., *Gene & Develop.*, 14:585-595 (2000)). WISP-1 overexpression in normal rat kidney cells (NRK-49F) induced morphological transformation, accelerated cell growth and enhanced saturation density. In addition, these cells readily form tumors when injected into nude mice suggesting that WISP-1 may play some role in tumorigenesis (Xu et al., supra 2000). WISP-1 is also overexpressed in transformed human breast cancer cell lines and in about 47% of primary human breast cancer associated with certain advanced features. Xie et al., *Cancer Res.*, 61:8917-8923 (2001); Saxena et al., *Mol. Cell. Biochem.*, 228:99-104 (2001); Michaelson et al., *Oncogene*, 20:5093-5099 (2001). A particular WISP-1 variant has also been reported to be overexpressed in about 86% of human scirrhous gastric carcinoma cells. Tanaka et al., *Oncogene*, 20:5525-5532 (2001).

Hurvitz et al., *Nature Genetics*, 23:94-97 (1999) describe a study involving WISP3 in which nine different mutations of WISP3 in unrelated individuals were found to be associated with the autosomal recessive skeletal disorder, progressive pseudorheumatoid dysplasia (PPD). WISP3 expression by RT-PCR was observed by Hurvitz et al. in human synoviocytes, articular cartilage chondrocytes, and bone-marrow-derived mesenchymal progenitor cells.

PCT application WO98/21236 published May 22, 1998 discloses a human connective tissue growth factor gene-3 (CTGF-3) encoding a 26 kD member of the growth factor superfamily. WO98/21236 discloses that the CTGF-3 amino acid sequence was deduced from a human osteoblast cDNA clone, and that CTGF-3 was expressed in multiple tissues like ovary, testis, heart, lung, skeletal muscle, adrenal medulla, adrenal cortex, thymus, prostate, small intestine and colon.

Hyaluronic acid (also referred to as HA, hyaluronate, or hyaluronan) is recognized in the literature as being an important component of the extracellular matrix (See, e.g., Hardingham et al., *FASEB J.*, 6:861-870 (1992); Laurent et al., *FASEB J.*, 6:2397-2404 (1992)). HA is a component of skin and mesenchymal tissues where it facilitates cell migration during wound healing, inflammation, and embryonic morphogenesis. (Knudson et al., *FASEB J.*, 7:1233-1241 (1993); Knudson et al., *CIBA Found. Symp.*, 143:150-169 (1989)). HA has also been reported to play a role in certain types of metastases. (Naor et al., *CD44: Structure, Function and Association with the Malignant Process, Advances in Cancer Research*, Academic Press (1997), pages 241-319). The largest concentrations of HA are found in the skin and musculoskeletal system which account for over 50% of total body HA. (Banerji et al., *J. Cell Biol.*, 144:789-801 (1999)).

Various investigators have reported on receptors which bind HA. One of the receptors identified for HA is the CD44 protein. (See, e.g., Culty et al., *J. Cell Biology*, 111:2765-2774 (1990); Aruffo et al., *Cell*, 61:1303-1313 (1990); Naor et al., *CD44: Structure Function and Association with the Malignant Process, Advances in Cancer Research*, Academic Press (1997), pages 241-319); Ropponen et al., *Cancer Res.*, 58:342-347 (1998); Masaki et al., *Cancer*, 92:2539-2546 (2001). CD44 is a family of cell-surface glycoproteins generated from a single gene by alternative splicing and differential glycosylation. (Wielenga et al., *Am. J. Pathology*, 154: 515-523 (1999)). CD44 is believed to function as a cell adhesion receptor, linking extracellular molecules, specifically hyaluronate, to the cell and the cytoskeleton (Wielenga et al., supra). CD44 is expressed on epithelial, mesenchymal and lymphoid cells. (Lesley et al., *Adv. Immunol.*, 54:271-335 (1994)). Wielenga et al. report that CD44 expression may be regulated by the WNT pathway, based on certain experiments analyzing CD44 expression in the intestinal mucosa of mice and humans with genetic defects in either APC or Tcf-4. (Wielenga et al., supra).

Other HA receptors characterized to date include RHAMM (also referred to as receptor for hyaluronic acid mediated motility), a 58 kD intracellular protein expressed transiently on the surface of transformed lymphocytes (Hardwick et al., *J. Cell Biol.*, 117:1343-1350 (1992); Turley et al., *Exp. Cell Res.*, 207:277-282 (1993)). RHAMM expression in fibroblasts was reported to promote metastasis and play an important role in H-Ras transformation (Hall et al., infra).

Another receptor which binds HA was described by Banerji et al. (Banerji et al., supra). Banerji et al. report a receptor on lymph vessel walls, referred to as "LYVE-1", which is a 322-residue type I integral membrane polypeptide which has a 41% similarity to the CD44 receptor. Unlike the CD44 receptor for HA, the LYVE-1 protein is absent in blood vessels. In addition, layilin (Bono et al., *Mol. Biol. Cell*, 12:891-900 (2001)) and HARE (Zhou et al., *J. Biol. Chem.*, 275: 37733-37741 (2000)) were also described as HA receptors.

SUMMARY OF THE INVENTION

Applicant has surprisingly found that WISP-1 can induce HAS2 (hyaluronan synthase 2), CD44, and RHAMM mRNA expression, CD44 protein synthesis, and HA secretion. The induction or secretion of such molecules may promote or increase cancer cell growth, motility and/or metastatic potential. The present invention thus provides for instance, WISP-1 antagonists and methods of using such antagonists. The antagonists described herein find utility for, among other things, in vitro, in situ, or in vivo diagnosis or treatment of mammalian cancer cells or other pathological conditions associated with the induction or secretion of HAS2, HA, CD44 or RHAMM.

In embodiments of the invention, there are provided isolated WISP-1 antagonists. Such antagonists may comprise antibodies, such as WISP-1 antibodies. In preferred embodiments, the antagonists may block or neutralize WISP-1 induction or secretion of HAS2, HA, CD44 or RHAMM. Such antagonistic antibodies may, for example, be monoclonal antibodies, chimeric antibodies, humanized antibodies, or human antibodies. The WISP-1 antagonists contemplated for use in the invention include WISP-1 immunoadhesins, WISP-1 variants, covalently modified forms thereof, or fusion proteins thereof. By way of example, such antagonists may include pegylated WISP-1 or WISP-1 fused to heterologous sequences such as epitope tags or leucine zippers. The methods contemplate the use of a single type of antagonist molecule or a combination of two or more types of antagonists.

The methods of the invention include methods to treat pathological conditions or diseases in mammals associated with or resulting from WISP-1, including, induction or secretion of HAS2, HA, CD44 or RHAMM by WISP-1. In the methods of treatment, WISP-1 antagonists may be administered to the mammal suffering from such pathological condition or disease. For example, the invention provides a method comprising exposing a mammalian cell(s), such as a cancer cell(s), to one or more WISP-1 antagonists in an amount effective to decrease, neutralize or block WISP-1 induction or secretion of HAS2, HA, CD44 or RHAMM. The cell may be in cell culture or in a mammal, e.g. a mammal suffering from, for instance, cancer.

The invention also provides compositions which comprise one or more WISP-1 antagonists. Optionally, the compositions of the invention will include pharmaceutically acceptable carriers or diluents. Preferably, the compositions will include one or more WISP-1 antagonists in an amount which is therapeutically effective to treat a pathological condition or disease.

The invention also provides articles of manufacture and kits which include one or more WISP-1 antagonists.

The invention also provides methods of conducting screening assays to identify candidate molecules, such as small molecule compounds, polypeptides or antibodies, which act as antagonists with respect to blocking or neutralizing WISP-1 induction or secretion of HAS2, HA, CD44 or RHAMM.

More particular embodiments of the invention include isolated WISP-1 antagonists which inhibit or neutralize the induction or secretion of HAS2, HA, CD44 or RHAMM by native WISP-1 polypeptide in at least one type of mammalian cell, said antagonist being selected from the group consisting of an anti-WISP-1 antibody, a WISP-1 immunoadhesin, a WISP-1 variant, and fusion proteins thereof. The antagonist may comprise an anti-WISP-1 antibody which binds native human WISP-1 polypeptide comprising amino acids 23-367 of FIGS. 9A-9C or one or more domains of WISP-1 comprising amino acids encoded by the sequences of SEQ ID NO:3; 4; 5; 6; 7; 8; 9; 10; or 11 herein. The anti-WISP-1 antibody may be a chimeric, humanized or human antibody.

The invention also provides compositions comprising the antagonists described herein and a carrier, optionally the carrier is a pharmaceutically-acceptable carrier.

The invention also provides methods of inhibiting or neutralizing WISP-1 induction or secretion of HAS2, HA, CD44 or RHAMM in mammalian cells, comprising exposing said mammalian cells to an effective amount of WISP-1 antagonist, wherein said WISP-1 antagonist is selected from the group consisting of a) a WISP-1 immunoadhesin;
b) a WISP-1 polypeptide linked to a nonproteinaceous polymer selected from the group consisting of polyethylene glycol, polypropylene glycol, and polyoxyalkylene;
c) a WISP-1 antibody; and
d) a WISP-1 variant.

The WISP-1 immunoadhesins employed in the methods may comprise a WISP-1 sequence fused to a Fc region of an immunoglobulin. The anti-WISP-1 antibodies employed in the methods may bind native human WISP-1 comprising amino acids 23-367 of FIGS. 9A-9C, or one or more of the domains of WISP-1 described in the Examples below. In the methods, the mammalian cells may comprise cancer cells, and optionally the cells comprise colon or colorectal cancer cells, breast cancer cells, lung cancer cells, or brain cancer cells (such as glioma or glioblastoma).

In other embodiments, there are provided methods of treating cancer in a mammal, comprising administering to said mammal an effective amount of WISP-1 antagonist. Optionally, in said methods, the antagonist may inhibit or neutralize induction or secretion of HAS2, HA, CD44 or RHAMM by native human WISP-1 polypeptide in at least one type of mammalian cell and said antagonist is selected from the group consisting of an anti-WISP-1 antibody, a WISP-1 immunoadhesin and a WISP-1 variant. Optionally, the antagonist may act to inhibit cancer cell growth or cancer cell metastasis. The cancer in the mammal may comprise colon or colorectal cancer cells, breast cancer cells, lung cancer cells, or brain cancer cells (such as glioma or glioblastoma). Optionally, the antagonist(s) employed in the methods inhibits or reduces cancer cell growth or metastasis. Also, in the methods, chemotherapy, radiation, prodrug, cytotoxic agent, growth inhibitory agent, or cytokine may also be administered to the mammal.

In more particular embodiments, there are provided antibodies which specifically bind to one or more domains of WISP-1 polypeptide (described further in the Examples below) comprising amino acids encoded by the sequences of SEQ ID NO:3; 4; 5; 6; 7; 8; 9; 10; or 11 herein. Optionally, the antibody is a monoclonal antibody. Optionally, the monoclonal antibody comprises the 3-D11, 11C2, 9C10, 5D4, or 9C11 antibody secreted by the hybridoma deposited with ATCC as accession number PTA-4624, PTA-4628, PTA-4626, PTA-4625, or PTA-4627, respectively.

Also provided are antibodies which bind to the same epitope as the epitope to which the 3D11, 11C2, 9C10C, 5D4, or 9C11 monoclonal antibody produced by the hybridoma cell line deposited as ATCC accession number PTA-4624, PTA-4628, PTA-4626, PTA-4625, or PTA-4627, respectively, binds.

In yet other particular embodiments, there is provided the hybridoma cell line which produces monoclonal antibody 3-D11, 11C2, 9C10C, 5D4, or 9C11 and deposited with ATCC as accession number PTA-4624, PTA-4628, PTA-4626, PTA-4625, or PTA-4627, respectively, and the monoclonal antibody 3-D11, 11C2, 9C10C, 5D4, or 9C11 secreted by the hybridoma deposited with ATCC as accession number PTA-4624, PTA-4628, PTA-4626, PTA-4625, or PTA-4627, respectively.

There are also provided isolated anti-WISP-1 monoclonal antibodies, comprising antibodies which bind to WISP-1 polypeptide and competitively inhibit binding of the monoclonal antibody produced by the hybridoma deposited as ATCC accession no. PTA-4624, PTA-4628, PTA-4626, PTA-4625, or PTA-4627 to said WISP-1 polypeptide.

There are also provided chimeric or humanized anti-WISP-1 antibodies which specifically bind to WISP-1 polypeptide and comprise (a) a sequence derived from the 3D11, 11C2, 9C10, 5D4, or 9C11 antibody secreted by the hybridoma deposited with ATCC as accession number PTA-4624, PTA-4628, PTA-4626, PTA-4625, or PTA-4627, respectively. Optionally, such antibodies may comprise a heavy chain, light chain or variable regions derived from the 3-D11, 11C2, 9C10, 5D4, or 9C11 antibody.

The anti-WISP-1 antibodies may be linked to one or more non-proteinaceous polymers selected from the group consisting of polyethylene glycol, polypropylene glycol, and polyoxyalkylene, or to a cytotoxic agent or enzyme, or to a radioisotope, fluorescent compound or chemiluminescent compound.

BRIEF DESCRIPTION OF THE DRAWINGS

FIGS. 1A-1F show WISP-1 promotion of hyaluronan production. Particle exclusion assay demonstrating a hyaluronan coat at the surface of NRK/WISP-1H (A) and NRK/WISP-1L (B) but absent from NRK/control (C). NRK/WISP-1H (D) and NRK/control (E) were stained for hyaluronan with bHABP. F, Time course of HA accumulation in NRK/WISP-1H and NRK/control media.

FIGS. 2A-2C show WISP-1 increases HAS2, CD44 and RHAMM mRNA expression and CD44 protein expression. A, Real time RT-PCR analysis of HAS1, HAS2, HAS3, CD44, RHAMM and hyaluronidase (Hyal) mRNA expression in NRK/WISP-1H, NRK/WISP-1L and NRK/control cells. Results are given as fold induction over the expression in NRK/control cells. B, Flow cytometry analysis of CD44 expression in NRK/WISP-1H and NRK/control cells. The shaded area represents the fluorescence intensity of the secondary antibody alone. C, Western blot analysis of CD44 protein in NRK/WISP-1H and NRK/control cells. Actin staining was used as a loading control.

FIGS. 3A-3G show WISP-1 expression increases cell motility and modifies cellular morphology. NRK/control cells (A) formed defined colonies when plated at low density whereas NRK/WISP-1L (B) and NRK/WISP-1H cells (C) scattered. NRK/WISP-1H (E) showed a de-differentiated spindloid morphology with lamelipodia compared to NRK/control cells (D). F, The random migration of NRK/WISP-1H and NRK/control cells was measured over 15 hours using time lapse microscopy. Results represent the typical average migration distance of cells in one field. G, Motility of NRK/WISP-1H and NRK/control cells was evaluated by a cell wound healing assay and measured after 15 hours using time lapse microscopy. Data represent the results of a typical experiment.

FIGS. 4A-4C show WISP-1 addition induces HAS2 mRNA expression and haptotactic migration of NRK cells. A, Real time RT-PCR analysis of HAS2 and CD44 expression in NRK cells seeded on coated surface. In certain cases the coated substrates were further incubated with WISP-1 (treatment). Results are given in fold induction over expression in NRK cells plated on non-coated, non-treated surface. The underside of modified Boyden chamber filters were coated and NRK cells (B) or SW480 cells (C) were added to the upper chamber. In certain cases, additions were made directly to the lower chamber. Cell motility was evaluated by counting the cells that migrated to the lower side of the insert.

FIGS. 5A-5E show WISP-1, HAS2 and CD44 over-expression and increased cell motility in C57MG/Wnt-1 cells and MMTV-Wnt-1 transgenic mice mammary tumors. A, Real time RT-PCR analysis of WISP-1, HAS2 and CD44 expression in C57MG/Wnt-1 and C57MG/control cells. Results are given as fold induction over expression in C57MG/control cells. B, Western blot analysis of CD44 content in C57MG/Wnt-1 and C57MG/control cells. Actin staining was used as a loading control. C, C57MG/control cells formed distinct colonies when plated at low density whereas C57MG/Wnt-1 cells scattered. Semi-quantitative RT-PCR analysis of HAS2 (D) and CD44 (E) in mammary tumors of MMTV-Wnt-1 transgenic mice. Results are expressed as relative fold induction over the expression in normal mammary gland tissue.

FIGS. 6A-6H show WISP-1, HAS2 and CD44 expression and HA accumulation in MMTV-Wnt-1 transgenic mammary tumors. In situ hybridization of WISP-1 (A, B) HAS2 (C, D) and CD44 (E, F), immunohistochemistry of CD44 (G) and bHABP fluorescent staining of hyaluronan (H) in MMTV-Wnt-1 transgenic mouse mammary tumors. t, tumor; s, stroma.

FIGS. 7A-7L show WISP-1 expression promotes metastatic lung colonization and tumor growth. The effect of WISP-1 was analyzed by injecting NRK/control, NRK/WISP-1L or NRK/WISP-1H cells in the tail vein of nude mice. At various times after injection, lungs were imaged by MRI (A, D, G, J), excised and their gross appearance (B, E, H, K) and histological features (C, F, I, L) were recorded. The severity of lung invasion by tumors was graded as normal (A, B, C); grade I (D, E, F); grade II (G, H, I) or grade III (J, K, L).

FIGS. 8A-B show CD44 antibody prevents NRK/WISP-1H cell metastasis. NRK/WISP-1H cells ($2.5 \times 10^5$ cells) were injected in the tail vein of nude mice. Mice were treated twice a week with 10 mg/kg of a CD44 antibody, an isotype control antibody or with buffer only (PBS). The lungs were excised after four weeks for gross anatomical analysis. Picture of a normal lung is shown for comparison.

FIGS. 9A-9C show the nucleotide (SEQ ID NO:2) and putative amino acid sequence (SEQ ID NO:1) of native human WISP-1.

FIG. 10 shows the effects of WISP-1 expression on NRK metastatic potential.

FIGS. 11A-B show the binding properties of WISP-1 antibodies to various WISP-1 constructs and preparations.

FIGS. 12A-G show diagrams of various domains of WISP-1 polypeptide and the results of assays conducted to identify the epitopes recognized by the WISP-1 antibodies 11C2, 5D4, 9C11, and 3D11, respectively. FIG. 12C illustrates the amino acid sequence provided in SEQ ID NO: 20.

FIG. 13 shows the results on an assay conducted to identify the epitope recognized by the WISP-1 antibody 9C10.

FIG. 14 shows the results of an ELISA demonstrating detection of WISP-1 by WISP-1 antibodies.

FIG. 15 shows the results of an ELISA binding assay demonstrating that WISP-1 antibodies recognizing the variable region of WISP-1 can inhibit WISP-1 binding to heparin.

FIGS. 16A-B show the results of an assay detecting inhibition of haptotaxis of NRK cells by WISP-1 antibodies (16A) and a chart summarizing the properties and characteristics of WISP-1 antibodies (16B).

FIGS. 17A-E show the results of an in vivo study of the effects of WISP-1 antibodies. After 3 weeks, the severity of the lesions found in WISP-1 antibody treated animals was greatly attenuated compared to control (FIG. 17 a, b). The number of nodules and the average area of the metastatic foci found in mice treated with WISP-1 antibodies (n=5) were reduced compared to animals treated with a control antibody (FIGS. 17 c,d). The total pulmonary area covered by the lesions was reduced by 82-97% compared to animal treated with an isotype control antibody (FIG. 17e).

FIG. 18 is a bar diagram showing expression of WISP-1 in 4T1/control, 4T1/WISP-1L, 4T1/WISP-1H, NRK/control, NRK/WISP-1L, and WISP-1H cell lines as measured by semi-quantitative RT-PCR (Taqman).

FIG. 19 shows the results of an in vitro assay on colony formation of 4T1/control, 4T1/WISP-1L, and 4T1/WISP-1H cell lines.

FIG. 20 shows the results of an in vitro assay measuring invasion index using a Matrigel modified Boyden chamber system and 4T1/control, 4T1/WISP-1L, and 4T1/WISP-1H cell lines.

FIGS. 21A-B show effects of WISP-1 expression on mammary epithelial cell tumorigenesis. The effect of WISP-1 was analyzed by injecting 4T1/control 1, 4T1/control 2, 4T1/WISP-1L or 4T1/WISP-1H cells in Balb/C mice. Tumor volume (21A) and tumor weight (21 B) are reported.

FIG. 22 is a bar diagram illustrating the relative expression of HAS2 and CD44 in tumors formed by the inoculated 4T1/control, 4T1/WISP-1L and 4T1/WISP-1H cells.

FIGS. 23A-F illustrate the WISP-1 effects on mammary epithelial cells metastasis evaluated in vivo by inoculating 4T1 cells in mice mammary fat pads and examining the extent of the metastatic propagation by micro computer tomography and histology. After 31 days, the mice inoculated with 4T1/WISP-1L or 4T1/WISP-1H cells had extensive lung metastasis (FIGS. 23b and 23d) compared to the 4T1/control injected mice (FIGS. 23a and 23c). Using immunohistochemistry, it was also observed that the 4T1/WISP-1 pulmonary metastatic foci expressed high levels of CD44 (FIG. 23e). In these tumors, CD44 was localized at the plasma membrane of the 4T1/WISP-1 cells (FIG. 23f).

DETAILED DESCRIPTION OF THE INVENTION

I. Definitions

Figure 24:
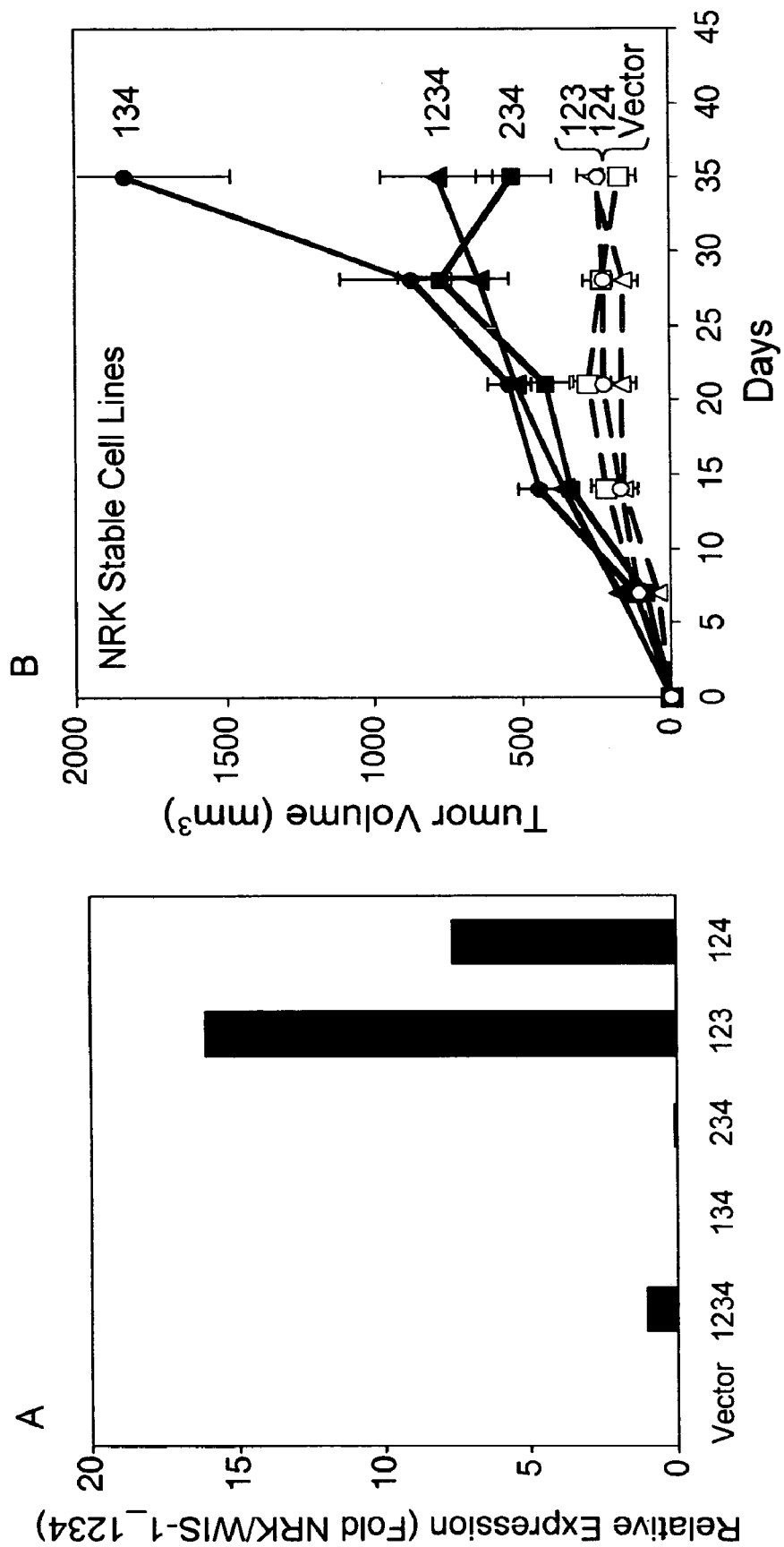
FIG. 24A shows WISP-1 expression in NRK/control, NRK/WISP-1_1234, NRK/WISP-1_134, NRK/WISP-1_234, NRK/WISP-1_123 and NRK/WISP-1_124 cells lines, as measured by semi-quantitative RT-PCR (Taqman); the results are expressed as fold relative to WISP-1 expression in NRK/WISP-1_1234.
FIG. 24B illustrates the effects of these constructs on tumorigenesis in vivo; the results are shown by the effects on tumor volume.

The term "WISP polypeptide" refers to the family of native-sequence human and mouse WISP proteins and variants described herein whose genes are induced at least by Wnt-1. This term includes WISP-1 and variants thereof. Such WISP-1 proteins are described further below and in PCT application WO99/21998 published May 6, 1999, U.S. Pat. No. 6,387,657 B1 issued May 14, 2002, and in Pennica et al., *Proc. Natl. Acad. Sci.*, 95:14717-14722 (1998).

The terms "WISP-1 polypeptide", "WISP-1 homologue" and grammatical variants thereof, as used herein, encompass native-sequence WISP-1 protein and variants (which are further defined herein). The WISP-1 polypeptide may be isolated from a variety of sources, such as from human tissue types or from another source, or prepared by recombinant or synthetic methods, or by any combination of these and similar techniques.

The term "native-sequence WISP-1 polypeptide" comprises a polypeptide having the same amino acid sequence as a WISP-1 polypeptide derived from nature. Such native-sequence WISP-1 polypeptides can be isolated from nature or can be produced by recombinant or synthetic means. The term "native-sequence WISP-1 polypeptide" specifically encompasses naturally occurring truncated or secreted forms of a WISP-1 polypeptide disclosed herein, naturally occurring variant forms (e.g., alternatively spliced forms or splice variants), and naturally occurring allelic variants of a WISP-1 polypeptide. In one embodiment of the invention, the native-sequence WISP-1 polypeptide is a mature or full-length native-sequence human WISP-1 polypeptide comprising amino acids 23 to 367 of FIG. 9 or amino acids 1 to 367 of FIG. 9, respectively, with or without N-terminal methionine.

In another embodiment of the invention, the native-sequence WISP-1 polypeptide is the full-length or mature native-sequence human WISP-1 polypeptide comprising amino acids 23 to 367 or 1 to 367 of FIG. 9 wherein the valine residue at position 184 or the alanine residue at position 202 has/have been changed to an isoleucine or serine residue, respectively, with or without N-terminal methionine. In another embodiment of the invention, the native-sequence WISP-1 polypeptide is the full-length or mature native-sequence human WISP-1 polypeptide comprising amino acids 23 to 367 or 1 to 367 of the FIG. 9 wherein the valine residue at position 184 and the alanine residue at position 202 has/have been changed to an isoleucine or serine residue, respectively, with or without N-terminal methionine.

In another embodiment of the invention, the native-sequence WISP-1 polypeptide is one which is encoded by a nucleotide sequence comprising one of the human WISP-1 splice or other native-sequence variants, including SEQ ID NOS:23, 24, 25, 26, 27, 28, or 29 shown in WO99/21998, with or without an N-terminal methionine.

The term "WISP-1 variant" means an active WISP-1 polypeptide as defined below having at least about 80%, preferably at least about 85%, 86%, 87%, 88%, 89%, more preferably at least about 90%, 91%, 92%, 93%, 94%, most preferably at least about 95%, 96%, 97%, 98%, or 99% amino acid sequence identity with human mature WISP-1 having the deduced amino acid sequence shown in FIG. 9, or a soluble fragment thereof. Such variants include, for instance, WISP-1 polypeptides wherein one or more amino acid residues are added to, or deleted from, the N- or C-terminus of the full-length or mature sequences of FIG. 9, or WISP-1 polypeptides wherein one or more amino acid residues are inserted or deleted from the internal sequence or domains of the polypeptide, including variants from other species, but excludes a native-sequence WISP-1 polypeptide. Preferably such a variant acts as an antagonist, as defined below.

An "extracellular domain", "ECD" or "secreted" protein refers to a form of a polypeptide which is essentially free of any transmembrane and cytoplasmic domains. A "secreted" form of a protein or polypeptide may or may not include a signal sequence.

"Stringent conditions" are those that (1) employ low ionic strength and high temperature for washing, for example, 0.015 M sodium chloride/0.0015 M sodium citrate/0.1% sodium dodecyl sulfate at 50° C.; (2) employ during hybridization a denaturing agent, such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS; or (4) employ a buffer of 10% dextran sulfate, 2×SSC (sodium chloride/sodium citrate), and 50% formamide at 55° C., followed by a high-stringency wash consisting of 0.1×SSC containing EDTA at 55° C.

"Moderately stringent conditions" are described in Sambrook et al., *Molecular Cloning: A Laboratory Manual* (New York: Cold Spring Harbor Laboratory Press, 1989), and include the use of a washing solution and hybridization conditions (e.g., temperature, ionic strength, and percent SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc., as necessary to accommodate factors such as probe length and the like.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the WISP natural environment will not be present. Ordinarily, however, isolated polypeptide will be prepared by at least one purification step.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "liposome" is a small vesicle composed of various types of lipids, phospholipids and/or surfactant which is useful for delivery of a drug (such as the insulin and insulin variants disclosed herein) to a mammal. The components of the liposome are commonly arranged in a bilayer formation, similar to the lipid arrangement of biological membranes.

The terms "amino acid" and "amino acids" refer to all naturally occurring L-alpha-amino acids. This definition is meant to include norleucine, ornithine, and homocysteine. The amino acids are identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

In the Sequence Listing and Figures, certain other single-letter or three-letter designations may be employed to refer to and identify two or more amino acids or nucleotides at a given position in the sequence.

"Percent (%) amino acid sequence identity" with respect to the polypeptide sequences identified herein is defined as the percentage of amino acid residues in a candidate sequence that are identical with the amino acid residues in such a polypeptide sequence identified herein, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program is provided in the table below. The ALIGN-2 sequence comparison computer program was authored by Genentech, Inc. and the source code shown in the table below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in the table below. The ALIGN-2 program should be compiled for use on a UNIX operating system, preferably digital UNIX V4.0D. All sequence comparison parameters are set by the ALIGN-2 program and do not vary.

The term "epitope tagged" when used herein refers to a chimeric polypeptide comprising a polypeptide fused to a "tag polypeptide". The tag polypeptide has enough residues to provide an epitope against which an antibody can be made. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The term "antagonist" is used in the broadest sense, and includes any molecule that partially or fully blocks, inhibits, or neutralizes one or more biological activities of WISP-1 polypeptide, in vitro, in situ, or in vivo. Examples of such biological activities of WISP-1 polypeptides include induction or secretion of HAS2, HA, CD44 or RHAMM in at least one type of mammalian cell. An antagonist may function in a direct or indirect manner. For instance, the antagonist may function to partially or fully block, inhibit or neutralize one or more biological activities of WISP-1 polypeptide, in vitro, in situ, or in vivo, e.g., as a result of its direct binding to WISP-1 polypeptide. The antagonist may also function indirectly to partially or fully block, inhibit or neutralize one or more biological activities of WISP-1 polypeptide, in vitro, in situ, or in vivo as a result of, e.g., blocking or inhibiting another effector molecule.

The term "WISP-1 antagonist" refers to any molecule that partially or fully blocks, inhibits, or neutralizes a biological activity of WISP-1 and include but are not limited to, antibodies, immunoadhesins, WISP-1 immunoadhesins, WISP-1 fusion proteins, covalently modified forms of WISP-1, WISP-1 variants and fusion proteins thereof, WISP-1 antibodies, and higher oligomer forms of WISP-1 (dimers, aggregates) or homo- or heteropolymer forms of WISP-1. To determine whether a WISP-1 antagonist molecule partially or fully blocks, inhibits or neutralizes a biological activity of WISP-1, assays may be conducted to assess the effect(s) of the antagonist molecule on, for example, various cells (as described in the Examples) or in an in vivo murine model of lung cancer metastasis. The various assays may be conducted in known in vitro or in vivo assay formats. Preferably, the WISP-1 antagonists employed in the methods described herein will be capable of blocking or neutralizing at least one type of WISP-1 activity, which may optionally be determined in assays such as described herein.

The term "antibody" is used in the broadest sense and specifically covers, for example, single monoclonal antibodies, antibody compositions with polyepitopic specificity, single chain antibodies, and fragments of antibodies. "Antibody" as used herein includes intact immunoglobulin or antibody molecules, polyclonal antibodies, multispecific antibodies (i.e., bispecific antibodies formed from at least two intact antibodies) and immunoglobulin fragments (such as Fab, F(ab')$_2$, or Fv), so long as they exhibit any of the desired antagonistic properties described herein.

Antibodies are typically proteins or polypeptides which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains [Chothia et al., *J. Mol. Biol.*, 186:651-663 (1985); Novotny and Haber, *Proc. Natl. Acad. Sci. USA*, 82:4592-4596 (1985)]. The light chains of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

"Antibody fragments" comprise a portion of an intact antibody, generally the antigen binding or variable region of the intact antibody. Examples of antibody fragments include Fab, Fab', F(ab')2, and Fv fragments, diabodies, single chain antibody molecules, and multispecific antibodies formed from antibody fragments.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies [see Kabat, E. A. et al., *Sequences of Proteins of Immunological Interest*, National Institutes of Health, Bethesda, Md. (1987)]. The constant domains are not involved directly in binding an antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include chimeric, hybrid and recombinant antibodies produced by splicing a variable (including hypervariable) domain of the antibody of interest with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity or properties. See, e.g. U.S. Pat. No. 4,816,567 and Mage et al., in *Monoclonal Antibody Production Techniques and Applications*, pp. 79-97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256:495 (1975), or may be made by recombinant DNA methods such as described in U.S. Pat. No. 4,816,567. The "monoclonal antibodies" may also be isolated from phage libraries generated using the techniques described in McCafferty et al., *Nature*, 348:552-554 (1990), for example.

"Humanized" forms of non-human (e.g. murine) antibodies are specific chimeric immunoglobulins, immunoglobulin chains, or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

A "human antibody" is one which possesses an amino acid sequence which corresponds to that of an antibody produced by a human and/or has been made using any of the techniques for making human antibodies known in the art or as disclosed herein. This definition of a human antibody includes antibodies comprising at least one human heavy chain polypeptide or at least one human light chain polypeptide, for example an antibody comprising murine light chain and human heavy chain polypeptides. Human antibodies can be produced using various techniques known in the art. In one embodiment, the human antibody is selected from a phage library, where that phage library expresses human antibodies (Vaughan et al. *Nature Biotechnology*, 14:309-314 (1996): Sheets et al. *PNAS*, (*USA*) 95:6157-6162 (1998)); Hoogenboom and Winter, *J. Mol. Biol.*, 227:381 (1991); Marks et al., *J. Mol. Biol.*, 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology*, 10: 779-783 (1992); Lonberg et al., *Nature*, 368: 856-859 (1994); Morrison, *Nature*, 368:812-13 (1994); Fishwild et al., *Nature Biotechnology*, 14: 845-51 (1996); Neuberger, *Nature Biotechnology*, 14: 826 (1996); Lonberg and Huszar, *Intern. Rev. Immunol.*, 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region (using herein the numbering system according to Kabat et al., supra). The Fc region of an immunoglobulin generally comprises two constant domains, a CH2 domain and a CH3 domain, and optionally comprises a CH4 domain.

By "Fc region chain" herein is meant one of the two polypeptide chains of an Fc region.

The "CH2 domain" of a human IgG Fc region (also referred to as "Cγ2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immunol.* 22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protroberance" in one chain thereof and a corresponding introduced "cavity" in the other chain thereof; see U.S. Pat. No. 5,821,333). Such variant CH3 domains may be used to make multispecific (e.g. bispecific) antibodies as herein described.

"Hinge region" is generally defined as stretching from about Glu216, or about Cys226, to about Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of a Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/ or with an Fc region of a parent polypeptide, and most preferably at least about 90% sequence identity therewith, more preferably at least about 95% sequence identity therewith.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.*, 9:457-92 (1991). To assess ADCC activity of a molecule of interest, an in vitro ADCC assay, such as that described in U.S. Pat. No. 5,500, 362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)*, 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" and "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, *Annu. Rev. Immunol.*, 15:203-234 (1997)). FcRs are reviewed in Ravetch and Kinet, *Annu. Rev. Immunol.*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.*, 117:587 (1976); and Kim et al., *J. Immunol.*, 24:249 (1994)).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202:163 (1996), may be performed.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology*, 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene,* 169:147-155 (1995); Yelton et al. *J. Immunol.,* 155:1994-2004 (1995); Jackson et al., *J. Immunol.,* 154(7):3310-9 (1995); and Hawkins et al, *J. Mol. Biol.,* 226:889-896 (1992).

The term "immunospecific" as used in "immunospecific binding of antibodies" for example, refers to the antigen specific binding interaction that occurs between the antigen-combining site of an antibody and the specific antigen recognized by that antibody.

The terms "cancer", "cancerous", "metastasis" and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. The preferred cancers for treatment herein include breast cancer, gastric cancer, lung cancer, colon or colorectal cancer, glioma and glioblastoma.

The term "prodrug" as used in this application refers to a precursor or derivative form of a pharmaceutically active substance that is less cytotoxic to cancer cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery,* Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described below.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$ $Re^{186}$, $Re^{188}$ $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of conditions like cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin $\gamma_1^I$ and calicheamicin $\theta^I_1$, see, e.g., Agnew *Chem. Intl. Ed. Engl.,* 33:183-186 (1994); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine;

6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (W B Saunders: Philadelphia, 1995), especially p. 13.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; Apo-2 ligand (also referred to as TRAIL); mullerian-inhibiting substance; mouse gonadotropin-associated peptide; inhibin; activin; vascular endothelial growth factor; integrin; thrombopoietin (TPO); nerve growth factors; platelet-growth factor; transforming growth factors (TGFs) such as TGF-α and TGF-β; insulin-like growth factor-I and -II; erythropoietin (EPO); osteoinductive factors; interferons such as interferon-α, -β, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-2, IL-3, IL-4, IL-5, IL-6, IL-7, IL-8, IL-9, IL-11, IL-12; and other polypeptide factors including LIF and kit ligand (KL). As used herein, the term cytokine includes proteins from natural sources or from recombinant cell culture and biologically active equivalents of the native sequence cytokines.

"Treatment" is an intervention performed with the intention of preventing the development or altering the pathology of a disorder. Accordingly, "treatment" refers to both therapeutic treatment and prophylactic or preventative measures, wherein the object is to prevent or slow down (lessen) the targeted pathological condition or disorder. Those in need of treatment include those already with the disorder as well as those in which the disorder is to be prevented. In treatment of a disorder, a therapeutic agent may directly decrease or increase the magnitude of response of a pathological component of the disorder, or render the disease more susceptible to treatment by other therapeutic agents, e.g. antibiotics, anti-fungals, anti-inflammatory agents, chemotherapeutics, etc.

The term "effective amount" is the minimum concentration of WISP-1 antagonist which causes, induces or results in either a detectable improvement or reduction of a pathological condition. In a method of treating cancer, an effective amount is one which causes, induces, or results in reduction of cancer cell number or tumor volume. Furthermore a "therapeutically effective amount" is the minimum concentration (amount) of WISP-1 antagonist administered to a mammal which would be effective in at least attenuating a pathological symptom.

"Chronic" administration refers to administration of the factor(s) in a continuous mode as opposed to an acute mode, so as to maintain the initial therapeutic effect (activity) for an extended period of time. "Intermittent" administration is treatment that is done not consecutively without interruption, but rather is cyclic in nature.

"Mammal" for purposes of treatment refers to any animal classified as a mammal, including humans, domestic and farm animals, and zoo, sports, or pet animals, such as dogs, horses, cats, cattle, pigs, hamsters, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®, hyaluronic acid (HA).

II. Methods and Compositions of the Invention

As described further in the Examples below, Applicant has surprisingly found that ectopic expression of WISP-1 in fibroblasts triggered HA production, namely increased HA production induced its accumulation at the cell surface and in the culture media. It is believed that cell surface HA can enhance anchorage-independent growth and tumorigenicity (Kosaki et al., *Cancer Res.*, 59:1141-1145 (1999)) and may diminish contact inhibition of cell proliferation, thereby promoting cell migration (Ichikawa et al., *J. Invest. Dermatol.*, 113:935-939 (1999); Itano et al., *Proc. Natl. Acad. Sci.*, 99:3609-3614 (2002)). Hyaluronan coat formation has also been correlated with cellular metastatic potential (Zhang et al., *Cancer Res.*, 55:428-433 (1995); Toole et al., *J. Biol.*

Chem., 277:4593-4596 (2002)). Analysis of HA synthases (HAS1, HAS2, and HAS3) expression revealed that WISP-1 promoted HAS2 induction whereas HAS1 and HAS3 mRNA levels remained unchanged. HAS2 is the main target of growth factor and cytokine up-regulated HA synthesis (Pienimaki et al., *J. Biol. Chem.*, 276:20428-20435 (2001)). Ectopic expression of HAS2 increases HA secretion and induces hyaluronan coat formation (Kosaki et al., supra). Moreover, HAS2 is believed to be important for hyaluronan-mediated transformation of epithelium to mesenchyme during cardiac morphogenesis (Camenisch et al., *J. Clin. Invest.*, 106:349-360 (2000)). Because epithelial to mesenchymal transition is also important for tumor invasion and metastasis, HAS2 is postulated to play an important role in epithelial tumor progression (Boyer et al., *Biochem. Pharmacol.*, 60:1091-1099 (2000); Hay, *Acta Anat.*, 154:8-20 (1995); Arias, *Cell*, 105: 425-431 (2001)). These results indicate that HA secretion induced by WISP-1 may be important for tumor invasion and metastasis.

WISP-1 also induced the expression of two HA receptors, CD44 and RHAMM. By inducing HA receptor expression and increasing HA production, WISP-1 may activate an autocrine and/or paracrine loop. Hyaluronan interaction with CD44 and RHAMM promotes cell locomotion and proliferation in vitro and tumor growth and metastasis in vivo (Turley et al., *J. Biol. Chem.*, 277:4589-4592 (2002); Sy et al., *Curr. Top. Microbiol. Immunol.*, 213:129-153 (1996); Hall et al., *J. Neurooncol.*, 26:221-229 (1995)).

The effects of WISP-1 on cell migration were analyzed in a cell wound healing assay and by time lapse microscopy, and the data showed that WISP-1 expression promoted cell motility. Further, isolated cells showed increased migration suggesting that WISP-1 could act through an autocrine mechanism. Purified recombinant WISP-1 promoted HAS2 and CD44 expression, though, when attached to a surface. This induction was further increased when WISP-1 was tethered through its interaction with decorin. Similarly, WISP-1 promoted cell motility when surface bound, suggesting that WISP-1 may also act through a paracrine mechanism when tethered to a substrate. The Examples herein show that WISP-1 induced cell motility was mediated by CD44, by abolishing migration with an anti-CD44 antibody. WISP-1 induced cell motility was also inhibited by WISP-1 antibodies. Moreover, WISP-1 haptotactic activity was not restricted to a single cell type as it induced both normal fibroblast and colon adenocarcinoma cell migration.

Because WISP-1 is believed to be a Wnt-1 downstream effector, the C57MG/Wnt-1 cell line was analyzed for phenotypes found in NRK/WISP-1 cells. Consistent with a role for WISP-1 downstream of Wnt-1, C57MG/Wnt-1 cells overexpressed HAS2 and CD44 and had higher CD44 protein content compared to the parental cell line. In addition, C57/Wnt-1 cells spontaneously scattered in culture and demonstrated a de-differentiated spindloid morphology similar to NRK/WISP-1H cells.

Expression analysis was also performed on a group of MMTV-Wnt-1 mammary tumors, and elevated CD44 and HAS2 expression was detected in all mammary tumors from the MMTV-Wnt-1 transgenic mice. In these tumors, WISP-1 expression was localized to the stromal fibroblasts whereas CD44 and HAS2 were expressed by tumor epithelial cells. Although negative for HAS2 expression, the peritumoral stroma contained high levels of HA whereas the tumor parenchyma stained only weakly for HA. Although it is generally accepted that fibroblasts are responsible for HA production, the origin of stromal HA is not definitely known. Because HAS2 expression was found only in the parenchyma, the experimental results disclosed herein suggest that the tumor cells are responsible for the HA synthesis and deposition in the stroma. Hyaluronan accumulation in the peritumoral stroma is frequently encountered in several tumor types and was previously reported for ovary, breast, prostate and colon adenocarcinomas (Ropponen et al., *Cancer Res.*, 58:342-347 (1998); Lipponen et al., *Eur. J. Cancer*, 37:849-856 (2001); Auvinen et al., *Am. J. Pathol.*, 156:529-536 (2000); Anttila et al., *Cancer Res.*, 60:150-155 (2000)). Moreover, a high stromal level of HA was associated with poor differentiation, metastatic behavior and unfavorable prognosis.

Because HA and CD44 are associated with tumor invasion, the metastatic potential of WISP-1 expressing cells was evaluated in vivo. After tail inoculation, NRK/WISP-1 cells readily colonized the lungs of injected mice and formed invasive tumors. NRK/WISP-1 cells exhibited a significant metastatic potential while NRK cells did not. Histological observation revealed that NRK/WISP-1 cells populated the vasculature and invaded the pulmonary airways. The lung colonization was proportional to the number of cells injected, the time after injection and the WISP-1 expression. In addition, Applicant found the metastatic potential to be proportional to CD44 and HAS2 expression levels, and the treatment of mice inoculated with NRK/WISP-1H cells with CD44 antibody or WISP-1 antibody greatly diminished the number and size of the tumors in the lung. Thus, it is likely that levels of WISP-1 promoted lung colonization through a hyaluronan-CD44 mechanism. This is consistent with previous reports demonstrating the importance of CD44 and its interaction with HA for tumor growth, metastasis and the retention of metastatic cells to the lung vasculature (Sy et al., supra; Kogerman et al., *Proc. Natl. Acad. Sci.*, 94:13233-13238 (1997)).

Although activation of the Wnt pathway by APC or β-catenin mutations may typically be associated with colorectal cancer, several lines of evidence suggest that it also plays a role in other types of cancer including mammary adenocarcinoma (Polakis, *Genes Dev.*, 14:1837-1851 (2000); Brown, *Breast Cancer Res.*, 3:351-355 (2001)). APC truncation and increased β-catenin levels were found in human breast cancer cell lines (Schlosshauer et al., *Carcinogenesis*, 21:1453-1456 (2000)). Somatic mutations of the APC gene were found in primary breast cancers (Furuuchi et al., *Am. J. Pathol.*, 156: 1997-2005 (2000)). In addition, β-catenin activating mutations promote mouse mammary adenocarcinomas Michaelson et al., *Oncogene*, 20:5525-5532 (2001)). Elevated levels of Wnt-1 and β-catenin were found in invasive ductal breast carcinomas and correlated with poor prognosis (Lin et al., *Proc. Natl. Acad. Sci.*, 97:4262-4266 (2000)). It is therefore possible that WISP-1 expression found in certain breast adenocarcinomas resulted from Wnt pathway activation. Applicants have also found, by Taqman analysis, that WISP-1 is overexpressed in cancers such as breast and glial tumors.

For at least these reasons, it is believed that WISP-1 antagonists will be particularly useful in treating and diagnosing various pathological disorders, such as cancer. The present invention accordingly provides methods for modulating, blocking or neutralizing WISP-1 activity in mammalian cells which comprise exposing the cells to a desired amount of WISP-1 antagonist. Preferably, the amount of WISP-1 antagonist employed will be an amount effective to reduce or inhibit cancer cell growth, metastasis or motility. This can be accomplished in vivo or ex vivo in accordance, for instance, with the methods described below and in the Examples. Exemplary conditions or disorders to be treated with such WISP-1 antagonists include conditions in mammals clinically referred to as cancer.

Diagnostic methods are also provided herein. For instance, the antagonists may be employed to detect invasive or metastatic cancers. The antagonist molecule may be used, e.g., in assays to detect or quantitate metastatic cancer cells in a sample. A sample, such as cells obtained from a mammal, can be incubated in the presence of a labeled antagonist, and detection of the labeled antagonist bound in the sample can be performed.

The antagonists which can be employed in the methods include, but are not limited to, WISP-1 immunoadhesins, fusion proteins comprising WISP-1, covalently modified forms of WISP-1, WISP-1 variants, fusion proteins thereof, and WISP-1 antibodies. Various techniques that can be employed for making the antagonists are described herein. For instance, methods and techniques for preparing WISP-1 polypeptides are described. Further modifications of the polypeptides, and antibodies to WISP-1 are also described.

In addition to the full-length native sequence WISP-1 polypeptide described herein, it is contemplated that WISP-1 polypeptide variants can be prepared. WISP-1 variants can be prepared by introducing appropriate nucleotide changes into the encoding DNA, and/or by synthesis of the desired polypeptide. Those skilled in the art will appreciate that amino acid changes may alter post-translational processes of the WISP-1 polypeptide, such as changing the number or position of glycosylation sites or altering the membrane anchoring characteristics.

Variations in the WISP-1 polypeptides described herein, can be made, for example, using any of the techniques and guidelines for conservative and non-conservative mutations set forth, for instance, in U.S. Pat. No. 5,364,934. Variations may be a substitution, deletion or insertion of one or more codons encoding the polypeptide that results in a change in the amino acid sequence as compared with the native sequence polypeptide. Optionally the variation is by substitution of at least one amino acid with any other amino acid in one or more of the domains of the WISP-1 polypeptide. Guidance in determining which amino acid residue may be inserted, substituted or deleted without adversely affecting the desired activity may be found by comparing the sequence of the WISP-1 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

WISP-1 polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the WISP-1 polypeptide.

WISP-1 polypeptide fragments may be prepared by any of a number of conventional techniques. Desired peptide fragments may be chemically synthesized. An alternative approach involves generating polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR.

In particular embodiments, conservative substitutions of interest are shown in the Table below under the heading of preferred substitutions. If such substitutions result in a change in biological activity, then more substantial changes, denominated exemplary substitutions in the Table, or as further described below in reference to amino acid classes, are introduced and the products screened.

TABLE

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the WISP-1 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc.*

London SerA, 317:415 (1986)] or other known techniques can be performed on the cloned DNA to produce the WISP-1 polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science*, 244:1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

Any cysteine residue not involved in maintaining the proper conformation of the WISP-1 polypeptide also may be substituted, generally with serine, to improve the oxidative stability of the molecule and prevent aberrant crosslinking. Conversely, cysteine bond(s) may be added to the WISP-1 polypeptide to improve its stability.

The description below relates primarily to production of WISP-1 polypeptides by culturing cells transformed or transfected with a vector containing WISP-1 polypeptide-encoding nucleic acid. It is, of course, contemplated that alternative methods, which are well known in the art, may be employed to prepare WISP-1 polypeptides. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the WISP-1 polypeptide may be chemically synthesized separately and combined using chemical or enzymatic methods to produce the desired WISP-1 polypeptide. The methods and techniques described are similarly applicable to production of WISP-1 variants, modified forms of WISP-1 and WISP-1 antibodies.

1. Isolation of DNA Encoding WISP-1 Polypeptide

DNA encoding WISP-1 polypeptide may be obtained from a cDNA library prepared from tissue believed to possess the WISP-1 polypeptide mRNA and to express it at a detectable level. Accordingly, human WISP-1 polypeptide DNA can be conveniently obtained from a cDNA library prepared from human tissue. The WISP-1 polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding WISP-1 polypeptide is to use PCR methodology [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for WISP-1 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various

*E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kan$^r$; *E. coli* W3110 strain 37D6, which has the complete genotype tonA ptr3 phoA E15 (argF-lac) 169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for WISP-1 polypeptide-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus*; *yarrowia* (EP 402,226); *Pichia pastoris* (EP 183,070; Sreekrishna et al., *J. Basic Microbiol.*, 28:265-278 [1988]); *Candida*; *Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora*, *Penicillium*, *Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenla*, *Candida*, *Kloeckera*, *Pichia*, *Saccharomyces*, *Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated WISP-1 polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for WISP-1 polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding WISP-1 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The WISP-1 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the WISP-1 polypeptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the WISP-1 polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the WISP-1 polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [de-Boer et al., *Proc. Natl. Acad. Sci. USA*, 80:21-25 (1983)]. Promoters for use in bacterial systems also will contain a Shine-Dalgarno (S.D.) sequence operably linked to the DNA encoding WISP polypeptide.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

WISP polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the WISP-1 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, -fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the WISP-1 polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding WISP-1 polypeptide.

Still other methods, vectors, and host cells suitable for adaptation to the synthesis of WISP polypeptide in recombinant vertebrate cell culture are described in Gething et al., *Nature*, 293:620-625 (1981); Mantei et al., *Nature*, 281:40-46 (1979); EP 117,060; and EP 117,058.

4. Culturing the Host Cells

The host cells used to produce the WISP polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence WISP polypeptide or against a synthetic peptide based on the DNA sequences provided herein or against exogenous sequence fused to WISP DNA and encoding a specific antibody epitope.

6. Purification of WISP Polypeptide

Forms of WISP polypeptide may be recovered from culture medium or from host cell lysates. If membrane-bound, it can be released from the membrane using a suitable detergent solution (e.g. Triton-X 100) or by enzymatic cleavage. Cells employed in expression of WISP-1 polypeptide can be disrupted by various physical or chemical means, such as freeze-thaw cycling, sonication, mechanical disruption, or cell lysing agents.

It may be desired to purify WISP-1 polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the WISP-1 polypeptide. Various methods of protein purification may be employed and such methods are known in the art and described for example in Deutscher, *Methods in Enzymology*, 182 (1990); Scopes, *Protein Purification Principles and Practice*, Springer-Verlag, New York (1982). The purification step(s) selected will depend, for example, on the nature of the production process used and the particular WISP-1 polypeptide produced.

Soluble forms of WISP-1 may be employed as antagonists in the methods of the invention. Such soluble forms of WISP-1 may comprise modifications, as described below (such as by fusing to an immunoglobulin, epitope tag or leucine zipper). Immunoadhesin molecules are further contemplated for use in the methods herein. WISP-1 immunoadhesins may comprise various forms of WISP-1, such as the full length polypeptide as well as soluble forms of the WISP-1 or a fragment thereof. In particular embodiments, the molecule may comprise a fusion of the WISP-1 polypeptide with an immunoglobulin or a particular region of an immunoglobulin. For a bivalent form of the immunoadhesin, such a fusion could be to the Fc region of an IgG molecule. The Ig fusions preferably include the substitution of a soluble (transmembrane domain deleted or inactivated) form of the polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions, see also U.S. Pat. No. 5,428,130 issued Jun. 27, 1995 and Chamow et al., *TIBTECH*, 14:52-60 (1996).

The simplest and most straightforward immunoadhesin design combines the binding domain(s) of the adhesin (e.g. the WISP-1) with the Fc region of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc region of immunoglobulin $G_1$ ($IgG_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;
(b) $AC_H$-($AC_H$, $AC_L$-$AC_H$, $AC_L$-$V_H C_H$, or $V_L C_L$-$AC_H$);
(c) $AC_L$-$AC_H$-($AC_L$-$AC_H$, $AC_L$-$V_H C_H$, $V_L C_L$-$AC_H$, or $V_L C_L$-$V_H C_H$)
(d) $AC_L$-$V_H C_H$-($AC_H$, or $AC_L$-$V_H C_H$, or $V_L C_L$-$AC_H$);
(e) $V_L C_L$-$AC_H$-($AC_L$-$V_H C_H$, or $V_L C_L$-$AC_H$); and
(f) $(A-Y)_n$-$(V_L C_L$-$V_H C_H)_2$, wherein each A represents identical or different adhesin amino acid sequences;

$V_L$ is an immunoglobulin light chain variable domain;

$V_H$ is an immunoglobulin heavy chain variable domain;

$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom et al., *Mol. Immunol.*, 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989. Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell*, 61:1303-1313 (1990); and Stamenkovic et al., *Cell*, 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

In another embodiment, the WISP-1 or WISP-1 antagonist may be covalently modified by linking the receptor polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337, or other like molecules such as polyglutamate. Such pegylated forms may be prepared using techniques known in the art.

Leucine zipper forms of these molecules are also contemplated by the invention. "Leucine zipper" is a term in the art used to refer to a leucine rich sequence that enhances, promotes, or drives dimerization or trimerization of its fusion partner (e.g., the sequence or molecule to which the leucine zipper is fused or linked to). Various leucine zipper polypeptides have been described in the art. See, e.g., Landschulz et al., *Science*, 240:1759 (1988); U.S. Pat. No. 5,716,805; WO 94/10308; Hoppe et al., *FEBS Letters*, 344:1991 (1994); Maniatis et al., *Nature*, 341:24 (1989). Those skilled in the art will appreciate that a leucine zipper sequence may be fused at either the 5' or 3' end of the WISP-1 or WISP-1 antagonist molecule.

The WISP-1 polypeptides of the present invention may also be modified in a way to form chimeric molecules by fusing the polypeptide to another, heterologous polypeptide or amino acid sequence. Preferably, such heterologous polypeptide or amino acid sequence is one which acts to oligimerize the chimeric molecule. In one embodiment, such a chimeric molecule comprises a fusion of the WISP-1 polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an -tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

It is contemplated that anti-WISP-1 antibodies may also be employed in the presently disclosed methods. Examples of such molecules include neutralizing or blocking antibodies which can reduce cancer cell growth, metastasis or motility. The anti-WISP-1 may be monoclonal antibodies.

Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include a WISP-1 polypeptide or a fusion protein thereof, such as a WISP-1-IgG fusion protein. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against WISP-1. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for WISP-1 and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Single chain Fv fragments may also be produced, such as described in Iliades et al., *FEBS Letters*, 409:437-441 (1997). Coupling of such single chain fragments using various linkers is described in Kortt et al., *Protein Engineering*, 10:423-433 (1997). A variety of techniques for the recombinant production and manipulation of antibodies are well known in the art. Illustrative examples of such techniques that are typically utilized by skilled artisans are described in greater detail below.

(i) Humanized Antibodies

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239: 1534-1536 (1988)], by substituting rodent CDRs or CDR sequences for the corresponding sequences of a human antibody.

Accordingly, such "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

(ii) Human Antibodies

Human monoclonal antibodies can be made by the hybridoma method. Human myeloma and mouse-human heteromyeloma cell lines for the production of human monoclonal antibodies have been described, for example, by Kozbor, *J. Immunol.* 133, 3001 (1984), and Brodeur, et al., *Monoclonal Antibody Production Techniques and Applications*, pp. 51-63 (Marcel Dekker, Inc., New York, 1987).

It is now possible to produce transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551-255 (1993); Jakobovits et al., *Nature* 362, 255-258 (1993).

Mendez et al. (*Nature Genetics* 15: 146-156 [1997]) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions ($\mu$, $\delta$ and $\chi$), and also harbors 800 kb of human κ locus containing 32 Vκ genes, Jκ segments and Cκ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, the phage display technology (McCafferty et al., *Nature* 348, 552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S. and Chiswell, David J., *Current Opinion in Structural Biology* 3, 564-571 (1993). Several sources of V-gene segments can be used for phage display. Clackson et al., *Nature* 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222, 581-597 (1991), or Griffith et al., *EMBO J.* 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., *Bio/Technol.* 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., *Nucl. Acids Res.* 21, 2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

As discussed below, the antibodies of the invention may optionally comprise monomeric, antibodies, dimeric antibodies, as well as multivalent forms of antibodies. Those skilled in the art may construct such dimers or multivalent forms by techniques known in the art. Methods for preparing monovalent antibodies are also well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

(iii) Bispecific Antibodies

Bispecific antibodies are monoclonal, preferably human or humanized, antibodies that have binding specificities for at least two different antigens. In the present case, one of the binding specificities is for WISP-1. For example, bispecific antibodies specifically binding WISP-1 or WISP-1 variants and another CNN family member (e.g., WISP-2, WISP-3, CTGF, Cyr61, or Nov) or other molecules such as CD44 are within the scope of the present invention.

Methods for making bispecific antibodies are known in the art. Traditionally, the recombinant production of bispecific antibodies is based on the coexpression of two immunoglobulin heavy chain-light chain pairs, where the two heavy chains have different specificities (Millstein and Cuello, *Nature* 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published 13 May 1993), and in Traunecker et al., *EMBO* 10, 3655-3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT Publication No. WO 94/04690, published on Mar. 3, 1994.

For further details of generating bispecific antibodies see, for example, Suresh et al., *Methods in Enzymology* 121, 210 (1986).

(iv) Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

(v) Antibody Fragments

In certain embodiments, the anti-WISP-1 antibody (including murine, human and humanized antibodies, and antibody variants) is an antibody fragment. Various techniques have been developed for the production of antibody fragments. Traditionally, these fragments were derived via proteolytic digestion of intact antibodies (see, e.g., Morimoto et al., *J. Biochem. Biophys. Methods* 24:107-117 (1992) and Brennan et al., *Science* 229:81 (1985)). However, these fragments can now be produced directly by recombinant host cells. For example, Fab'-SH fragments can be directly recovered from *E. coli* and chemically coupled to form F(ab')$_2$ fragments (Carter et al., *Bio/Technology* 10:163-167 (1992)). In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. A variety of techniques for the production of antibody fragments will be apparent to the skilled practitioner. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an F(ab')$_2$ fragment that has two antigen combining sites and is still capable of cross-linking antigen.

The Fab fragments produced in the antibody digestion also contain the constant domains of the light chain and the first constant domain (CH$_1$) of the heavy chain. Fab' fragments differ from Fab fragments by the addition of a few residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

Antibodies are glycosylated at conserved positions in their constant regions (Jefferis and Lund, *Chem. Immunol.* 65:111-128 [1997]; Wright and Morrison, *TibTECH* 15:26-32 [1997]). The oligosaccharide side chains of the immunoglobulins affect the protein's function (Boyd et al., *Mol. Immunol.* 32:1311-1318 [1996]; Wittwe and Howard, *Biochem.* 29:4175-4180 [1990]), and the intramolecular interaction between portions of the glycoprotein which can affect the conformation and presented three-dimensional surface of the glycoprotein (Hefferis and Lund, supra; Wyss and Wagner, *Current Opin. Biotech.* 7:409-416 [1996]). Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., *Nature Med.* 1:237-243 [1995]). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., *Mol. Immunol.* 32:1311-1318 [1996]), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., *Mature Biotech.* 17:176-180 [1999]).

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc. Glycosylation variants may, for example, be prepared by removing, changing and/or adding one or more glycosylation sites in the nucleic acid sequence encoding the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation (including glycosylation pattern) of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, significant variations in the glycosylation pattern of the antibodies can be expected (see, e.g. Hse et al., *J. Biol. Chem.* 272:9062-9070 [1997]). In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

Triabodies are also within the scope of the invention. Such antibodies are described for instance in Iliades et al., supra and Kortt et al., supra.

The antibodies of the present invention may be modified by conjugating the antibody to a cytotoxic agent (like a toxin molecule) or a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278. This technology is also referred to as "Antibody Dependent Enzyme Mediated Prodrug Therapy" (ADEPT).

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; caspases such as caspase-3; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes can be covalently bound to the antibodies by techniques well known in the art such as the use of heterobifunctional crosslinking reagents. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature*, 312: 604-608 (1984).

Further antibody modifications are contemplated. For example, the antibody may be linked to one of a variety of nonproteinaceous polymers, e.g., polyethylene glycol, polypropylene glycol, polyoxyalkylenes, or copolymers of polyethylene glycol and polypropylene glycol, or other molecules such as polyglutamate. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Osol, A., Ed., (1980). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Formulations

The WISP-1 antagonists described herein, are optionally employed in a carrier. Suitable carriers and their formulations are described in *Remington's Pharmaceutical Sciences,* 16th ed., 1980, Mack Publishing Co., edited by Osol et al. Typically, an appropriate amount of a pharmaceutically-acceptable salt is used in the carrier to render the formulation isotonic. Examples of the carrier include saline, Ringer's solution and dextrose solution. The pH of the carrier is preferably from about 5 to about 8, and more preferably from about 7.4 to about 7.8. It will be apparent to those persons skilled in the art that certain carriers may be more preferable depending upon, for instance, the route of administration and concentration of active agent being administered. The carrier may be in the form of a lyophilized formulation or aqueous solution.

Acceptable carriers, excipients, or stabilizers are preferably nontoxic to cells and/or recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or non-ionic surfactants such as TWEEN™, PLURONICS™ or polyethylene glycol (PEG).

The formulation may also contain more than one active compound as necessary for the particular indication being treated, preferably those with complementary activities that do not adversely affect each other.

The antagonists described herein may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration should be sterile. This is readily accomplished by filtration through sterile filtration membranes.

Sustained-release preparations may be prepared. Suitable examples of sustained-release preparations include semipermeable matrices of solid hydrophobic polymers containing the active agent, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

Modes of Therapy

The molecules described herein are useful in treating various pathological conditions, such as cancer. These conditions can be treated by administration of one or more antagonists described herein. Diagnosis in mammals of the various pathological conditions described herein can be made by the skilled practitioner. Diagnostic techniques are available in the art which allow, e.g., for the diagnosis or detection of cancer or immune related disease in a mammal. For instance, cancers may be identified through techniques, including but not limited to, palpation, blood analysis, x-ray, NMR and the like.

The antagonist(s) can be administered in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Optionally, administration may be performed through mini-pump infusion using various commercially available devices. The antagonists may also be employed using gene therapy techniques which have been described in the art.

Effective dosages and schedules for administering antagonists may be determined empirically, and making such determinations is within the skill in the art. Single or multiple dosages may be employed. It is presently believed that an effective dosage or amount of antagonist used alone may range from about 1 µg/kg to about 100 mg/kg of body weight or more per day. Interspecies scaling of dosages can be performed in a manner known in the art, e.g., as disclosed in Mordenti et al., *Pharmaceut. Res.*, 8:1351 (1991).

When in vivo administration of an antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue. Those skilled in the art will understand that the dosage of antagonist that must be administered will vary depending on, for example, the mammal which will receive the agonist or antagonist, the route of administration, and other drugs or therapies being administered to the mammal.

Depending on the type of cells and/or severity of the disease, about 1 µg/kg to 15 mg/kg (e.g. 0.1-20 mg/kg) of antagonist antibody is an initial candidate dosage for administration, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful.

A single type of antagonist may be used in the methods of the invention. For example, a WISP-1 immunoadhesin molecule may be administered. Alternatively, the skilled practitioner may opt to employ a combination of antagonists in the methods, e.g., a combination of a WISP-1 immunoadhesin and WISP-1 antibody. It is contemplated that yet additional therapies may be employed in the methods. The one or more other therapies may include but are not limited to, administration of radiation therapy, cytokine(s), growth inhibitory agent(s), chemotherapeutic agent(s), cytotoxic agent(s), tyrosine kinase inhibitors, ras farnesyl transferase inhibitors, angiogenesis inhibitors, and cyclin-dependent kinase inhibitors which are known in the art and defined further with particularity in Section I above. In addition, therapies based on therapeutic antibodies that target tumor antigens such as Rituxan™ or Herceptin™ as well as anti-angiogenic antibodies such as anti-VEGF.

Preparation and dosing schedules for chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of, e.g. an antagonist, or may be given simultaneously therewith. The antagonist, for instance, may also be combined with an anti-estrogen compound such as tamoxifen or an anti-progesterone such as onapristone (see, EP 616812) in dosages known for such molecules.

It may be desirable to also administer antibodies against other antigens, such as antibodies which bind to CD20, CD11a, CD18, CD40, CD44, ErbB2, EGFR, ErbB3, ErbB4, vascular endothelial factor (VEGF), or other TNFR family members (such as DR4, DR5, OPG, TNFR1, TNFR2). Alternatively, or in addition, two or more antibodies binding the same or two or more different antigens disclosed herein may be co-administered to the patient. Sometimes, it may be beneficial to also administer one or more cytokines to the patient. In one embodiment, the antagonists herein are co-administered with a growth inhibitory agent. For example, the growth inhibitory agent may be administered first, followed by an antagonist of the present invention.

The antagonist and one or more other therapies may be administered concurrently or sequentially. Following administration of antagonist, treated cells in vitro can be analyzed. Where there has been in vivo treatment, a treated mammal can be monitored in various ways well known to the skilled practitioner.

Articles of Manufacture

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agents in the composition may comprise antagonist(s). The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., *Molecular Cloning: A Laboratory Manual*, Cold Spring Harbor Press N.Y., 1989; Ausubel et al., *Current Protocols in Molecular Biology*, Green Publishing Associates and Wiley Interscience, N.Y., 1989; Innis et al., *PCR Protocols: A Guide to Methods and Applications*, Academic Press, Inc., N.Y., 1990; Harlow et al., *Antibodies: A Laboratory Manual*, Cold Spring Harbor Press, Cold Spring Harbor, 1988; Gait, M. J., *Oligonucleotide Synthesis*, IRL Press, Oxford, 1984; R. I. Freshney, *Animal Cell Culture*, 1987; Coligan et al., *Current Protocols in Immunology*, 1991.

A description of the assays and materials referred to in the following Examples is provided below:

Proteins and Antibodies: Full length human WISP-1-Fc fusion protein was expressed and purified as described previously (Desnoyers et al., *J. Biol. Chem.*, 276:47599-47607 (2001)). Purified mouse anti-rat CD44 antibody (clone OX49) was from BD Bioscience (Bedford Mass.). The mouse IgG2a isotype control antibody was from Pharmingen. The FITC conjugated mouse anti-rat CD44 was from Serotec (Raleigh, N.C.) and the FITC conjugated mouse IgG1 isotype control antibody was from DAKO (Denmark). The rat anti-mouse CD44 (clone KM114) was from Pharmingen. The actin antibody (clone C4) was from ICN biomedicals (Aurora, Ohio). Murine anti-human WISP-1 monoclonal antibodies were generated and selected using WISP-1-Fc as an immunogen and the protocols and reagents described in the Examples of U.S. Pat. No. 6,387,657 issued May 14, 2002. Five such monoclonal antibodies have been deposited by Applicants with the ATCC, as noted below.

Cells and Tissue Specimens: NRK-49F and SW480 cell lines (ATCC, Manassas, Va.) were maintained in High glucose Dulbecco's Modified Eagle's Medium (HGDMEM) supplemented with 10% fetal calf serum (FBS). Parental C57MG, C57MG expressing Wnt-1 (C57MG/Wnt-1), NRK-49F expressing high levels of hWISP-1 (NRK/WISP-1H), NRK-49F expressing lower levels of hWISP-1 (NRK/WISP-1L) and NRK-49F containing an empty vector (NRK/control) were obtained from Arnold Levine (Princeton University, Princeton, N.J.) and maintained in media containing 2.5 µg ml$^{-1}$ puromycin (Xu et al., *Genes Dev.*, 14:585-595 (2000)). Wnt-1 transgenic mice obtained from Harold Varmus (National Cancer Institute, National Institutes of Health, Bethesda, Md.) were bred with p53 null mice obtained from Jackson Laboratories (Bar Harbor, Mass.) to generate the Wnt-1 transgenic/p53 knock out mice. Specimens of breast tumor and mammary duct epithelium were excised from those mice for analysis.

Particle Exclusion Assay: The erythrocyte sedimentation assay was used as described previously, with minor modifications. (Knudson et al., *J. Cell Sci.*, 99:227-235 (1991)). NRK/WISP-1 ((normal rat kidney fibroblasts transfected with WISP-1; see Xu et al., *Genes Dev.*, 14:585-595 (2000)) and NRK/control cells (normal rat kidney fibroblasts; obtained from Arnold Levine, Princeton University, Princeton, N.J.) (1×10$^5$ cells/well) were seeded in Falcon 6 well plates (Becton Dickinson, Franklin Lanes, N.J.) and maintained in high glucose Dulbecco's modified Eagle's Medium supplemented with 10% fetal bovine serum (FBS) (Life Technologies, Gaithersburg, Md.) overnight at 37° C., 5% CO$_2$. The next day, the media was removed and 10$^8$ sheep RBCs (Inter-Cell Technologies, Hopewell, N.J.) in 750 µl PBS/0.1% BSA (Boehringer Mannheim, Indianapolis, Ind.) were added and allowed to settle for 15 minutes. The cells were observed using a Nikon Diaphot 300 inverted microscope, and digital images were acquired using a SONY DKC-5000 digital photo camera (Japan).

Hyaluronan Staining of Cultured Cells: Hyaluronan Staining was performed as previously described, with minor modifications (Pienimaki et al., *J. Biol. Chem.*, 276:20428-20435 (2001)). NRK/WISP-1 and NRK/control cells (8–10×10$^3$)

were plated in 8 well plastic chamber slides and maintained (as described above) overnight at 37° C., 5% $CO_2$. The next day the cells were washed with phosphate buffered saline (PBS) and fixed with 4% paraformaldehyde in PBS for 20 minutes at room temperature. The cells were washed with PBS and the non-specific binding sites were saturated for 30 minutes with distilled water containing 1% bovine serum albumin (BSA) and 0.1% Triton X-100 (Calbiochem, LaJolla, Calif.). Biotinylated HA binding protein (HA-BP) (Seikagaku America, Falmouth, Mass.) (5 µg/ml in PBS/3% BSA) was added and incubated overnight at room temperature. The next day the cells were washed with PBS and incubated for 30 minutes with 1:1000 FITC-conjugated streptavidin (DAKO, Carpinteria, Calif.) in TBS and 1%/BSA. The cells were washed in PBS, mounted using Vectashield (Burlingame, Calif.) containing 1 µg/ml Hoechst 33342 (Molecular Probes, Eugene, Oreg.) and visualized under a Nikon Eclipse 800 fluorescent microscope. Images were acquired with a Photometrics 300 CCD camera operated at −40° C. interfaced with an Apple G3 computer. The same procedure was also used to stain frozen sections of mammary tumors from Wnt-1 transgenic mice).

Real time RT-PCR: Relative RNA expression level was determined using real-time RT-PCR as previously reported (Winer et al., *Anal. Biochem.*, 270:41-49 (1999)). Total RNA was extracted from cells with Tri-Reagent using the manufacturer's protocol (Molecular Research Center). Specific primers and fluorogenic probes were designed and used to amplify and quantitate gene expression level. The genes' specific signals were normalized to that of the glyceraldehyde-3-phosphate dehydrogenase housekeeping gene. Triplicate sets of data were averaged for each condition. All TaqMan RT-PCR reagents were purchased from Applied Biosystems (Foster City, Calif.). To test the effect of recombinant WISP-1 on gene expression, petri dishes (35 mm) were coated overnight at 4° C. with 75 µg $ml^{-1}$ hWISP-1-Fc in PBS. The next day, cells ($3 \times 10^5$ cells/dish) were plated on the coated surface and the expression analysis was performed after 18 hours. In certain cases the coated surface was washed and treated for an additional 2 hours at room temperature before cell were seeded.

FACS Analysis: Cells were harvested by trypsinization, washed with PBS and incubated in PBS 1% BSA/20% glucose containing 1 µg $ml^{-1}$ FITC conjugated anti-CD44 (Serotec, Raleigh, N.C.) or an isotype control Ab (DAKO, Denmark) for 30 minutes at room temperature. Cells were washed with the same buffer and analyzed on an EPICS XL-MCL (Coulter, Miami, Fla.).

Western Blot: NRK/C and NRK/W1H were cultured to confluency in 10 $cm^2$ plates. The cells were washed with PBS and extracted with 300 µl of 1% Triton-X100 in TBS for 5 minutes. Proteins were precipitated by adding 10 volumes of acetone to the extract. Samples were reduced, denatured and loaded on a 4-20% gradient SDS polyacrylamide gel. The gel was transferred to PVDF membranes and probed with a anti-rat CD44 antibody (OX49) or an anti-mouse CD44 (KM114) at a 1 µg/ml concentration and detected using a HRP-conjugated anti-mouse IgG secondary antibody and the Amersham ECL detection reagents. Actin detection in the samples was used as loading control.

Scatter Assay: The cells were plated in 24 well plates at low concentration (~1000 cells/well) and allowed to form colonies over 3 days. The cells were stained using Diff-Quik (Dade Behring, Newark, Del.) and colonies were observed under the microscope.

Cell Wound Healing Assay: Cell migration was evaluated using a cell wound healing assay previously described with minor modifications (Pienimaki et al., *J. Biol. Chem.*, 276: 20428-20435 (2001)). Briefly, cells were cultured until they reached confluency. One line (~1 mm) was drawn in the cell layer using a micropipette equipped with a disposable yellow tip. Cell migration over the cleared area was monitored by time lapse microscopy over 15 hours. The area newly occupied by the cells after this period was measured using NIH image software calibrated with a stage micrometer.

Time Lapse Microscopy: Cells were plated in HGDMEM/10% FBS and their random migration was observed for 15 hours using time lapse microscopy. The distance covered by the cells was measured using NIH image software calibrated with a stage micrometer.

Migration Assay: Haptotaxis was measured using a modified Boyden chamber system as described previously (Bourguignon et al., *J. Biol. Chem.*, 275:1829-1838 (2000)). The underside of 8 µm porosity 24-well format PET membrane filters (Falcon) were coated overnight at 4° C. with 50 µl of protein (50 µg $ml^{-1}$) in PBS. The coated inserts were rinsed in serum-free media and $0.5 \times 10^5$ NRK cells in 0.5 ml HGD-MEM/10% FBS were added to the upper chamber. The lower chamber was filled with 0.75 ml of the same media and the plates were incubated overnight at 37° C. The next day the upper chamber was wiped with a cotton swab and the cells that migrated to the lower side of the insert were stained with the Diff-Quik Stain Kit (Dade Behring Inc.) and counted under the microscope. Triplicate sets of data were averaged for each condition.

In certain cases, the coated inserts were washed and treated for an additional 2 hours at room temperature.

In situ Hybridization: PCR primers were designed to amplify either a 740 bp fragment of murine WISP-1 spanning from nt 440-1180 of NM_018865 (upper-5' GGCTGC-CATCTGTGACCCA (SEQ ID NO:12) and lower-5' CAT-AGGACCT GCCGGGAGAA A (SEQ ID NO:13)) or a 706 bp fragment of murine WISP-1 spanning from nt 204-910 of NM_018865 (upper-5' GCCGTGGCAGTCCTGAGGG (SEQ ID NO:14) and lower-5' CAGCACCGGG CAT-TGACGTT A (SEQ ID NO:15)) or a 464 bp fragment of murine CD44 spanning from nt 144-608 of M27129 (upper-5' TGGAGAAAAATGGCCGCTAC A (SEQ ID NO:16)) and lower-5' TGGGGTGCTC TTCTCGATGG (SEQ ID NO: 17)) or a 630 bp fragment of murine HAS2 spanning from nt 927-1557 of NM_008216 (upper-5' GGACAAATCGGC-CACGTACA T (SEQ ID NO:18) and lower-5' CTTGCTC-CAT CGGGTCTGC (SEQ ID NO:19)). Primers included extensions encoding 27-nucleotide T7 or T3 RNA polymerase initiation sites to allow in vitro transcription of sense or antisense probes, respectively, from the amplified products. (Lu et al., *Cell Vision*, 1:169-176 (1994)). All tissues were fixed in 4% formalin and paraffin-embedded. Sections 3-5 microns thick were deparaffinized, deproteinated in 4 mg/ml of proteinase K for 30 minutes at 37° C., and further processed for in situ hybridization as previously described. (Holcomb et al., *EMBO J.*, Aug. 2000 1; 19(15):4046-55). $^{33}$P-UTP labeled sense and antisense probes were hybridized to the sections at 55° C. overnight. Unhybridized probe was removed by incubation in 20 mg/ml RNase A for 30 minutes at 37° C., followed by a high stringency wash at 55° C. in 0.1×SSC for 2 hours and dehydration through graded ethanols. The slides were dipped in NBT2 nuclear track emulsion, exposed in sealed plastic slide boxes containing dessicant for 4 weeks at 4° C., developed and counterstained with hematoxylin and eosin.

Example 1

Stable fibroblast cell lines expressing high (NRK/WISP-1H) or low (NRK/WISP-1L) levels of WISP-1 and a control cell line containing an empty vector (NRK/control) were used to evaluate the effect of WISP-1 on HA production. As demonstrated by the particle exclusion assay, NRK/WISP-1H cells accumulated a large hyaluronan pericellular coat capable of excluding sedimenting erythrocytes (FIG. 1a). NRK/WISP-1L accumulated a smaller pericellular matrix (FIG. 1b) whereas no matrix surrounded NRK/control (FIG. 1c) or NRK/WISP-1H cells treated with hyaluronidase (data not shown). Accumulation of cell surface associated HA was also evaluated by fluorescent staining using the biotinylated HA binding protein (bHABP). The staining revealed HA accumulation at the NRK/WISP-1H cell surface (FIG. 1d) whereas no staining was detected on NRK control cells (FIG. 1e).

The effect of WISP-1 on HA secretion was evaluated by comparing the accumulation of HA in the culture media of NRK/WISP-1H to NRK/control cells over time. After 24 hours, HA concentration in the NRK/WISP-1H media was 3.5 fold greater in NRK/control cell media and gradually increased to 8 fold after 144 h (FIG. 1f). Together these results show that WISP-1 expression in NRK cells promotes HA accumulation at the cell surface and in the culture media.

Example 2

To identify the enzyme responsible for the WISP-1 triggered HA production, the expression of the known HA synthases (HAS1, HAS2 and HAS3) in NRK/WISP-1H, NRK/WISP-1L and NRK/control cells was analyzed. HAS2 expression was increased up to 10 fold in WISP-1 producing cells whereas HAS1 and HAS3 mRNA levels were identical to the control (FIG. 2a). CD44 and RHAMM mRNA levels were also increased in NRK/WISP-1 cell lines whereas hyaluronidase expression remained unchanged (FIG. 2a). Moreover, HAS2, CD44 and RHAMM mRNA levels were proportional to WISP-1 expression. As demonstrated by FACS analysis (FIG. 2b) and Western blot (FIG. 2c), the increase in CD44 mRNA expression in the NRK/WISP-1H cells resulted in a 4-fold increase in CD44 protein level.

Example 3

HA was shown to stimulate cell migration by interacting with two cell surface receptors, CD44 and RHAMM (Hall et al., supra; Bourguignon et al., supra). Because WISP-1 increased both HA production and CD44 and RHAMM expression, the motility of WISP-1 expressing cells was evaluated. When plated at a low density, NRK/control cells proliferated and formed well defined colonies (FIG. 3a). Proliferating NRK/WISP-1L cells formed less defined groups as some cells departed from the growing colonies (FIG. 3b). No NRK/WISP-1H colonies were seen, cells scattered in a random pattern (FIG. 3c). Contrary to the control (FIG. 3d), WISP-1 expressing cells also revealed a hyper elongated morphology with extended lamellipodia characteristic of high motility (FIG. 3e). Using time lapse microscopy, a 4 fold increase in the migration distance of NRK/WISP-1H was observed compared to control cells (FIG. 3f). NRK/WISP-1H also showed a 2.5 fold increase in migration area in a cell wound healing assay (FIG. 3g). Together these results demonstrate that WISP-1 expression may promote cell migration.

Example 4

To determine whether the ectopic addition of WISP-1 could promote HAS2 expression and cell migration, an assay was conducted using purified recombinant WISP-1-IgG (Desnoyers et al., supra). WISP-1 addition to the culture media did not promote HAS2 expression (data not shown). When NRK cells were plated onto a WISP-1-IgG coated surface, HAS2 expression increased compared to cells plated onto uncoated plastic or onto an irrelevant IgG chimeric protein (TNFR-IgG) coated surface (FIG. 4a). Although decorin alone promoted HAS2 expression, this induction was further increased three fold after the coated surface was incubated with WISP-1. The effects of ectopic WISP-1 addition on NRK cell migration were also examined. In a transwell assay, WISP-1-IgG induced the haptotactic migration of NRK cells when coated on the filter's lower surface (FIG. 4b). Coating of an irrelevant IgG chimeric protein (TNFR-IgG) or addition of WISP-1-IgG to the lower chamber did not promote migration. A CD44 or a WISP-1 antibody (FIG. 4b) inhibited the haptotactic migration induced by WISP-1. Moreover, WISP-1 haptotactic activity was not limited to fibroblasts as it also promoted the migration of SW480 cells, a colon adenocarcinoma cell line (FIG. 4c). Together these results demonstrate that ectopic WISP-1 addition increases HAS2 expression and promotes cell migration through a CD44 mediated mechanism. It is believed, though not fully understood, that WISP-1 presentation may be important for migration as it may need to be tethered to a substrate to elicit this activity.

Example 5

Because WISP-1 is believed to be a downstream effector of Wnt-1, WISP-1, HAS2 and CD44 expression in a mammary epithelial cell line stably transfected with Wnt-1 (C57MG/Wnt-1) were analyzed. When compared to the control cell line (C57MG), C57MG/Wnt-1 cells showed a 2.7, 5.8 and 3 fold increase in WISP-1, HAS2 and CD44 mRNA expression respectively (FIG. 5a). As demonstrated by Western blot, C57/Wnt-1 cells also showed a 6-fold increase in CD44 protein content (FIG. 5b). Moreover, unlike the control cell line, Wnt-1 expressing cells failed to form distinct colonies and scattered when put in culture at low density (FIG. 5c). These results show that HAS2 and CD44 expression and cell motility are elevated in cell lines where WISP-1 expression is triggered by Wnt-1.

Example 6

Wnt-1 expression in mammary epithelium promotes tumor development in transgenic mice (Li et al., *Oncogene*, 19:1002-1009 (2000); Tsukamoto et al., *Cell*, 55:619-625 (1988)). Because WISP-1 is a putative downstream effector of Wnt-1, the mRNA expression of HAS2 and CD44 in spontaneous mammary tumors from MMTV-Wnt-1 transgenic mice was measured. When compared to mammary duct epithelium, HAS2 mRNA expression was increased between 2.5 and 5.5 fold in all mammary tumors analyzed (n=5; FIG. 5d). Similarly, CD44 mRNA expression was induced between 2.2 and 4.2 fold in all tumors (n=5; FIG. 5e). These results show that HAS2 and CD44 are overexpressed in MMTV-Wnt-1 transgenic mice mammary tumors expressing WISP-1.

Example 7

In situ hybridization demonstrated elevated WISP-1 expression in the peritumoral stroma of MMTV-Wnt-1 transgenic mouse mammary tumors (FIGS. 6a, b). In contrast, HAS2 (FIG. 6c-d) and CD44 (FIG. 6 e-f) expression was found only in tumoral epithelial cells. The localization of CD44 in the tumor parenchyma was confirmed by immunohistochemistry (FIG. 6g). Link protein staining revealed an accumulation of hyaluronan associated with the tumor stroma (FIG. 6h). The highest staining intensity was found in the immediate vicinity of the tumor lobule whereas weaker staining was localized to the normal mammary duct epithelium. These findings are consistent with the suggestion that WISP-1 may regulate interactions between tumor and stromal cells that involve hyaluronic acid and CD44.

Example 8

The metastasis and growth potential of transformed lines was evaluated as described previously (Welch et al., *Cancer Res.*, 60:1552-1556 (2000)). Nine-week-old Swiss nu/nu female mice were used. Briefly, cells were harvested by trypsinization and washed twice with PBS. Each mouse was injected into the lateral tail vein with 100 µl of a suspension containing $5 \times 10^4$ or $2.5 \times 10^5$ cells. At 2, 3 and 4 week postinjection, mice were examined using cine-magnetic resonance imaging (MRI) for apparition of pulmonary lesions and necropsies were performed. The lungs were perfused in Bouin's fixative, excised and H&E stained sections were generated for evaluation of pulmonary tumor colonization.

Longitudinal sections of the left lung, and a single transverse section of the cranial, medial, caudal, and accessory lobes of the right lung were evaluated. Histologically, affected lungs had spindloid neoplastic cells that infiltrated the pulmonary interstitium. However, because the severity of the changes was variable the following grading system was established.

I=Minimal involvement of the pulmonary interstitium—10-20% of the lung is affected. Nests and clusters of spindloid neoplastic cells multifocally disrupt the pulmonary interstitium. Affected foci are commonly along the pleural surface, extending into the interstitium. No vessels or large airways are affected.

II=Moderate involvement of the pulmonary interstitium—20-50% of the lung is affected. Nests and clusters of spindloid neoplastic cells multifocally disrupt the pulmonary interstitium. Some vessels or large airways are filled with spindloid cells. Spindloid cells frequently form a broad band or large mass subjacent to the pleura and extending into the interstitium. Overlying mesothelium is plump (reactive).

III=Severe involvement of the pulmonary interstitium—50-100% of the lung is affected. Nests and clusters of spindloid neoplastic cells multifocally disrupt the pulmonary interstitium. Blood vessels and large airways are filled with spindloid cells. Spindloid cells form a broad band or large mass subjacent to the pleura and extending into the interstitium. Spindloid cells are often embedded in a pale basophilic to amphophilic acellular material. Overlying mesothelium is plump (reactive). Minimal unaffected area for gas exchange remains.

The results of the lung colonization of nude mice inoculated with NRK/WISP-1H, NRK/WISP-1L and NRK/control cells are summarized in FIGS. 7 and 10. In mice inoculated with NRK/WISP-1H or NRK/WISP-1L, cells formed lung masses in a time- and dose-dependent manner. The most severe lesions were seen in mice injected with $2.5 \times 10^5$ NRK/WISP-1H and necropsied at 4 weeks post-injection. At 2 and 3 weeks post-injection, the mice had less severe but progressive tumor formation (grade I-II; see grading system above). Mice injected with $2.5 \times 10^5$ NRK/WISP-1L had only minimal lung tumor formation by 4 weeks post-injection. After 4 weeks post-injection, mice inoculated with $0.5 \times 10^5$ NRK/WISP-1L cells were either normal or had minimal neoplastic infiltration (grade I), whereas mice injected with $0.5 \times 10^5$ NRK/WISP-1H cells showed increased neoplastic infiltration (grade I-II). Histological observation revealed that the lungs of animals inoculated with NRK/control cells were normal (FIG. 7a-c). In NRK/WISP-1 injected animals, neoplastic spindloid cells initially formed small clusters within, protruding from, or subjacent to the pleural surface of the lungs (grade I; FIG. 7d-f) often embedded in a pale basophilic to amphophilic acellular material. In more severely affected animals, the neoplastic cells formed a broad confluent band subjacent to the pleura (grade II; FIG. 7g-i). In the most severely affected animals, blood vessels and large airways were filled with spindloid cells. (grade III; FIGS. 7j-l). MRI analysis showed increased density (hypersignal) outlining the right and left lungs along the pleura in animals with histologic grade II and grade III invasion. Severity of the lesion on MRI was consistent with the histologic score (FIGS. 7a, d, g, j). These results indicate that WISP-1 expression promotes cellular metastatic growth potential.

Example 9

NRK/WISP-1H cells ($2.5 \times 10^5$ cells) were inoculated in the tail vein of nude mice. Starting on the day of the cell inoculation, the mice were injected intraperitoneally twice a week with 10 mg/kg of a CD44 antibody, an isotype control antibody or with buffer only (PBS). The lungs were fixed and excised after four weeks for gross anatomical analysis.

After 4 weeks, the severity of the lesions found in CD44 antibody treated animals (n=5) varied from normal to grade I whereas all (n=10) animals treated with a control antibody or saline had grade III lesions (FIG. 8a). The average area of metastatic foci in the lungs of animals treated with CD44 antibody was reduced by 99% (P<0.00003) compared to animals treated with a control antibody (FIG. 8b).

Example 10

An assay was conducted to examine binding specificity of certain WISP-1 antibodies. Full length mouse WISP-1 (GenBank accession number NM_018865) and full length human WISP-1 (GenBank accession number AF100779; FIG. 9) were cloned into an expression vector encoding the human IgG$_1$ Fc region downstream of the WISP-1 sequence. The resulting recombinant fusion protein (WISP-1-Fc) was synthesized in a baculovirus expression system using Sf9 insect cells and purified to homogeneity from serum-free conditioned medium by affinity chromatography on a Protein A-Sepharose 4 Fast Flow (Amersham Pharmacia Biotech). Full length human WISP-1 was also expressed with an amino terminal hexa-histidine tag (WISP-1-His) in an *E. coli* strain. The cell lysate was subjected to chromatography on a Ni$^{2+}$-NTA agarose column (Qiagen). WISP-1-His was eluted with a 0 to 500 mM imidazole gradient. Fractions containing the eluted WISP-1-His were then pooled and dialyzed. Human WISP-1 from a mammalian expression system was obtained by lysing NRK cells stably transfected with human WISP-1 (Arnold Levine; Princeton University, Princeton, N.J.) with SDS-PAGE sample buffer. A control cell lysate was generated with NRK cells stably transfected with an empty vector.

WISP-1 (50 ng) from various expression systems was electrophoresed on a SDS polyacrylamide gel and electro-transferred onto polyvinyldifluoride (PVDF) membranes and probed with different WISP-1 monoclonal antibodies.

WISP-1 antibodies 3D11.D7 (also referred to herein as "3D11"), 11C2.C10 (also referred to herein as "11C2"), 9C11.C7 (also referred to herein as "9C11") and 5D4.F6 (also referred to herein as "5D4") bound specifically to WISP-1 generated from baculovirus, bacterial and mammalian expression systems (FIG. 11a). These antibodies did not bind to the murine WISP-1 from baculovirus and did not recognize any protein from the control lysate. The WISP-1 antibodies 6F8, 3A7, 10H12, 3A11, 6E3, 3H10, 5G1, and 10B1 recognized both human and murine WISP-1 only when generated with the baculovirus expression system (FIG. 11b). These antibodies did not recognize human WISP-1 when produced in a bacterial or mammalian expression system. The antibody from clone 9C10 did not bind to any protein after Western blot.

These results suggest that WISP-1 antibodies 3D11, 11C2, 9C11 and 5D4 specifically recognize human WISP-1 and can be used for WISP-1 detection by Western blot.

Example 11

An assay was conducted to identify the epitopes recognized by the WISP-1 antibodies 11C2, 9C11, 5D4 and 3D11.

Full length human WISP-1 (GenBank accession number AF100779) was cloned into a pIRESpuro2 expression vector (Clontech Laboratories, Palo Alto, Calif.) encoding 6 histidines downstream of the WISP-1 sequence. Deletion mutants were also generated by removing one, two or three domains of human WISP-1. The resulting constructs were also cloned into the pIRESpuro2 expression vector. The nomenclature used to identify the different WISP-1 constructs refer to the domains they contain. (see FIG. 12B) Domain 1 is the insulin-like growth factor binding protein domain (IFGBP), domain 2 is the von Willebrand factor C (VWFc) domain, domain 3 is the thrombospondin (TSP) domain, and the domain 4 is the C-terminal (CT) domain. The variable region resides between domain 2 and 3. These regions and domains of WISP-1 are illustrated in FIG. 12A.

The sequences encoding these domains of WISP-1 are as follows:

```
Sequences of WISP-1 Constructs
Domain 1:
                                            (SEQ ID NO: 3)
GAATTCACCATGAGGTGGTTCCTGCCCTGGACGCTGGCAGCAGTGACAGC

AGCAGCCGCCAGCACCGTCCTGGCCACGGCCCTCTCTCCAGCCCCTACGA

CCATGGACTTTACTCCAGCTCCACTGGAGGACACCTCCTCACGCCCCCAA

TTCTGCAAGTGGCCATGTGAGTGCCCGCCATCCCCACCCCGCTGCCCGCT

GGGGGTCAGCCTCATCACAGATGGCTGTGAGTGCTGTAAGATGTGCGCTC

AGCAGCTTGGGGACAACTGCACGGAGGCTGCCATCTGTGACCCCCACCGG

GGCCTCTACTGTGACTACAGCGGGGACCGCCCGAGGTACGCAATAGGAGT

GTGTGCACAGGCGGCCGCACACCACCATCACCATCACCATCACTAAGTGA

GGCCGCATAGATAACTGATCCAGTGTGCTGGAATTAATTC
```

```
Domain 2:
                                            (SEQ ID NO: 4)
GAATTCACCATGAGGTGGTTCCTGCCCTGGACGCTGGCAGCAGTGACAGC

AGCAGCCGCCAGCACCGTCCTGGCCACTGCAGTGGTCGGTGTGGGCTGCG

TCCTGGATGGGGTGCGCTACAACAACGGCCAGTCCTTCCAGCCTAACTGC

AAGTACAACTGCACGTGCATCGACGGCGCGGTGGGCTGCACACCACTGTG

CCTCCGAGTGCGCCCCCCGCGTCTCTGGTGCCCCCACCCGCGGCGCGTGA

GCATACCTGGCCACTGCTGTGAGCAGTGGGTATGTGCGGCCGCACACCAC

CATCACCATCACCATCACTAAGTGAGGCCGCATAGATAAC
```

```
Domain 3:
                                            (SEQ ID NO: 5)
GAATTCACCATGAGGTGGTTCCTGCCCTGGACGCTGGCAGCAGTGACAGC

AGCAGCCGCCAGCACCGTCCTGGCCACTGCAGCATGGCACAGGAACTGCA

TAGCCTACACAAGCCCCTGGAGCCCTTGCTCCACCAGCTGCGGCCTGGGG

GTCTCCACTCGGATCTCCAATGTTAACGCCCAGTGCTGGCCTGAGCAAGA

GAGCCGCCTCTGCAACTTGCGGCCATGCGATGTGGACATCCATACACTCA

TTAAGGCGGCCGCACACCACCATCACCATCACCATCACTAAGTGAGGCCG

CATAGATAACTGATCCAGTGT
```

```
Domain 4:
                                            (SEQ ID NO: 6)
GAATTCACCATGAGGTGGTTCCTGCCCTGGACGCTGGCAGCAGTGACAGC

AGCAGCCGCCAGCACCGTCCTGGCCACTGCAGGGAAGAAGTGTCTGGCTG

TGTACCAGCCAGAGGCATCCATGAACTTCACACTTGCGGGCTGCATCAGC

ACACGCTCCTATCAACCCAAGTACTGTGGAGTTTGCATGGACAATAGGTG

CTGCATCCCCTACAAGTCTAAGACTATCGACGTGTCCTTCCAGTGTCCTG

ATGGGCTTGGCTTCTCCCGCCAGGTCCTATGGATTAATGCCTGCTTCTGT

AACCTGAGCTGTAGGAATCCCAATGACATCTTTGCTGACTTGGAATCCTA

CCCTGACTTCTCAGAAATTGCCAACGCGGCCGCACACCACCATCACCATC

ACCATCACTAAGTGAGGCCGCATAGATAACTGATCCAGTGTG
```

```
Domain 1,2:
                                            (SEQ ID NO: 7)
GAATTCACCATGAGGTGGTTCCTGCCCTGGACGCTGGCAGCAGTGACAGC

AGCAGCCGCCAGCACCGTCCTGGCCACGGCCCTCTCTCCAGCCCCTACGA

CCATGGACTTTACTCCAGCTCCACTGGAGGACACCTCCTCACGCCCCCAA

TTCTGCAAGTGGCCATGTGAGTGCCCGCCATCCCCACCCCGCTGCCCGCT

GGGGGTCAGCCTCATCACAGATGGCTGTGAGTGCTGTAAGATGTGCGCTC

AGCAGCTTGGGGACAACTGCACGGAGGCTGCCATCTGTGACCCCCACCGG

GGCCTCTACTGTGACTACAGCGGGGACCGCCCGAGGTACGCAATAGGAGT

GTGTGCACAGGTGGTCGGTGTGGGCTGCGTCCTGGATGGGGTGCGCTACA

ACAACGGCCAGTCCTTCCAGCCTAACTGCAAGTACAACTGCACGTGCATC

GACGGCGCGGTGGGCTGCACACCACTGTGCCTCCGAGTGCGCCCCCCGCG

TCTCTGGTGCCCCCACCCGCGGCGCGTGAGCATACCTGGCCACTGCTGTG

AGCAGTGGGTATGTGCGGCCGCACACCACCATCACCATCACCATCACTAA

GTGAGGCCGCATAGATAAC
```

-continued

Domain 1,2,3:
(SEQ ID NO: 8)
GAATTCACCATGAGGTGGTTCCTGCCCTGGACGCTGGCAGCAGTGACAGC

AGCAGCCGCCAGCACCGTCCTGGCCACGGCCCTCTCTCCAGCCCCTACGA

CCATGGACTTTACTCCAGCTCCACTGGAGGACACCTCCTCACGCCCCCAA

TTCTGCAAGTGGCCATGTGAGTGCCCGCCATCCCCACCCCGCTGCCCGCT

GGGGGTCAGCCTCATCACAGATGGCTGTGAGTGCTGTAAGATGTGCGCTC

AGCAGCTTGGGGACAACTGCACGGAGGCTGCCATCTGTGACCCCCACCGG

GGCCTCTACTGTGACTACAGCGGGGACCGCCCGAGGTACGCAATAGGAGT

GTGTGCACAGGTGGTCGGTGTGGGCTGCGTCCTGGATGGGGTGCGCTACA

ACAACGGCCAGTCCTTCCAGCCTAACTGCAAGTACAACTGCACGTGCATC

GACGGCGCGGTGGGCTGCACACCACTGTGCCTCCGAGTGCGCCCCCCGCG

TCTCTGGTGCCCCCACCCGCGGCGCGTGAGCATACCTGGCCACTGCTGTG

AGCAGTGGGTATGTGAGGACGACGCCAAGAGGCCACGCAAGACCGCACCC

CGTGACACAGGAGCCTTCGATGCTGTGGGTGAGGTGGAGGCATGGCACAG

GAACTGCATAGCCTACACAAGCCCCTGGAGCCCTTGCTCCACCAGCTGCG

GCCTGGGGGTCTCCACTCGGATCTCCAATGTTAACGCCCAGTGCTGGCCT

GAGCAAGAGAGCCGCCTCTGCAACTTGCGGCCATGCGATGTGGACATCCA

TACACTCATTAAGGCgGCCGCACACCACCATCACCATCACCATCACTAAG

TGAGGCCGCATAGATAACTGATCCAGTGTGCTGGA

Domain 1,2,4:
(SEQ ID NO: 9)
GAATTCACCATGAGGTGGTTCCTGCCCTGGACGCTGGCAGCAGTGACAGC

AGCAGCCGCCAGCACCGTCCTGGCCACGGCCCTCTCTCCAGCCCCTACGA

CCATGGACTTTACTCCAGCTCCACTGGAGGACACCTCCTCACGCCCCCAA

TTCTGCAAGTGGCCATGTGAGTGCCCGCCATCCCCACCCCGCTGCCCGCT

GGGGGTCAGCCTCATCACAGATGGCTGTGAGTGCTGTAAGATGTGCGCTC

AGCAGCTTGGGGACAACTGCACGGAGGCTGCCATCTGTGACCCCCACCGG

GGCCTCTACTGTGACTACAGCGGGGACCGCCCGAGGTACGCAATAGGAGT

GTGTGCACAGGTGGTCGGTGTGGGCTGCGTCCTGGATGGGGTGCGCTACA

ACAACGGCCAGTCCTTCCAGCCTAACTGCAAGTACAACTGCACGTGCATC

GACGGCGCGGTGGGCTGCACACCACTGTGCCTCCGAGTGCGCCCCCCGCG

TCTCTGGTGCCCCCACCCGCGGCGCGTGAGCATACCTGGCCACTGCTGTG

AGCAGTGGGTATGTCTGCAGGCAGGGAAGAAGTGTCTGGCTGTGTACCAG

CCAGAGGCATCCATGAACTTCACACTTGCGGGCTGCATCAGCACACGCTC

CTATCAACCCAAGTACTGTGGAGTTTGCATGGACAATAGGTGCTGCATCC

CCTACAAGTCTAAGACTATCGACGTGTCCTTCCAGTGTCCTGATGGGCTT

GGCTTCTCCCGCCAGGTCCTATGGATTAATGCCTGCTTCTGTAACCTGAG

CTGTAGGAATCCCAATGACATCTTTGCTGACTTGGAATCCTACCCTGACT

TCTCAGAAATTGCCAACGCGGCCGCACACCACCATCACCATCACCATCAC

TAAGTGAGGCCGCATAGATAACTGATCCAGTGTGCTGGAATTAATTCGCT

-continued

GTCTGCGAGGGCCAGCTGTTGGGGTGAGTACTCCCTCTCAAAAGCGGGCA

TGACTTCTGCGCTA

Domain 1,3,4:
(SEQ ID NO: 10)
GAATTCACCATGAGGTGGTTCCTGCCCTGGACGCTGGCAGCAGTGACAGC

AGCAGCCGCCAGCACCGTCCTGGCCACGGCCCTCTCTCCAGCCCCTACGA

CCATGGACTTTACTCCAGCTCCACTGGAGGACACCTCCTCACGCCCCCAA

TTCTGCAAGTGGCCATGTGAGTGCCCGCCATCCCCACCCCGCTGCCCGCT

GGGGGTCAGCCTCATCACAGATGGCTGTGAGTGCTGTAAGATGTGCGCTC

AGCAGCTTGGGGACAACTGCACGGAGGCTGCCATCTGTGACCCCCACCGG

GGCCTCTACTGTGACTACAGCGGGGACCGCCCGAGGTACGCAATAGGAGT

GTGTGCGCATGCTGTGGGTGAGGTGGAGGCATGGCACAGGAACTGCATAG

CCTACACAAGCCCCTGGAGCCCTTGCTCCACCAGCTGCGGCCTGGGGGTC

TCCACTCGGATCTCCAATGTTAACGCCCAGTGCTGGCCTGAGCAAGAGAG

CCGCCTCTGCAACTTGCGGCCATGCGATGTGGACATCCATACACTCATTA

AGGCAGGGAAGAAGTGTCTGGCTGTGTACCAGCCAGAGGCATCCATGAAC

TTCACACTTGCGGGCTGCATCAGCACACGCTCCTATCAACCCAAGTACTG

TGGAGTTTGCATGGACAATAGGTGCTGCATCCCCTACAAGTCTAAGACTA

TCGACGTGTCCTTCCAGTGTCCTGATGGGCTTGGCTTCTCCCGCCAGGTC

CTATGGATTAATGCCTGCTTCTGTAACCTGAGCTGTAGGAATCCCAATGA

CATCTTTGCTGACTTGGAATCCTACCCTGACTTCTCAGAAATTGCCAACG

CGGCCGCACACCACCATCACCATCACCATCACTAAGTGAGGCCGCATAGA

TAAC

Domain 2,3,4:
(SEQ ID NO: 11)
GAATTCACCATGAGGTGGTTCCTGCCCTGGACGCTGGCAGCAGTGACAGC

AGCAGCCGCCAGCACCGTCCTGGCCACTGCAGTGGTCGGTGTGGGCTGCG

TCCTGGATGGGGTGCGCTACAACAACGGCCAGTCCTTCCAGCCTAACTGC

AAGTACAACTGCACGTGCATCGACGGCGCGGTGGGCTGCACACCACTGTG

CCTCCGAGTGCGCCCCCGCGTCTCTGGTGCCCCCACCCGCGGCGCGTGA

GCATACCTGGCCACTGCTGTGAGCAGTGGGTATGTGAGGACGACGCCAAG

AGGCCACGCAAGACCGCACCCCGTGACACAGGAGCCTTCGATGCTGTGGG

TGAGGTGGAGGCATGGCACAGGAACTGCATAGCCTACACAAGCCCCTGGA

GCCCTTGCTCCACCAGCTGCGGCCTGGGGGTCTCCACTCGGATCTCCAAT

GTTAACGCCCAGTGCTGGCCTGAGCAAGAGAGCCGCCTCTGCAACTTGCG

GCCATGCGATGTGGACATCCATACACTCATTAAGGCAGGGAAGAAGTGTC

TGGCTGTGTACCAGCCAGAGGCATCCATGAACTTCACACTTGCGGGCTGC

ATCAGCACACGCTCCTATCAACCCAAGTACTGTGGAGTTTGCATGGACAA

TAGGTGCTGCATCCCCTACAAGTCTAAGACTATCGACGTGTCCTTCCAGT

GTCCTGATGGGCTTGGCTTCTCCCGCCAGGTCCTATGGATTAATGCCTGC

TTCTGTAACCTGAGCTGTAGGAATCCCAATGACATCTTTGCTGACTTGGA

ATCCTACCCTGACTTCTCAGAAATTGCCAACGCGGCCGCACACCACCATC

-continued

```
ACCATCACCATCACTAAGTGAGGCCGCATAGATAACTGATCCAGTGTGCT

GGAATTAATTCGCTGTCTGCGA
```

Cells (HEK 293T) were transfected with the different constructs, and the culture media was collected after 48 hours. One milliliter of culture media was incubated with 20 μl of cobalt-agarose for 1 hour, centrifuged and washed. The adsorbed proteins were eluted by heating the pellet at 100° C. for 5 minutes in 20 μl of SDS-PAGE sample buffer. The samples were electrophoresed, electro-transferred onto PVDF and probed with the different WISP-1 antibodies.

Antibodies 11C2, 9C11 and 5D4 recognized only WISP-1 contructs containing the 19 first amino acids of the variable region located between domain 2 and 3 (FIGS. 12C; 12E; 12G). The WISP-1 antibody 3D11 recognized only WISP-1 contructs containing the domain 1 (amino acids 24 to 117; FIGS. 12D; 12F).

These results indicate that the antibodies 11C2, 9C11 and 5D4 recognize specifically the variable region of WISP-1 whereas the antibody 3D11 recognizes specifically the domain 1 of WISP-1.

Example 12

An assay was conducted to identify the epitope recognized by the WISP-1 antibody 9C10.F5 (also referred to herein as "9C10").

Culture media from HEK 293T cells transfected with the various WISP-1 deletion contructs (as described above in Example 11) was incubated with 1 μg of WISP-1 antibody 9C10 and 20 μl of protein A-agarose for 1 hour at room temperature. The immunocomplex was precipitated by centrifugation and eluted by heating the pellet at 100° C. for 5 minutes in 20 μl of SDS-PAGE sample buffer. The samples were electrophoresed, electro-transferred onto PVDF and probed with WISP-1 antibody 11C2.

The antibody 9C10 immunoprecipitated only constructs containing the domain 1 of WISP-1 (FIG. 13). These results demonstrate that the antibody 9C10 specifically recognizes the domain 1 of WISP-1 and can be used for immunoprecipitation.

Example 13

WISP-1 antibody 9C10 (100 μl of 2 μg/ml in carbonate buffer, pH 9.6) was coated to Maxisorb plates overnight at 4° C. The plates were blocked with 200 μl of PBS/3% BSA for 1 hour. A standard curve was made of serial dilutions of WISP-1-Fc (100 μl in PBS/3% BSA) and incubated for 1 hour. After the incubation, the plates were washed with 100 μl PBS/0.05% Tween and WISP-1 antibodies (100 μl of 2 μg/ml) in PBS/3% BSA (biotinylated 11C2 or 55B) were incubated for 1 hour. For biotinylated 11C2, the plates were further incubated with 2 μg/ml HRP-conjugated streptavidin. For 55B, the plates are washed and incubated with HRP-conjugated donkey anti-rabbit IgG for 1 hour. At the end of the incubation, the wells were washed 6 times with 200 μl of PBS containing 0.05% Tween-20, and the signal was visualized using 100 μl of the horseradish peroxidase chromogenic substrate TMB (Kirkegaard & Perry Laboratories). The reaction was stopped with 100 μl of 1 M phosphoric acid, and the OD at 450 nm was measured. Non-specific binding was determined in parallel incubations by omitting microtiter well coating. No signal was generated when WISP-1-Fc or a WISP-1 antibody was omitted.

Using the antibody 9C10 for capture and the antibodies 11C2 and 55B for detection, an ELISA was conducted capable of detecting concentration of WISP-1 as low as 0.4 μg/ml (FIG. 14). This ELISA may be useful for detecting WISP-1 protein in biological fluids such as serum.

Example 14

Maxisorb plates were coated overnight at 4° C. with 50 μl/well of 10 μg/ml heparin (Sigma). The non specific binding sites were blocked with 200 μl of PBS/3% BSA for 1 hour. The plates were then incubated for 1 hour with 50 μl of 6 μg/ml hWISP-1-Fc in PBS/3% BSA in the presence of serial dilutions of WISP-1 antibodies. The plates were washed with PBS/0.05% Tween and further incubated 1 hour with 50 μl of 2 μg/ml HRP conjugated anti-human IgG-Fc in PBS/3% BSA. The plates were washed, and 100 μl of HRP substrate (TMB) was added. The color development was stopped with 100 μl of 1 M phosphoric acid and the OD at 450 nm was measured.

The WISP-1 antibodies 11C2, 5D4 and 9C11 inhibited WISP-1 binding to heparin with an $IC_{50}$ of 1.9, 2.5 and 3.7 μg/ml, respectively (FIG. 15). The antibody 3D11 moderately reduced WISP-1 binding to heparin with a maximal inhibition of 62% at the highest concentration tested (40 μg/ml). The antibody 9C10 did not attenuate WISP-1 heparin binding, showing an inhibition curve similar to the irrelevant antibody control.

These results demonstrate that antibodies recognizing the variable region can inhibit WISP-1 binding to heparin. Because the two WISP-1 antibodies recognizing domain 1 have little or no effect on WISP-1 binding to heparin, it is presently believed that the domain 1 is less likely to participate in this interaction.

Example 15

Haptotaxis was measured using a modified Boyden chamber system. The underside of 8 μm porosity 24-well format PET membrane filters (Becton Dickinson, Franklin Lakes, N.J.) were coated overnight at 4° C. with 50 μl of protein (50 μg/ml) in PBS. Normal rat kidney cells (NRK; $5 \times 10^4/0.5$ ml HGDMEM/10% FBS) were added to the upper chamber, the lower chamber was filled with the same media and the plates were incubated at 37° C. The next day, the upper chamber was wiped with a cotton swab, and the cells that migrated to the lower side of the insert were stained and counted under a microscope. Triplicate sets of data were averaged for each condition. In certain cases, the coated inserts were washed and treated for an additional 2 hours at room temperature.

In a transwell assay, WISP-1-Fc coated on the filters' lower surface induced the haptotactic migration of NRK cells (FIG. 16A). Coating of an irrelevant IgG chimeric protein (TNFR-Fc) or addition of WISP-1-Fc to the lower chamber did not promote migration. In the presence of coated WISP-1-Fc, five different WISP-1 antibodies (9C10, 11C2, 3D11, 9C11, 5D4) markedly inhibited cell migration. In the absence of coated WISP-1-Fc, these antibodies did not show any effect on cell migration. These results demonstrate that WISP-1 antibodies can modulate cell migration in the presence of WISP-1. By blocking cell migration, WISP-1 antibodies may play an important therapeutic role in preventing cancer progression.

A summary of the characteristics and properties of the 3D11, 9C10, 11C2, 5D4, and 9C11 antibodies discussed in the Examples above is provided in FIG. 16B.

Example 16

Nine-week-old Swiss nu/nu female mice were injected into the lateral tail vein with 100 μl of a suspension containing $2.5 \times 10^5$ cells. Starting on the day of the inoculation, the mice were treated semiweekly by intraperitoneal injection (10 mg/kg) of WISP-1 antibodies (9C11, 11C2, 5D4, 9C10, 3D11) or isotype control antibody. After 3 weeks, lungs were perfused with 4% neutral buffered formalin, excised and H&E stained sections were generated. Longitudinal sections of the left lung, and a transverse section of the cranial, medial, caudal, and accessory lobes of the right lung were evaluated. For each slide the number of metastatic foci was counted and the average area of metastatic foci was measured using the SPOT RT software (Diagnostic Instruments Incorporated, Burlingame, Calif.). The area ($\mu m^2$) was determined for at least five individual metastatic foci in four sections of lung.

After 3 weeks, the severity of the lesions found in WISP-1 antibody treated animals was greatly attenuated compared to control (FIGS. 17 a, b). The number of nodules and the average area of the metastatic foci found in mice treated with WISP-1 antibodies (n=5) were reduced compared to animals treated with a control antibody (FIGS. 17 c,d). Furthermore, upon WISP-1 antibody treatment, the total pulmonary area covered by the lesions was reduced by 82-97% compared to animal treated with an isotype control antibody (FIG. 17e). These results demonstrate the in vivo efficacy of WISP-1 antibodies at reducing the tumor burden related to metastasis. Although the mechanism of action of the WISP-1 antibodies is not fully understood, it is believed their efficacy may be mediated by a growth reducing ability and/or a capacity at inhibiting the motility, invasion and seeding of cancer cells at a tissue site.

Example 17

Full length mouse WISP-1 (GenBank accession number NM_018865) was cloned into the pRK mammalian expression vector. The resulting construct (pRK-WISP-1; 18 ug) was co-transfected with 2 ug pSVi-puromycin plasmid in a 4T1 mouse mammary adenocarcinoma cell line (obtained from Dr. Fred Miller, Barbara Ann Karmanos Cancer Institute, Detroit, Mich.) using Fugene6 (Roche) according to manufacturer's instructions. After 2 days, cells were selected in 2 μg/ml puromycin. After 2 weeks, clones were isolated and WISP-1 expression was evaluated by immunofluorescence. The same procedure was used to generate control cell lines using an empty vector. The resulting 4T1/control and 4T1/WISP-1 cell lines were maintained in Iscove's Media containing 10% FBS and 3 μg/ml puromycin.

WISP-1 expression in 4T1/control, 4T1/WISP-1L, 4T1/WISP-1H, NRK/control, NRK/WISP-1L and NRK/WISP-1H cells lines was measured by semi-quantitative RT-PCR (Taqman) using primers and probes that do not distinguish between human and mouse WISP-1 gene.

WISP-1 was not expressed in 4T1/control cell lines. WISP-1 expression in 4T1/WISP-1H cell line was 2 fold higher than in 4T1/WISP-1L but 700 fold lower than in NRK/WISP-1H (FIG. 18).

Example 18

To evaluate WISP-1 effect on 4T1 cell scattering, 100,000 4T1/control, 4T1/WISP-1L or 4T1/WISP-1H cells were seeded in 6 well plate in Iscove's Media containing 10% fetal bovine serum. When plated at a low density, 4T1/control cells proliferated and formed well defined colonies (FIG. 19). Proliferating 4T1/WISP-1L cells formed less defined groups as some cells departed from the growing colonies (FIG. 19). No 4T1/WISP-1H colonies were seen, and cells scattered in a random pattern (FIG. 19). Together these results suggest that WISP-1 expression promotes cell migration.

Example 19

WISP-1 effect on 4T1 cell invasion was also evaluated using a Matrigel coated modified Boyden chamber system of 8 μm porosity 24-well format PET membrane filters (Falcon). 4T1/control, 4T1/WISP-1L or 4T1/WISP-1H cells (100,000 cells) were added to the upper chamber in 0.5 ml Iscove's Media. The lower chamber was filled with 0.75 ml of the same media containing 5% fetal bovine serum and the plates were incubated overnight at 37° C. The next day the upper chamber was wiped with a cotton swab and the cells that migrated to the lower side of the insert were stained with the Diff-Quik Stain Kit (Dade Behring Inc.) and counted under the microscope. Triplicate sets of data were averaged for each condition. 4T1/WISP-1H and 4T1/WISP-1L cells demonstrated a 12 and 6 fold increase invasion compared to 4T1/control, respectively (FIG. 20). These results suggest that WISP-1 promotes tumorigenic mammary epithelial cell invasion and may play a role in metastasis.

Example 20

WISP-1 effects on mammary epithelial cells tumorigenesis were evaluated by injecting $1.5 \times 10^5$ cells (4T1/control 1, 4T1/control 2, 4T1/WISP-1L or 4T1/WISP-1H) into the fourth mammary fat pad of 6-8 week old female BALB/c mice (6 mice/group). Tumor volumes were measured three times per week. Thirty one days after injection, the mice were sacrificed, the tumors were excised and weighted.

Inoculation of 4T1/WISP-1L cells (FIG. 21a; empty squares) and 4T1/WISP-1H cells (FIG. 21a; filled squares) generated faster growing tumors compared to 4T1/control 1 and 4T1/control 2 cells (FIG. 21a; empty and filled circles). After 31 days, the tumors formed by 4T1/WISP-1L and 4T1/WISP-1L inoculated were 4 fold larger (FIG. 21a) and 3 fold heavier (FIG. 21b) than the tumors formed by 4T1/control cells. These results suggest that WISP-1 may increase proliferation of mammary epithelial tumor cells.

Example 21

The expression of HAS2 and CD44 in tumors formed by the inoculated 4T1/control, 4T1/WISP-1L and 4T1/WISP-1H cells was measured. When compared to 4T1/control cells tumor, CD44 expression was increased between 5 and 23 fold in 4T1/WISP-1 cells tumors (FIG. 22). On the other hand, HAS2 expression remained identical in all tumors analyzed. These results suggest that WISP-1 increases expression of CD44 in mice inoculated with 4T1 cells. The overexpression of CD44 in these tumors may contribute to the promotion of metastasis.

Example 22

WISP-1 effects on mammary epithelial cells metastasis were evaluated by inoculating 4T1 cells in mice mammary fat pads (see Example 20) and examining the extent of the metastatic propagation by micro computer tomography and histology. After 31 days, the mice inoculated with 4T1/WISP-1L or 4T1/WISP-1H cells had extensive lung metastasis (FIGS. 23b and 23d) compared to the 4T1/control injected mice (FIGS. 23a and 23c). No significant differences were seen between the metastatic potential of 4T1/WISP-1L and 4T1/WISP-1H cells. The mice inoculated with 4T1/control cells had an average of 2.11 pulmonary foci with an average mass of 0.68 grams whereas mice inoculated with 4T1/WISP-1 cells had an average of 20.25 pulmonary foci with an average mass of 12.46 grams. Also, the average histology score for the lung of 4T1/WISP-1 cells injected mice was 0.92 compared to 0.11 for the NRK/control cells injected mice.

Using immunohistochemistry, it was also observed that the 4T1/WISP-1 pulmonary metastatic foci expressed high levels of CD44 (FIG. 23e). In these tumors, CD44 was localized at the plasma membrane of the 4T1/WISP-1 cells (FIG. 23f). Together these results demonstrate that WISP-1 promotes the metastatic potential of 4T1 cells, increasing the number of pulmonary metastatic foci (10 fold) and size (18 fold). Also, CD44 increased expression was maintained after the 4T1/WISP-1 had metastasized to the lungs.

Clinical observations of mice inoculated with 4T1/control 1, or 4T1/WISP-1 cells demonstrated that WISP-1 expression promoted metastasis at additional secondary sites. Two mice inoculated with 4T1/WISP-1H had a discolored white mass on the kidney whereas no other mice had evidence of kidney tumors.

Example 23

The human WISP-1 full length and deletion mutant constructs described above were transfected in normal rat kidney cells (NRK-49F). After 48 hours, the culture media was supplemented with 2 µg/ml puromycin. After 2 weeks, the pools of expressing cells were analyzed and the resulting cell lines were maintained in High glucose Dulbecco's Modified Eagle's Medium (HGDMEM) supplemented with 10% fetal calf serum (FBS) and 2 µg/ml puromycin.

WISP-1 expression in NRK/control, NRK/WISP-1__1234, NRK/WISP-1__134, NRK/WISP-1__234, NRK/WISP-1__123 and NRK/WISP-1__124 cells lines was measured by semi-quantitative RT-PCR (Taqman). Results are expressed as fold relative to WISP-1 expression in NRK/WISP-1__1234 (FIG. 24A). WISP-1 expression in NRK/WISP-1__134 and NRK/WISP-1__234 is 0.035 and 0.09 fold respectively compared to NRK/WISP-1__1234. NRK/WISP-1__123 expresses 16.1 fold and NRK/WISP-1__124 7.6 fold compared to NRK/WISP-1__1234.

The contribution of particular domains to WISP-1 promoted tumorigenesis was evaluated by injecting $5 \times 10^6$ cells (NRK/control, NRK/WISP-1__1234, NRK/WISP-1__123, NRK/WISP-1__124, NRK/WISP-1__134, NRK/WISP-1__234 cells) subcutaneously in 6-8 week old female nude mice (10 mice/group). Tumor volumes were measured weekly. After 35 days the mice were sacrificed, the tumors were excised and analyzed histologically.

Inoculation of NRK/WISP-1__1234 (FIG. 24B; filled triangles), NRK/WISP-1__134 (FIG. 24B; filled circles) and NRK/WISP-1__234 cells (FIG. 24B; filled squares) generated tumors. However the inoculation of NRK/WISP-1__123 (FIG. 24B; empty squares), NRK/WISP-1__124 (FIG. 24B; empty circles) and NRK/control (FIG. 24B; empty triangles) did not generate tumors. After 35 days, the tumors formed by NRK/WISP-1__234 cells were comparable in size to the tumors formed by NRK/WISP-1__1234 cells. However the tumors formed by NRK/WISP-1__134 cells were 2.5 fold larger than the tumors formed by NRK/WISP-1__1234 cells.

These results suggest that the domains 1 and 2 are not required for WISP-1 promoted NRK tumorigenesis but that the domains 3 and 4 are required for WISP-1 promoted NRK tumorigenesis. It is believed that WISP-1 antagonists of the invention may preferably bind to and/or block domains 3 and/or 4 of WISP-1.

In addition, results suggest the deletion of the domain 2 of WISP-1 may increase its tumorigenic potential.

Figure 25:
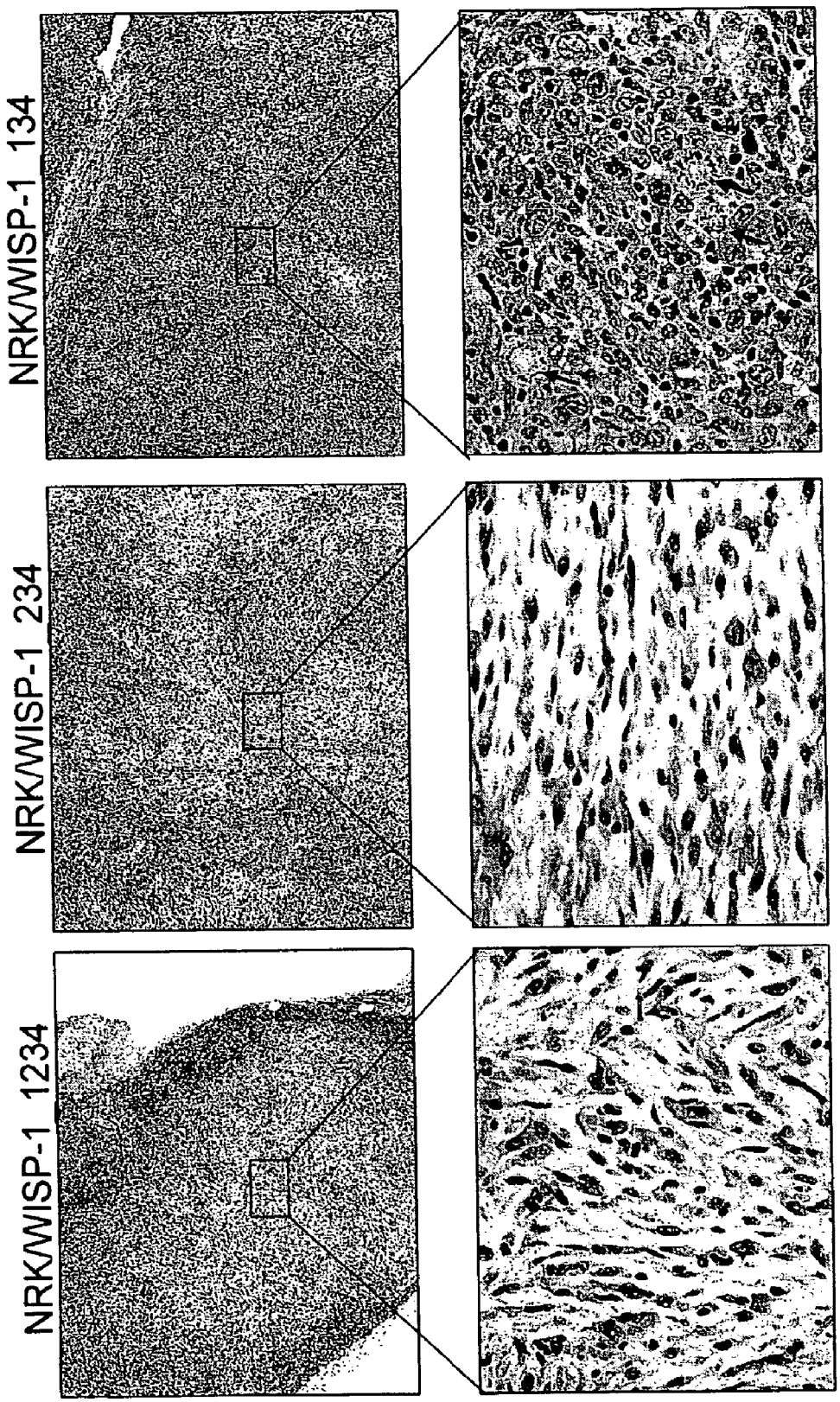
FIG. 25 shows the histological analysis of the excised tumors referred to in FIG. 24 and revealed that the neoplastic cells from NRK/WISP-1_234 tumors were phenotypically similar to the neoplastic cells from NRK/WISP-1_1234 tumors. In these tumors, cells appeared fibroblastic, differentiated and spindloid. The neoplastic cells from NRK/WISP-1_134 tumors were phenotypically different and appeared less differentiated, frequently multinucleated and had a brisk mitotic rate as demonstrated by the presence of multiple mitotic figures (arrows).
Figure 26:
FIG. 26 shows the histological analysis of the excised tumors in the NRK/WISP-1_134 xenograft referred to in FIG. 24, and reveals the neoplastic cells invaded several blood vessels adjacent to the tumor.

Histological analysis of the excised tumors (FIG. 25) revealed that the neoplastic cells from NRK/WISP-1__234 tumors were phenotypically similar to the neoplastic cells from NRK/WISP-1__1234 tumors. In these tumors, cells appeared fibroblastic, differentiated and spindloid. However the neoplastic cells from NRK/WISP-1__134 tumors were phenotypically different and appeared less differentiated, frequently multinucleated and had a brisk mitotic rate as demonstrated by the presence of multiple mitotic figures (arrows). In addition, neoplastic cells invaded several blood vessels adjacent to NRK/WISP-1__134 tumors (FIG. 26). These results indicate that WISP-1__134 expression may confer tumorigenicity to NRK cells by promoting their in vivo growth and invasive potential. Moreover the expression of this construct induces a phenotypic transformation characteristic of aggressive neoplastic cells.

Example 24

Figure 27:
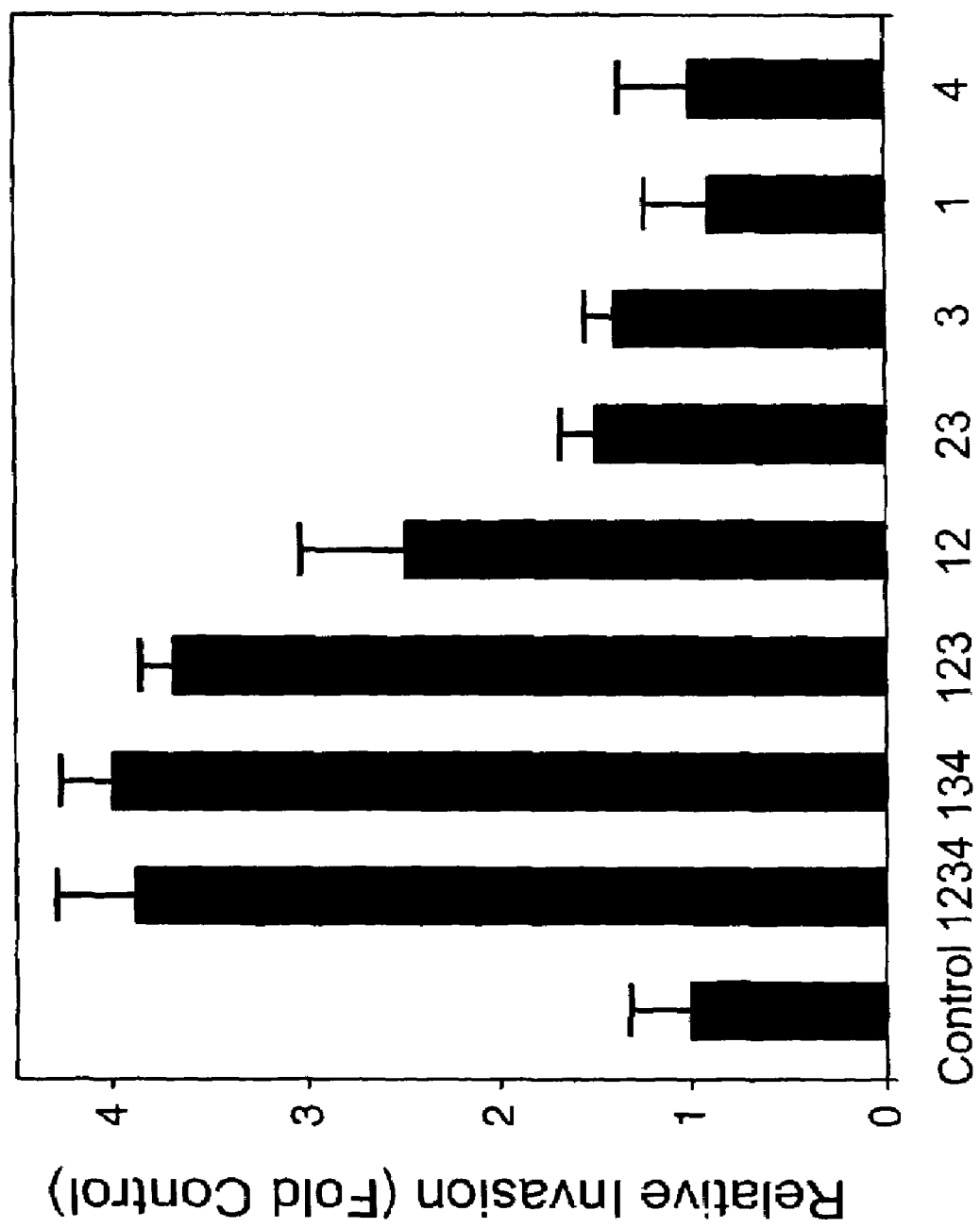
FIG. 27 shows expression as fold invasion compared to a control in which HEK 293 cells transfected with an empty vector were plated in the modified Boyden chamber system. 4T1 cells demonstrated a 4 fold increase invasion when HEK 293 cells expressing constructs WISP-1_1234, WISP-1_134 or WISP-123 were seeded in the lower chamber.

The contribution of the particular WISP-1 domains to the promoted 4T1 cell invasion was evaluated using a Matrigel coated modified Boyden chamber system of 8 µm porosity 24-well format PET membrane filters (BD Biosciences). HEK 293 cells ($20 \times 10^6$) stably expressing the previously mentioned WISP-1 constructs (WISP-1__1234, WISP-1__134, WISP-1__123, WISP-1__12, WISP-1__23, WISP-1__3, WISP-1__1 and WISP-1__4) were seeded in the lower chamber with in 0.75 ml of 50:50 Media (1:1 mixture of DME and Ham's F-12 medium) containing 5% fetal bovine serum and the plates were kept overnight at 37° C. The next day, 4T1 cells (100,000 cells) were added to the upper chamber in 0.5 ml of serum free 50:50 media and the plates were incubated overnight at 37° C. The following day the upper chamber was wiped with a cotton swab and the cells that migrated to the lower side of the insert were stained with the Diff-Quik Stain Kit (Dade Behring Inc.) and counted under the microscope. Triplicate sets of data were averaged for each condition and results are expressed as fold invasion compared to a control in which HEK 293 cells transfected with an empty vector were plated in the lower chamber. 4T1 cells demonstrated a 4 fold increase invasion when HEK 293 cells expressing constructs WISP-1__1234, WISP-1__134 or WISP-123 were seeded in the lower chamber (FIG. 27). HEK 293 cells expressing the construct WISP-1__12 increased 4T1 cells invasion by only 2.5 fold. The increase in 4T1 cell invasion was marginal when HEK 293 cells expressing WISP-1__23, WISP-1__3, WISP-1__1 or WISP-1__4 were plated in the lower chamber. These results suggest that the domain 1 is required for WISP-1 promoted 4T1 cell invasion. In addition, the data shows that WISP-1's domain 1 alone is likely not sufficient to promote 4T1 cell invasion.

Example 25

An assay was conducted to evaluate the antagonistic activity of WISP-1's domain 1 on WISP-1 promoted 4T1 cell invasion. The domain 1 of WISP-1 was cloned into an expression vector immediately upstream of the human IgG$_1$ Fc region sequence. The resulting recombinant fusion protein (WISP-1-domain 1-Fc) was synthesized in a mammalian expression system using Chinese hamster ovary (CHO) cells and purified to homogeneity from conditioned medium by affinity chromatography on a Protein A-Sepharose 4 Fast Flow (Amersham Pharmacia Biotech). WISP-1's domain 1 was also expressed with an amino terminal hexa-histidine tag (WISP-1-domain-1-His) in a CHO expression system and purified to homogeneity from culture supernatant by affinity chromatography on a $Ni^{2+}$-NTA agarose column (Qiagen). Fractions containing the eluted WISP-1-domain-1-His were then pooled and dialyzed.

Figure 28:
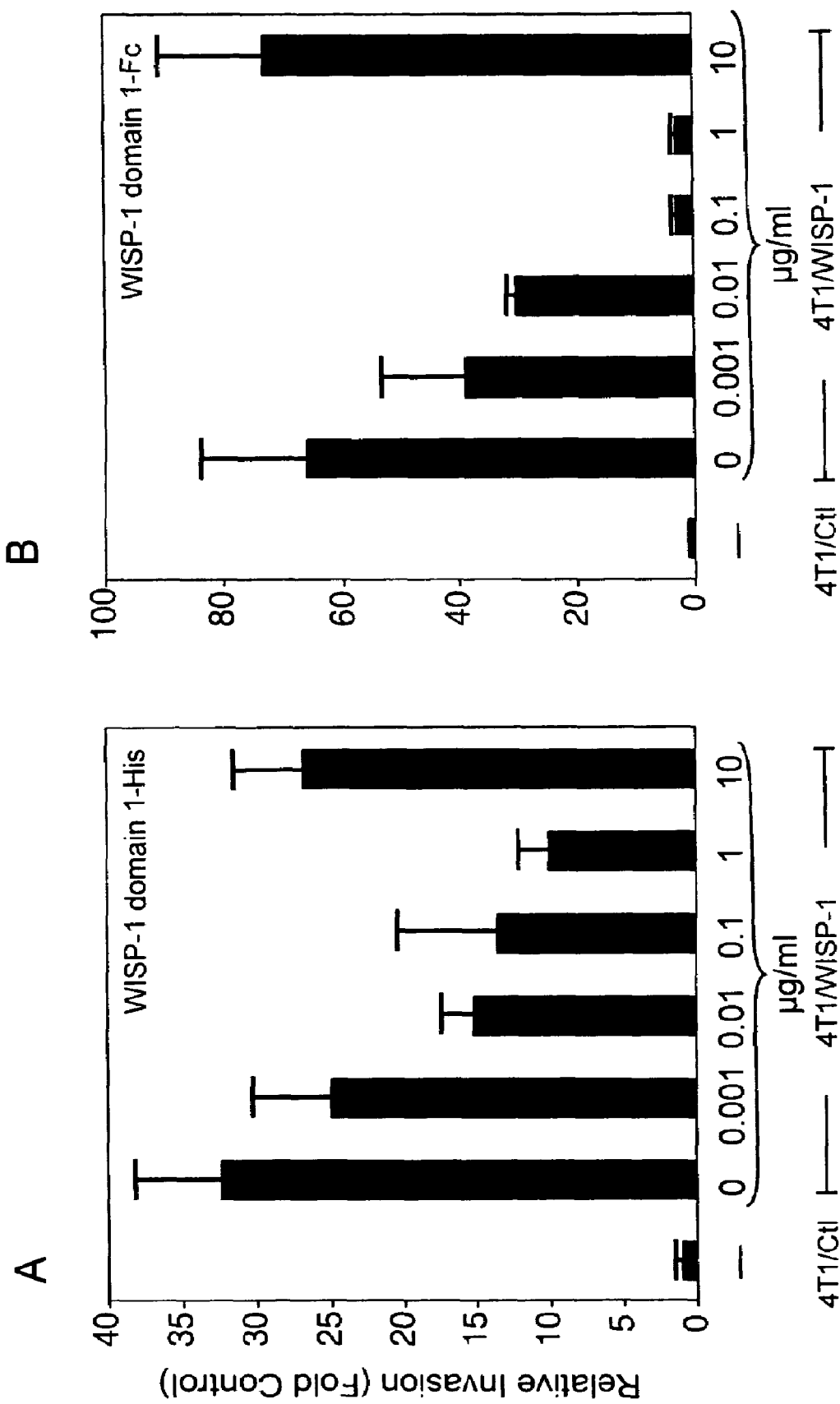
FIGS. 28A-28B illustrate the effects of soluble WISP-1-domain-1 on WISP-1 promoted 4T1 cell invasion, as evaluated using a Matrigel coated modified Boyden chamber system. The results are expressed as relative fold invasion compared to 4T1/control cells. WISP-1-domain-1-His and WISP-1-domain-1-Fc demonstrated a dose dependent antagonistic activity toward WISP-1 promoted 4T1 invasion.

The antagonistic effect of purified soluble WISP-1-domain-1 on WISP-1 promoted 4T1 cell invasion was evaluated using a Matrigel coated modified Boyden chamber system of 8 μm porosity 24-well format PET membrane filters (BD Biosciences). 4T1/control or 4T1/WISP-1 cells (100,000 cells) were added to the upper chamber in 0.5 ml Iscove's Media. The lower chamber was filled with 0.75 ml of the same media containing 5% fetal bovine serum. Various concentrations of WISP-1-domain-1-Fc or WISP-1-domain-1-His were added to the upper and lower chambers and the plates were incubated overnight at 37° C. The next day the upper chamber was wiped with a cotton swab and the cells that migrated to the lower side of the insert were stained with the Diff-Quik Stain Kit (Dade Behring Inc.) and counted under the microscope. Triplicate sets of data were averaged for each condition. The results are expressed as relative fold invasion compared to 4T1/control cells. WISP-1-domain-1-His and WISP-1-domain-1-Fc demonstrated a dose dependent antagonistic activity toward WISP-1 promoted 4T1 invasion (FIG. 28). Both WISP-1-domain-1-His and WISP-1-domain-1-Fc showed an apparent $IC_{50}$ of 0.01 μg/ml. These results suggest that purified WISP-1-domain-1 antagonizes WISP-1 promoted cell invasion.

Example 26

Figure 29:
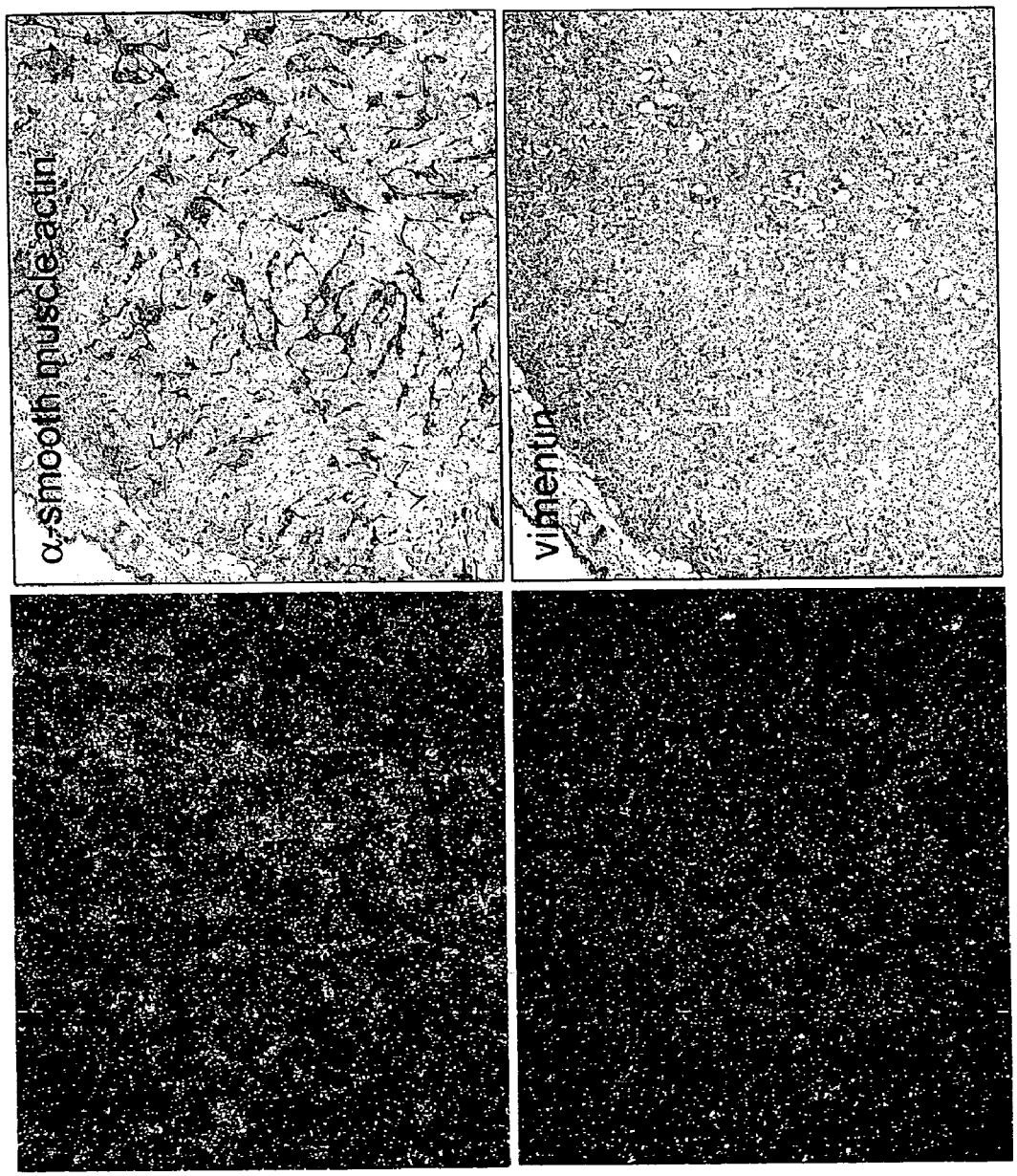
FIG. 29 illustrates an in situ hybridization analysis of tissues from the HPAC xenograft model of human pancreatic adenocarcinomas to evaluate WISP-1 expression.

An animal study was conducted to evaluate WISP-1 expression in the HPAC xenograft model of human pancreatic adenocarcinomas. $5 \times 10^6$ human pancreatic adenocarcinomas cells (HPAC cell line, cat. no. CRL-2119; ATCC, Manassas, Va., USA;) were injected subcutaneously in 6-8 week old female nude mice. After 21 days the mice were sacrificed, the tumors were excised and WISP-1 expression was analyzed by in situ hybridization using a human WISP-1 specific probe and a mouse WISP-1 specific probe (FIG. 29). The results demonstrate a strong mouse WISP-1 expression in areas corresponding to tumor stroma. On the other hand, no human WISP-1 expression was found in the excised tumors. In addition, the tumors revealed a strong α-smooth muscle actin and a weak vimentin immunohistochemical staining over the tumoral stroma. These results indicate that HPAC cells inoculation in nude mice induces the recruitment of a mouse myofibroblastic stroma in which WISP-1 is expressed.

Example 27

An animal study was conducted to evaluate the in vivo efficacy of WISP-1-domain-1 at retarding tumor growth. The human WISP-1_1, WISP-1_12 constructs cloned into an expression vector (pIRES puro2; Clontech Laboratories, Palo Alto, Calif.) were transfected in the HPAC human pancreatic adenocarcinomas cell line. After 48 hours, the culture media was supplemented with 2 μg/ml puromycin. After 2 weeks, the pools of expressing cells were analyzed and the resulting cell lines were maintained in 50:50 media (1:1 mixture of DME and Ham's F-12 medium) supplemented with 10% fetal calf serum (FBS) and 2 μg/ml puromycin.

Figure 30:
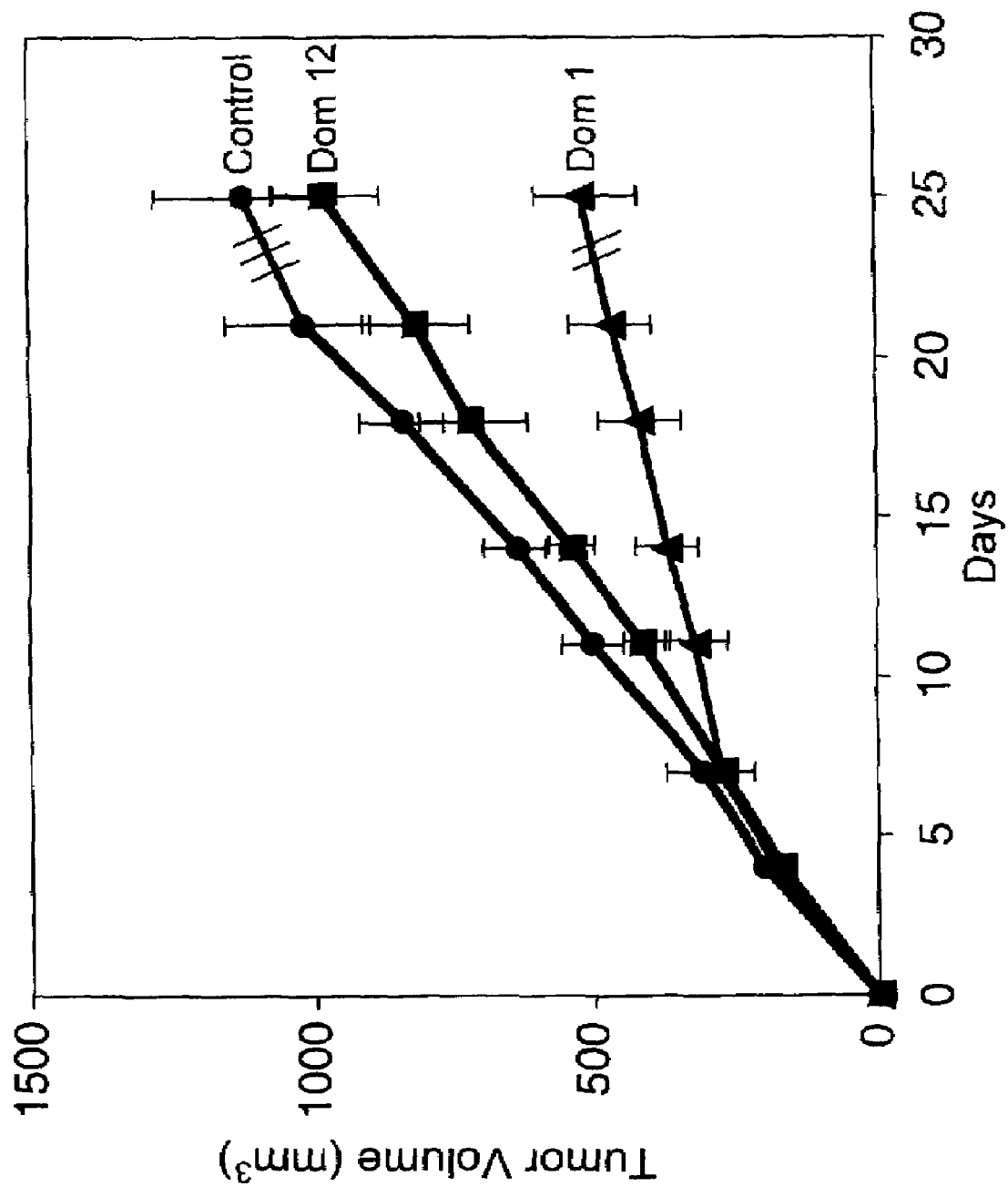
FIG. 30 shows a graph illustrating the effects of WISP-1 constructs on tumor volume in a nude mouse model.

The in vivo efficacy of WISP-1-domain-1 at retarding tumor growth was evaluated by injecting $5 \times 10^6$ cells (HPAC/WISP-1_12, HPAC/WISP-1_1 cells) subcutaneously in 6-8 week old female nude mice (10 mice/group). Tumor volumes were measured twice weekly until day 25. The results demonstrate that the expression of WISP-1_1 or WISP-1_12 in HPAC cells retards their in vivo growth. The tumor volume of HPAC/WISP-1_12 and HPAC/WISP-1_1 cells were 12% and 54% smaller respectively compared to HPAC control cells tumors (FIG. 30). These results indicates that WISP-1-domain-1 and WISP-1-domain-12 expressed by HPAC cells retard their tumor growth possibly by antagonizing mouse WISP-1 tumor promoting activities.

Example 28

Figure 31:
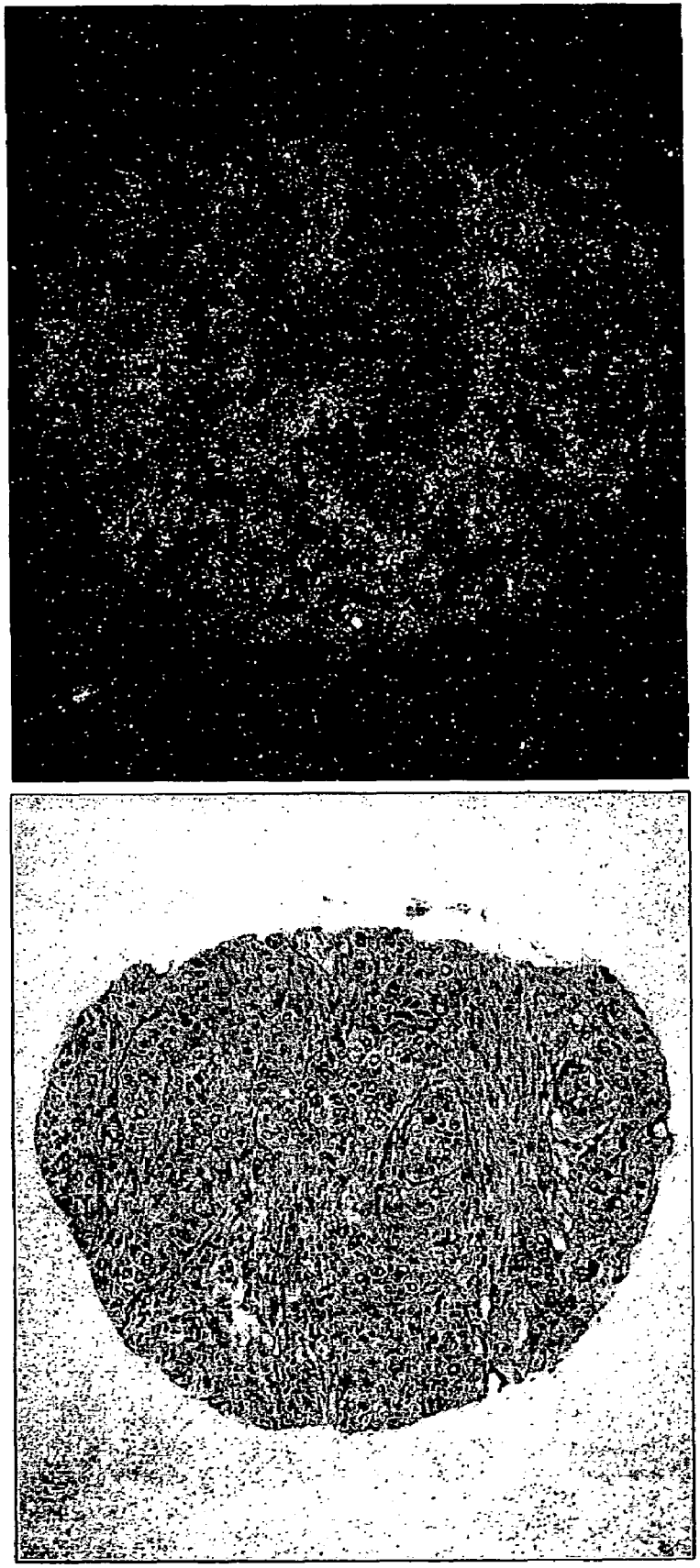
FIG. 31 shows in situ hybridization analyses evaluating WISP-1 expression in primary human pancreatic adenocarcinomas.

In situ hybridization studies were conducted to evaluate WISP-1 expression in primary human pancreatic adenocarcinomas. Using a tumor microarray (TMA), it was shown that 68% (125/184) of the samples cores were positive for WISP-1 expression. In addition, in these samples WISP-1 expression was restricted to the stromal compartment (FIG. 31). These results indicate a high incidence of WISP-1 expression in the stromal compartment of human primary pancreatic tumors.

Example 29

Figure 32:
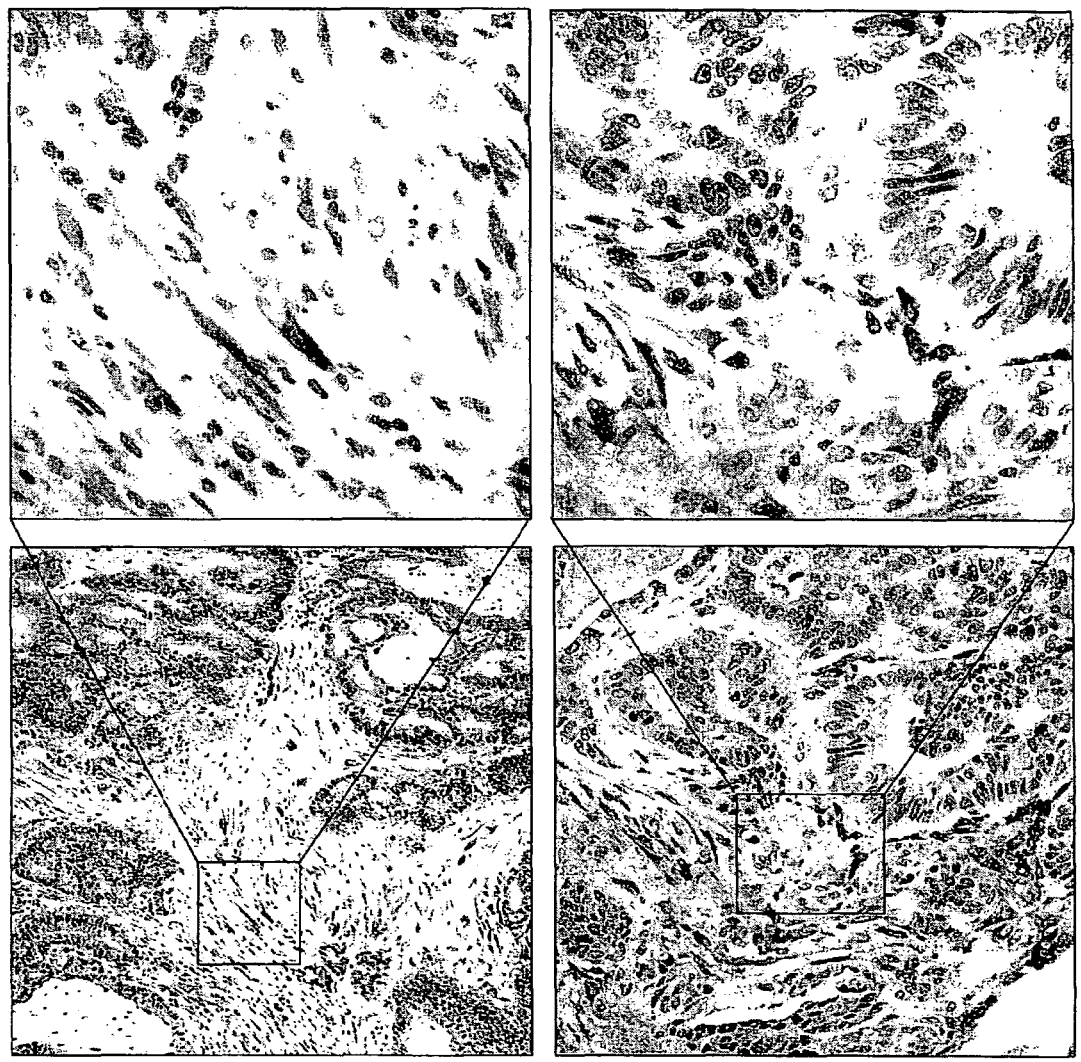
FIG. 32 shows immunohistochemical staining evaluating WISP-1 expression in primary colon adenocarcinomas.

Immunohistochemical staining was conducted to evaluate WISP-1 expression in primary colon adenocarcinomas. A panel of 15 samples of primary human adenocarcinomas were stained for WISP-1 using a WISP-1 specific polyclonal goat antibody (R&D systems; cat. No. AF1627). WISP-1 was detected in 100% (15/15) of the samples analyzed. In all cases WISP-1 was located in the stromal compartment surrounding the tumors (FIG. 32). These results indicate that WISP-1 is prevalent in the stromal compartment of human colon adenocarcinomas.

```
WISP-1 constructs:
Domain 2,3:
                                          (SEQ ID NO: 21)
GAATTCACCATGAGGTGGTTCCTGCCCTGGACGCTGGCAGCAGTGACAGC

AGCAGCCGCCAGCACCGTCCTGGCCACTGCAGTGGTCGGTGTGGGCTGCG

TCCTGGATGGGGTGCGCTACAACAACGGCCAGTCCTTCCAGCCTAACTGC

AAGTACAACTGCACGTGCATCGACGGCGCGGTGGGCTGCACACCACTGTG

CCTCCGAGTGCGCCCCCCGCGTCTCTGGTGCCCCCACCCGCGGCGCGTGA

GCATACCTGGCCACTGCTGTGAGCAGTGGGTATGTGAGGACGACGCCAAG

AGGCCACGCAAGACCGCACCCCGTGACACAGGAGCCTTCGATGCTGTGGG

TGAGGTGGAGGCATGGCACAGGAACTGCATAGCCTACACAAGCCCTGGA

GCCCTTGCTCCACCAGCTGCGGCCTGGGGGTCTCCACTCGGATCTCCAAT

GTTAACGCCCAGTGCTGGCCTGAGCAAGAGAGCCGCCTCTGCAACTTGCG

GCCATGCGATGTGGACATCCATACACTCATTAAGGCGGCCGCACACCACC

ATCACCATCACCATCACTAAGTGAGGCCGCATAGATAACTGATCCAGTGT

GCTGGAATTAATTCGCTGTCTGCGA

Domain 1-IgG:
                                          (SEQ ID NO: 22)
CCTCGGTTCTATCGATTGAATTCCACCATGAGGTGGTTCCTGCCCTGGAC

GCTGGCAGCAGTGACAGCAGCAGCCGCCAGCACCGTCCTGGCCACGGCCC
```

-continued

```
TCTCTCCAGCCCCTACGACCATGGACTTTACTCCAGCTCCACTGGAGGAC

ACCTCCTCACGCCCCCAATTCTGCAAGTGGCCATGTGAGTGCCCGCCATC

CCCACCCCGCTGCCCGCTGGGGGTCAGCCTCATCACAGATGGCTGTGAGT

GCTGTAAGATGTGCGCTCAGCAGCTTGGGGACAACTGCACGGAGGCTGCC

ATCTGTGACCCCCACCGGGGCCTCTACTGTGACTACAGCGGGGACCGCCC

GAGGTACGCAATAGGAGTGTGTGCACAGGTGGTCGGTGTGGGGGTCACCG

ACAAAACTCACACATGCCCACCGTGCCCAGCACCTGAACTCCTGGGGGGA

CCGTCAGTCTTCCTCTTCCCCCCAAAACCCAAGGACACCCTCATGATCTC

CCGGACCCCTGAGGTCACATGCGTGGTGGTGGACGTGAGCCACGAAGACC

CTGAGGTCAAGTTCAACTGGTACGTGGACGGCGTGGAGGTGCATAATGCC

AAGACAAAGCCGCGGGAGGAGCAGTACAACAGCACGTACCGTGTGGTCAG

CGTCCTCACCGTCCTGCACCAGGACTGGCTGAATGGCAAGGAGTACAAGT

GCAAGGTCTCCAACAAAGCCCTCCCAGCCCCCATCGAGAAAACCATCTCC

AAAGCCAAAGGGCAGCCCCGAGAACCACAGGTGTACACCCTGCCCCCATC

CCGGGAAGAGATGACCAAGAACCAGGTCAGCCTGACCTGCCTGGTCAAAG

GCTTCTATCCCAGCGACATCGCCGTGGAGTGGGAGAGCAATGGGCAGCCG

GAGAACAACTACAAGACCACGCCTCCCGTGCTGGACTCCGACGGCTCCTT

CTTCCTCTACAGCAAGCTCACCGTGGACAAGAGCAGGTGGCAGCAGGGGA

ACGTCTTCTCATGCTCCGTGATGCATGAGGCTCTGCACAACCACTACACG

CAGAAGAGCCTCTCCCTGTCTCCGGGTAAATGAGTGCGACGGCCCTAGAG

TCGACCTGCAGAAGCTTGGCCGCCATGGCCC
```

Deposit of Material

The following materials have been deposited with the American Type Culture Collection, 10801 University Blvd., Manassas, Va. 20110-2209, USA (ATCC):

| Material | ATCC Dep. No. | Deposit Date |
|---|---|---|
| 3D11.D7 | PTA-4624 | Sep. 4, 2002 |
| 11C2.C10 | PTA-4628 | Sep. 4, 2002 |
| 9C10.F5 | PTA-4626 | Sep. 4, 2002 |
| 5D4.F6 | PTA-4625 | Sep. 4, 2002 |
| 9C11.C7 | PTA-4627 | Sep. 4, 2002 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC '122 and the Commissioner's rules pursuant thereto (including 37 CFR '1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written description is considered to be sufficient to enable one skilled in the art to practice the invention. The present invention is not to be limited in scope by the example presented herein. Indeed, various modifications of the invention in addition to those shown and described herein will become apparent to those skilled in the art from the foregoing description and fall within the scope of the appended claims.

---

What is claimed is:

1. An isolated WISP-1-domain 1 polypeptide consisting of amino acids 24-117 of SEQ ID NO:1.

2. The WISP-1-domain 1 polypeptide of claim 1, wherein said polypeptide is fused to a Fc region of an immunoglobulin.

3. An isolated WISP-1-domain 1 polypeptide, wherein said WISP-1-domain 1 polypeptide is at least about 95% identical to amino acids 24-117 of SEQ ID NO:1 and wherein said WISP-1-domain 1 polypeptide inhibits the motility of pancreatic cancer cells, colon or colorectal cancer cells, breast cancer cells, lung cancer cells, and/or brain cancer cells.

4. The WISP-1-domain 1 polypeptide of claim 3 wherein said WISP-1-domain 1 polypeptide is fused to a Fc region of an immunoglobulin.

5. A composition comprising a WISP-1-domain 1 polypeptide, wherein said WISP-1-domain 1 polypeptide consists of amino acids 24-117 of SEQ ID NO:1.

6. The composition of claim 5, wherein said polypeptide is fused to a Fc region of an immunoglobulin.

7. A composition comprising a WISP-1-domain 1 polypeptide, wherein said WISP-1-domain 1 polypeptide is at least about 95% identical to amino acids 24-117 of SEQ ID NO:1 and wherein said WISP-1-domain 1 polypeptide inhibits the motility of pancreatic cancer cells, colon or colorectal cancer cells, breast cancer cells, lung cancer cells, and/or brain cancer cells.

8. The composition of claim 7, wherein said WISP-1-domain 1 polypeptide is fused to a Fc region of an immunoglobulin.

9. A method of treating pancreatic cancer, colon or colorectal cancer, breast cancer, lung cancer, or brain cancer in a mammal, comprising administering to said mammal an effective amount of a WISP-1-domain 1 polypeptide consisting essentially of amino acids 24-117 of SEQ ID NO:1.

10. The method of claim 9, wherein said WISP-1-domain 1 polypeptide is fused to a Fc region of an immunoglobulin.

11. The method of claim 9, wherein said cancer is pancreatic adenocarcinoma or colonic adenocarcinoma.

12. The method of claim 9, wherein said polypeptide inhibits or reduces cancer cell growth or metastasis.

13. The method of claim 9, wherein said polypeptide inhibits or reduces lung cancer cell metastasis at a site in the mammal secondary or different from the primary lung tumor site in the mammal.

14. The method of claim 9, wherein chemotherapy, radiation, a prodrug, a cytotoxic agent, a growth inhibitory agent, or a cytokine is also administered to said mammal.

15. A method of inhibiting cancer cell motility, comprising exposing a pancreatic cancer cell, colon or colorectal cancer cell, breast cancer cell, lung cancer cell, or brain cancer cell to an effective amount of a WISP-1-domain 1 polypeptide consisting essentially of amino acids 24-117 of SEQ ID NO:1.

16. The method of claim 15, wherein said WISP-1-domain 1 polypeptide is fused to a Fc region of an immunoglobulin.

17. A method of inhibiting cancer cell motility in a mammal comprising administering to said mammal an effective amount of a WISP-1-domain 1 polypeptide consisting essentially of amino acids 24-117 of SEQ ID NO:1,
wherein said cancer cell is selected from the group consisting of a pancreatic cancer cell, colon or colorectal cancer cell, breast cancer cell, lung cancer cell, or brain cancer cell.

18. The method of claim 17, wherein said WISP-1-domain 1 polypeptide is fused to a Fc region of an immunoglobulin.

19. A method of treating pancreatic cancer, colon or colorectal cancer, breast cancer, lung cancer, or brain cancer in a mammal, comprising administering to said mammal an effective amount of a WISP-1-domain 1 polypeptide, wherein said WISP-1-domain 1 polypeptide is at least about 95% identical to amino acids 24-117 of SEQ ID NO:1 and wherein said WISP-1-domain 1 polypeptide inhibits the motility of pancreatic cancer cells, colon or colorectal cancer cells, breast cancer cells, lung cancer cells, and/or brain cancer cells.

20. The method of claim 19, wherein said WISP-1-domain 1 polypeptide is fused to a Fc region of an immunoglobulin.

21. The method of claim 19, wherein said cancer is pancreatic adenocarcinoma or colonic adenocarcinoma.

22. The method of claim 19, wherein said polypeptide inhibits or reduces cancer cell growth or metastasis.

23. The method of claim 19, wherein said polypeptide inhibits or reduces lung cancer cell metastasis at a site in the mammal secondary or different from the primary lung tumor site in the mammal.

24. The method of claim 19, wherein chemotherapy, radiation, a prodrug, a cytotoxic agent, a growth inhibitory agent, or a cytokine is also administered to said mammal.

25. A method of inhibiting cancer cell motility, comprising exposing a pancreatic cancer cell, colon or colorectal cancer cell, breast cancer cell, lung cancer cell, or brain cancer cell to an effective amount of a WISP-1-domain 1 polypeptide, wherein said WISP-1-domain 1 polypeptide is at least about 95% identical to amino acids 24-117 of SEQ ID NO:1 and wherein said WISP-1-domain 1 polypeptide inhibits the motility of pancreatic cancer cells, colon or colorectal cancer cells, breast cancer cells, lung cancer cells, and/or brain cancer cells.

26. The method of claim 25, wherein said WISP-1-domain 1 polypeptide is fused to a Fc region of an immunoglobulin.

27. A method of inhibiting cancer cell motility in a mammal comprising administering to said mammal an effective amount of a WISP-1-domain 1 polypeptide, wherein said WISP-1-domain 1 polypeptide is at least about 95% identical to amino acids 24-117 of SEQ ID NO:1 and wherein said WISP-1-domain 1 polypeptide inhibits the motility of said cancer cell, and further wherein said cancer cell is selected from the group consisting of a pancreatic cancer cell, colon or colorectal cancer cell, breast cancer cell, lung cancer cell, or brain cancer cell.

28. The method of claim 27, wherein said WISP-1-domain 1 polypeptide is fused to a Fc region of an immunoglobulin.

* * * * *

SEQUENCE LISTING

```
<160> NUMBER OF SEQ ID NOS: 22

<210> SEQ ID NO 1
<211> LENGTH: 367
<212> TYPE: PRT
<213> ORGANISM: Homo sapiens

<400> SEQUENCE: 1

Met Arg Trp Phe Leu Pro Trp Thr Leu Ala Ala Val Thr Ala Ala
1               5                   10                  15

Ala Ala Ser Thr Val Leu Ala Thr Ala Leu Ser Pro Ala Pro Thr
            20                  25                  30

Thr Met Asp Phe Thr Pro Ala Pro Leu Glu Asp Thr Ser Ser Arg
            35                  40                  45

Pro Gln Phe Cys Lys Trp Pro Cys Glu Cys Pro Pro Ser Pro Pro
    50                  55                  60
```

-continued

```
Arg Cys Pro Leu Gly Val Ser Leu Ile Thr Asp Gly Cys Glu Cys
 65                  70                  75

Cys Lys Met Cys Ala Gln Gln Leu Gly Asp Asn Cys Thr Glu Ala
                 80                  85                  90

Ala Ile Cys Asp Pro His Arg Gly Leu Tyr Cys Asp Tyr Ser Gly
             95                 100                 105

Asp Arg Pro Arg Tyr Ala Ile Gly Val Cys Ala Gln Val Val Gly
         110                 115                 120

Val Gly Cys Val Leu Asp Gly Val Arg Tyr Asn Asn Gly Gln Ser
     125                 130                 135

Phe Gln Pro Asn Cys Lys Tyr Asn Cys Thr Cys Ile Asp Gly Ala
140                 145                 150

Val Gly Cys Thr Pro Leu Cys Leu Arg Val Arg Pro Arg Leu
                155                 160                 165

Trp Cys Pro His Pro Arg Arg Val Ser Ile Pro Gly His Cys Cys
                170                 175                 180

Glu Gln Trp Val Cys Glu Asp Ala Lys Arg Pro Arg Lys Thr
            185                 190                 195

Ala Pro Arg Asp Thr Gly Ala Phe Asp Ala Val Gly Glu Val Glu
200                 205                 210

Ala Trp His Arg Asn Cys Ile Ala Tyr Thr Ser Pro Trp Ser Pro
215                 220                 225

Cys Ser Thr Ser Cys Gly Leu Gly Val Ser Thr Arg Ile Ser Asn
                230                 235                 240

Val Asn Ala Gln Cys Trp Pro Glu Gln Glu Ser Arg Leu Cys Asn
                245                 250                 255

Leu Arg Pro Cys Asp Val Asp Ile His Thr Leu Ile Lys Ala Gly
            260                 265                 270

Lys Lys Cys Leu Ala Val Tyr Gln Pro Glu Ala Ser Met Asn Phe
    275                 280                 285

Thr Leu Ala Gly Cys Ile Ser Thr Arg Ser Tyr Gln Pro Lys Tyr
290                 295                 300

Cys Gly Val Cys Met Asp Asn Arg Cys Cys Ile Pro Tyr Lys Ser
                305                 310                 315

Lys Thr Ile Asp Val Ser Phe Gln Cys Pro Asp Gly Leu Gly Phe
            320                 325                 330

Ser Arg Gln Val Leu Trp Ile Asn Ala Cys Phe Cys Asn Leu Ser
        335                 340                 345

Cys Arg Asn Pro Asn Asp Ile Phe Ala Asp Leu Glu Ser Tyr Pro
    350                 355                 360

Asp Phe Ser Glu Ile Ala Asn
365
```

```
<210> SEQ ID NO 2
<211> LENGTH: 2830
<212> TYPE: DNA
<213> ORGANISM: Homo sapiens

<400> SEQUENCE: 2
cccacgcgtc cgctgggccc agctcccccg agaggtggtc ggatcctctg        50
ggctgctcgg tcgatgcctg tgccactgac gtccaggcat gaggtggttc       100
ctgccctgga cgctggcagc agtgacagca gcagccgcca gcaccgtcct       150
ggccacggcc ctctctccag cccctacgac catggacttt actccagctc      200
```

| | |
|---|---|
| cactggagga cacctcctca cgccccaat tctgcaagtg gccatgtgag | 250 |
| tgcccgccat ccccacccg ctgcccgctg ggggtcagcc tcatcacaga | 300 |
| tggctgtgag tgctgtaaga tgtgcgctca gcagcttggg gacaactgca | 350 |
| cggaggctgc catctgtgac ccccaccggg gcctctactg tgactacagc | 400 |
| ggggaccgcc cgaggtacgc aataggagtg tgtgcacagg tggtcggtgt | 450 |
| gggctgcgtc ctggatgggg tgcgctacaa caacggccag tccttccagc | 500 |
| ctaactgcaa gtacaactgc acgtgcatcg acggcgcggt gggctgcaca | 550 |
| ccactgtgcc tccgagtgcg cccccgcgt ctctggtgcc cccacccgcg | 600 |
| gcgcgtgagc atacctggcc actgctgtga gcagtgggta tgtgaggacg | 650 |
| acgccaagag gccacgcaag accgcacccc gtgacacagg agccttcgat | 700 |
| gctgtgggtg aggtggaggc atggcacagg aactgcatag cctacacaag | 750 |
| cccctggagc ccttgctcca ccagctgcgg cctgggggtc tccactcgga | 800 |
| tctccaatgt taacgcccag tgctggcctg agcaagagag ccgcctctgc | 850 |
| aacttgcggc catgcgatgt ggacatccat acactcatta aggcagggaa | 900 |
| gaagtgtctg gctgtgtacc agccagaggc atccatgaac ttcacacttg | 950 |
| cgggctgcat cagcacacgc tcctatcaac ccaagtactg tggagtttgc | 1000 |
| atggacaata ggtgctgcat cccctacaag tctaagacta tcgacgtgtc | 1050 |
| cttccagtgt cctgatgggc ttggcttctc ccgccaggtc ctatggatta | 1100 |
| atgcctgctt ctgtaacctg agctgtagga atcccaatga catctttgct | 1150 |
| gacttggaat cctaccctga cttctcagaa attgccaact aggcaggcac | 1200 |
| aaatcttggg tcttggggac taacccaatg cctgtgaagc agtcagccct | 1250 |
| tatggccaat aacttttcac caatgagcct tagttaccct gatctggacc | 1300 |
| cttggcctcc atttctgtct ctaaccattc aaatgacgcc tgatggtgct | 1350 |
| gctcaggccc atgctatgag ttttctcctt gatatcattc agcatctact | 1400 |
| ctaaagaaaa atgcctgtct ctagctgttc tggactacac ccaagcctga | 1450 |
| tccagccttt ccaagtcact agaagtcctg ctggatcttg cctaaatccc | 1500 |
| aagaaatgga atcaggtaga cttttaatat cactaatttc ttctttagat | 1550 |
| gccaaaccac aagactcttt gggtccattc agatgaatag atggaatttg | 1600 |
| gaacaataga ataatctatt atttggagcc tgccaagagg tactgtaatg | 1650 |
| ggtaattctg acgtcagcgc accaaaacta tcctgattcc aaatatgtat | 1700 |
| gcacctcaag gtcatcaaac atttgccaag tgagttgaat agttgcttaa | 1750 |
| ttttgatttt taatgaaaag ttgtatccat taacctgggc attgttgagg | 1800 |
| ttaagttct cttcacccct acactgtgaa gggtacagat taggtttgtc | 1850 |
| ccagtcagaa ataaaatttg ataaacattc ctgttgatgg gaaaagcccc | 1900 |
| cagttaatac tccagagaca gggaaaggtc agcccatttc agaaggacca | 1950 |
| attgactctc acactgaatc agctgctgac tggcagggct ttgggcagtt | 2000 |
| ggccaggctc ttccttgaat cttctcccctt gtcctgcttg ggttcatagg | 2050 |
| aattggtaag gcctctggac tggcctgtct ggcccctgag agtggtgccc | 2100 |
| tggaacactc ctctactctt acagagcctt gagagaccca gctgcagacc | 2150 |
| atgccagacc cactgaaatg accaagacag gttcaggtag gggtgtgggt | 2200 |

| | |
|---|---|
| caaaccaaga agtgggtgcc cttggtagca gcctggggtg acctctagag | 2250 |
| ctggaggctg tgggactcca ggggcccccg tgttcaggac acatctattg | 2300 |
| cagagactca tttcacagcc tttcgttctg ctgaccaaat ggccagtttt | 2350 |
| ctggtaggaa gatggaggtt taccagttgt ttagaaacag aaatagactt | 2400 |
| aataaaggtt taaagctgaa gaggttgaag ctaaaaggaa aaggttgttg | 2450 |
| ttaatgaata tcaggctatt atttattgta ttaggaaaat ataatattta | 2500 |
| ctgttagaat tcttttattt agggcctttt ctgtgccaga cattgctctc | 2550 |
| agtgctttgc atgtattagc tcactgaatc ttcacgacaa tgttgagaag | 2600 |
| ttcccattat tatttctgtt cttacaaatg tgaaacggaa gctcatagag | 2650 |
| gtgagaaaac tcaaccagag tcacccagtt ggtgactggg aaagttagga | 2700 |
| ttcagatcga aattggactg tctttataac ccatattttc cccctgtttt | 2750 |
| tagagcttcc aaatgtgtca gaataggaaa acattgcaat aaatggcttg | 2800 |
| atttttttaaa aaaaaaaaa aaaaaaaaa | 2830 |

<210> SEQ ID NO 3
<211> LENGTH: 440
<212> TYPE: DNA
<213> ORGANISM: Homo sapiens

<400> SEQUENCE: 3

| | |
|---|---|
| gaattcacca tgaggtggtt cctgccctgg acgctggcag cagtgacagc | 50 |
| agcagccgcc agcaccgtcc tggccacggc cctctctcca gcccctacga | 100 |
| ccatggactt tactccagct ccactggagg acacctcctc acgccccaa | 150 |
| ttctgcaagt ggccatgtga gtgcccgcca tccccacccc gctgcccgct | 200 |
| gggggtcagc ctcatcacag atggctgtga gtgctgtaag atgtgcgctc | 250 |
| agcagcttgg ggacaactgc acggaggctg ccatctgtga ccccaccgg | 300 |
| ggcctctact gtgactacag cggggaccgc ccgaggtacg caataggagt | 350 |
| gtgtgcacag gcggccgcac accaccatca ccatcaccat cactaagtga | 400 |
| ggccgcatag ataactgatc cagtgtgctg gaattaattc | 440 |

<210> SEQ ID NO 4
<211> LENGTH: 340
<212> TYPE: DNA
<213> ORGANISM: Homo sapiens

<400> SEQUENCE: 4

| | |
|---|---|
| gaattcacca tgaggtggtt cctgccctgg acgctggcag cagtgacagc | 50 |
| agcagccgcc agcaccgtcc tggccactgc agtggtcggt gtgggctgcg | 100 |
| tcctggatgg ggtgcgctac aacaacggcc agtccttcca gcctaactgc | 150 |
| aagtacaact gcacgtgcat cgacggcgcg gtgggctgca caccactgtg | 200 |
| cctccgagtg cgccccccgc gtctctggtg cccccacccg cggcgcgtga | 250 |
| gcatacctgg ccactgctgt gagcagtggg tatgtgcggc cgcacaccac | 300 |
| catcaccatc accatcacta agtgaggccg catagataac | 340 |

<210> SEQ ID NO 5
<211> LENGTH: 321
<212> TYPE: DNA

<213> ORGANISM: Homo sapiens

<400> SEQUENCE: 5

```
gaattcacca tgaggtggtt cctgccctgg acgctggcag cagtgacagc         50
agcagccgcc agcaccgtcc tggccactgc agcatggcac aggaactgca        100
tagcctacac aagcccctgg agcccttgct ccaccagctg cggcctgggg        150
gtctccactc ggatctccaa tgttaacgcc cagtgctggc ctgagcaaga        200
gagccgcctc tgcaacttgc ggccatgcga tgtggacatc catacactca        250
ttaaggcggc cgcacaccac catcaccatc accatcacta gtgaggccg         300
catagataac tgatccagtg  t                                      321
```

<210> SEQ ID NO 6
<211> LENGTH: 442
<212> TYPE: DNA
<213> ORGANISM: Homo sapiens

<400> SEQUENCE: 6

```
gaattcacca tgaggtggtt cctgccctgg acgctggcag cagtgacagc         50
agcagccgcc agcaccgtcc tggccactgc agggaagaag tgtctggctg        100
tgtaccagcc agaggcatcc atgaacttca cacttgcggg ctgcatcagc        150
acacgctcct atcaacccaa gtactgtgga gtttgcatgg acaataggtg        200
ctgcatcccc tacaagtcta agactatcga cgtgtccttc cagtgtcctg        250
atgggcttgg cttctcccgc caggtcctat ggattaatgc ctgcttctgt        300
aacctgagct gtaggaatcc caatgacatc tttgctgact tggaatccta        350
ccctgacttc tcagaaattg ccaacgcggc cgcacaccac catcaccatc        400
accatcacta gtgaggccg catagataac tgatccagtg  tg               442
```

<210> SEQ ID NO 7
<211> LENGTH: 619
<212> TYPE: DNA
<213> ORGANISM: Homo sapiens

<400> SEQUENCE: 7

```
gaattcacca tgaggtggtt cctgccctgg acgctggcag cagtgacagc         50
agcagccgcc agcaccgtcc tggccacggc cctctctcca gcccctacga        100
ccatggactt tactccagct ccactggagg acacctcctc acgcccccaa        150
ttctgcaagt ggccatgtga gtgcccgcca tccccacccc gctgcccgct        200
gggggtcagc ctcatcacag atggctgtga gtgctgtaag atgtgcgctc        250
agcagcttgg ggacaactgc acggaggctg ccatctgtga cccccaccgg        300
ggcctctact gtgactacag cggggaccgc ccgaggtacg caataggagt        350
gtgtgcacag gtggtcggtg tgggctgcgt cctggatggg gtgcgctaca        400
acaacggcca gtccttccag cctaactgca agtacaactg cacgtgcatc        450
gacggcgcgg tgggctgcac accactgtgc ctccgagtgc gccccccgcg        500
tctctggtgc ccccacccgc ggcgcgtgag catacctggc cactgctgtg        550
agcagtgggt atgtgcggcc gcacaccacc atcaccatca ccatcactaa        600
gtgaggccgc  atagataac                                         619
```

<210> SEQ ID NO 8
<211> LENGTH: 885
<212> TYPE: DNA
<213> ORGANISM: Homo sapiens

<400> SEQUENCE: 8

| | | |
|---|---|---|
| gaattcacca tgaggtggtt cctgccctgg acgctggcag cagtgacagc | 50 |
| agcagccgcc agcaccgtcc tggccacggc cctctctcca gcccctacga | 100 |
| ccatggactt tactccagct ccactggagg acacctcctc acgccccaa | 150 |
| ttctgcaagt ggccatgtga gtgcccgcca tccccacccc gctgcccgct | 200 |
| gggggtcagc ctcatcacag atggctgtga gtgctgtaag atgtgcgctc | 250 |
| agcagcttgg ggacaactgc acggaggctg ccatctgtga cccccaccgg | 300 |
| ggcctctact gtgactacag cggggaccgc ccgaggtacg caataggagt | 350 |
| gtgtgcacag gtggtcggtg tgggctgcgt cctggatggg gtgcgctaca | 400 |
| acaacggcca gtccttccag cctaactgca agtacaactg cacgtgcatc | 450 |
| gacggcgcgg tgggctgcac accactgtgc ctccgagtgc gccccccgcg | 500 |
| tctctggtgc ccccacccgc ggcgcgtgag catacctggc cactgctgtg | 550 |
| agcagtgggt atgtgaggac gacgccaaga ggccacgcaa gaccgcaccc | 600 |
| cgtgacacag gagccttcga tgctgtgggt gaggtggagg catggcacag | 650 |
| gaactgcata gcctacacaa gccctggag cccttgctcc accagctgcg | 700 |
| gcctggggt ctccactcgg atctccaatg ttaacgccca gtgctggcct | 750 |
| gagcaagaga gccgcctctg caacttgcgg ccatgcgatg tggacatcca | 800 |
| tacactcatt aaggcggccg cacaccacca tcaccatcac catcactaag | 850 |
| tgaggccgca tagataactg atccagtgtg ctgga | 885 |

<210> SEQ ID NO 9
<211> LENGTH: 1014
<212> TYPE: DNA
<213> ORGANISM: Homo sapiens

<400> SEQUENCE: 9

| | | |
|---|---|---|
| gaattcacca tgaggtggtt cctgccctgg acgctggcag cagtgacagc | 50 |
| agcagccgcc agcaccgtcc tggccacggc cctctctcca gcccctacga | 100 |
| ccatggactt tactccagct ccactggagg acacctcctc acgccccaa | 150 |
| ttctgcaagt ggccatgtga gtgcccgcca tccccacccc gctgcccgct | 200 |
| gggggtcagc ctcatcacag atggctgtga gtgctgtaag atgtgcgctc | 250 |
| agcagcttgg ggacaactgc acggaggctg ccatctgtga cccccaccgg | 300 |
| ggcctctact gtgactacag cggggaccgc ccgaggtacg caataggagt | 350 |
| gtgtgcacag gtggtcggtg tgggctgcgt cctggatggg gtgcgctaca | 400 |
| acaacggcca gtccttccag cctaactgca agtacaactg cacgtgcatc | 450 |
| gacggcgcgg tgggctgcac accactgtgc ctccgagtgc gccccccgcg | 500 |
| tctctggtgc ccccacccgc ggcgcgtgag catacctggc cactgctgtg | 550 |
| agcagtgggt atgtctgcag gcagggaaga agtgtctggc tgtgtaccag | 600 |
| ccagaggcat ccatgaactt cacacttgcg ggctgcatca gcacacgctc | 650 |
| ctatcaaccc aagtactgtg gagtttgcat ggacaatagg tgctgcatcc | 700 |

| | |
|---|---|
| cctacaagtc taagactatc gacgtgtcct tccagtgtcc tgatgggctt | 750 |
| ggcttctccc gccaggtcct atggattaat gcctgcttct gtaacctgag | 800 |
| ctgtaggaat cccaatgaca tctttgctga cttggaatcc taccctgact | 850 |
| tctcagaaat tgccaacgcg gccgcacacc accatcacca tcaccatcac | 900 |
| taagtgaggc cgcatagata actgatccag tgtgctggaa ttaattcgct | 950 |
| gtctgcgagg gccagctgtt ggggtgagta ctccctctca aaagcgggca | 1000 |
| tgacttctgc gcta | 1014 |

<210> SEQ ID NO 10
<211> LENGTH: 904
<212> TYPE: DNA
<213> ORGANISM: Homo sapiens

<400> SEQUENCE: 10

| | |
|---|---|
| gaattcacca tgaggtggtt cctgccctgg acgctggcag cagtgacagc | 50 |
| agcagccgcc agcaccgtcc tggccacggc cctctctcca gcccctacga | 100 |
| ccatggactt tactccagct ccactggagg acacctcctc acgccccaa | 150 |
| ttctgcaagt ggccatgtga gtgcccgcca tccccacccc gctgcccgct | 200 |
| gggggtcagc ctcatcacag atggctgtga gtgctgtaag atgtgcgctc | 250 |
| agcagcttgg ggacaactgc acggaggctg ccatctgtga cccccaccgg | 300 |
| ggcctctact gtgactacag cggggaccgc ccgaggtacg caataggagt | 350 |
| gtgtgcgcat gctgtgggtg aggtggaggc atggcacagg aactgcatag | 400 |
| cctacacaag cccctggagc ccttgctcca ccagctgcgg cctgggggtc | 450 |
| tccactcgga tctccaatgt taacgcccag tgctggcctg agcaagagag | 500 |
| ccgcctctgc aacttgcggc catgcgatgt ggacatccat acactcatta | 550 |
| aggcagggaa gaagtgtctg ctgtgtacc agccagaggc atccatgaac | 600 |
| ttcacacttg cgggctgcat cagcacacgc tcctatcaac ccaagtactg | 650 |
| tggagtttgc atggacaata ggtgctgcat cccctacaag tctaagacta | 700 |
| tcgacgtgtc cttccagtgt cctgatgggc ttggcttctc ccgccaggtc | 750 |
| ctatggatta atgcctgctt ctgtaacctg agctgtagga atcccaatga | 800 |
| catctttgct gacttggaat cctaccctga cttctcagaa attgccaacg | 850 |
| cggccgcaca ccaccatcac catcaccatc actaagtgag gccgcataga | 900 |
| taac | 904 |

<210> SEQ ID NO 11
<211> LENGTH: 922
<212> TYPE: DNA
<213> ORGANISM: Homo sapiens

<400> SEQUENCE: 11

| | |
|---|---|
| gaattcacca tgaggtggtt cctgccctgg acgctggcag cagtgacagc | 50 |
| agcagccgcc agcaccgtcc tggccactgc agtggtcggt gtgggctgcg | 100 |
| tcctggatgg ggtgcgctac aacaacggcc agtccttcca gcctaactgc | 150 |
| aagtacaact gcacgtgcat cgacggcgcg gtgggctgca caccactgtg | 200 |
| cctccgagtg cgcccccgc gtctctggtg ccccaccg cggcgcgtga | 250 |
| gcatacctgg ccactgctgt gagcagtggg tatgtgagga cgacgccaag | 300 |

-continued

| | |
|---|---|
| aggccacgca agaccgcacc ccgtgacaca ggagccttcg atgctgtggg | 350 |
| tgaggtggag gcatggcaca ggaactgcat agcctacaca agcccctgga | 400 |
| gcccttgctc caccagctgc ggcctggggg tctccactcg gatctccaat | 450 |
| gttaacgccc agtgctggcc tgagcaagag agccgcctct gcaacttgcg | 500 |
| gccatgcgat gtggacatcc atacactcat taaggcaggg aagaagtgtc | 550 |
| tggctgtgta ccagccagag gcatccatga acttcacact tgcgggctgc | 600 |
| atcagcacac gctcctatca acccaagtac tgtggagttt gcatggacaa | 650 |
| taggtgctgc atcccctaca agtctaagac tatcgacgtg tccttccagt | 700 |
| gtcctgatgg gcttggcttc tcccgccagg tcctatggat taatgcctgc | 750 |
| ttctgtaacc tgagctgtag gaatcccaat gacatctttg ctgacttgga | 800 |
| atcctaccct gacttctcag aaattgccaa cgcggccgca caccaccatc | 850 |
| accatcacca tcactaagtg aggccgcata gataactgat ccagtgtgct | 900 |
| ggaattaatt cgctgtctgc ga | 922 |

```
<210> SEQ ID NO 12
<211> LENGTH: 19
<212> TYPE: DNA
<213> ORGANISM: Mus musculus

<400> SEQUENCE: 12
```

| | |
|---|---|
| ggctgccatc tgtgaccca | 19 |

```
<210> SEQ ID NO 13
<211> LENGTH: 21
<212> TYPE: DNA
<213> ORGANISM: Mus musculus

<400> SEQUENCE: 13
```

| | |
|---|---|
| cataggacct gccgggagaa a | 21 |

```
<210> SEQ ID NO 14
<211> LENGTH: 19
<212> TYPE: DNA
<213> ORGANISM: Mus musculus

<400> SEQUENCE: 14
```

| | |
|---|---|
| gccgtggcag tcctgaggg | 19 |

```
<210> SEQ ID NO 15
<211> LENGTH: 21
<212> TYPE: DNA
<213> ORGANISM: Mus musculus

<400> SEQUENCE: 15
```

| | |
|---|---|
| cagcaccggg cattgacgtt a | 21 |

```
<210> SEQ ID NO 16
<211> LENGTH: 21
<212> TYPE: DNA
<213> ORGANISM: Mus musculus

<400> SEQUENCE: 16
```

| | |
|---|---|
| tggagaaaaa tggccgctac a | 21 |

```
<210> SEQ ID NO 17
```

```
<211> LENGTH: 20
<212> TYPE: DNA
<213> ORGANISM: Mus musculus

<400> SEQUENCE: 17
tggggtgctc ttctcgatgg                                              20

<210> SEQ ID NO 18
<211> LENGTH: 21
<212> TYPE: DNA
<213> ORGANISM: Mus musculus

<400> SEQUENCE: 18
ggacaaatcg gccacgtaca  t                                           21

<210> SEQ ID NO 19
<211> LENGTH: 19
<212> TYPE: DNA
<213> ORGANISM: Mus musculus

<400> SEQUENCE: 19
cttgctccat  cgggtctgc                                              19

<210> SEQ ID NO 20
<211> LENGTH: 42
<212> TYPE: PRT
<213> ORGANISM: Homo sapiens

<400> SEQUENCE: 20

Glu Gln Trp Val Cys Glu Asp Asp Ala Lys Arg Pro Arg Lys Thr
1               5                   10                  15

Ala Pro Arg Asp Thr Gly Ala Phe Asp Ala Val Gly Glu Val Glu
            20                  25                  30

Ala Trp His Arg Asn Cys Ile Ala Tyr Thr Ser Pro
        35                  40

<210> SEQ ID NO 21
<211> LENGTH: 625
<212> TYPE: DNA
<213> ORGANISM: Homo sapiens

<400> SEQUENCE: 21
gaattcacca tgaggtggtt cctgccctgg acgctggcag cagtgacagc             50
agcagccgcc agcaccgtcc tggccactgc agtggtcggt gtgggctgcg            100
tcctggatgg ggtgcgctac aacaacggcc agtccttcca gcctaactgc            150
aagtacaact gcacgtgcat cgacggcgcg gtgggctgca caccactgtg            200
cctccgagtg cgccccccgc gtctctggtg cccccacccg cggcgcgtga            250
gcatacctgg ccactgctgt gagcagtggg tatgtgagga cgacgccaag            300
aggccacgca agaccgcacc ccgtgacaca ggagccttcg atgctgtggg            350
tgaggtggag gcatggcaca ggaactgcat agcctacaca agcccctgga            400
gcccttgctc caccagctgc ggcctggggg tctccactcg gatctccaat            450
gttaacgccc agtgctggcc tgagcaagag agccgcctct gcaacttgcg            500
gccatgcgat gtggacatcc atacactcat taaggcggcc gcacaccacc            550
atcaccatca ccatcactaa gtgaggccgc atagataact gatccagtgt            600
gctggaatta attcgctgtc  tgcga                                      625
```

-continued

```
<210> SEQ ID NO 22
<211> LENGTH: 1131
<212> TYPE: DNA
<213> ORGANISM: Homo sapiens

<400> SEQUENCE: 22
cctcggttct atcgattgaa ttccaccatg aggtggttcc tgccctggac         50
gctggcagca gtgacagcag cagccgccag caccgtcctg gccacggccc        100
tctctccagc ccctacgacc atggacttta ctccagctcc actggaggac        150
acctcctcac gccccaatt ctgcaagtgg ccatgtgagt gcccgccatc         200
cccaccccgc tgcccgctgg gggtcagcct catcacagat ggctgtgagt        250
gctgtaagat gtgcgctcag cagcttgggg acaactgcac ggaggctgcc        300
atctgtgacc cccaccgggg cctctactgt gactacagcg gggaccgccc        350
gaggtacgca ataggagtgt gtgcacaggg ggtcggtgtg ggggtcaccg        400
acaaaactca cacatgccca ccgtgcccag cacctgaact cctggggga         450 ccgtcagtct tcctcttccc cccaaaaccc aaggacaccc tcatgatctc        500
ccggacccct gaggtcacat gcgtggtggt ggacgtgagc cacgaagacc        550
ctgaggtcaa gttcaactgg tacgtggacg gcgtggaggt gcataatgcc        600
aagacaaagc cgcgggagga gcagtacaac agcacgtacc gtgtggtcag        650
cgtcctcacc gtcctgcacc aggactggct gaatggcaag gagtacaagt        700
gcaaggtctc caacaaagcc ctcccagccc ccatcgagaa aaccatctcc        750
aaagccaaag ggcagccccg agaaccacag gtgtacaccc tgcccccatc        800
ccgggaagag atgaccaaga accaggtcag cctgacctgc ctggtcaaag        850
gcttctatcc cagcgacatc gccgtggagt gggagagcaa tgggcagccg        900
gagaacaact acaagaccac gcctcccgtg ctggactccg acggctcctt        950
cttcctctac agcaagctca ccgtggacaa gagcaggtgg cagcagggga       1000
acgtcttctc atgctccgtg atgcatgagg ctctgcacaa ccactacacg       1050
cagaagagcc tctccctgtc tccgggtaaa tgagtgcgac ggccctagag       1100
tcgacctgca gaagcttggc cgccatggcc c                          1131
```